US009862753B2

(12) United States Patent
Yayon et al.

(10) Patent No.: US 9,862,753 B2
(45) Date of Patent: Jan. 9, 2018

(54) FGF-2 VARIANTS HAVING N-TERMINAL DELETIONS AND INCREASED RECEPTOR SELECTIVITY AND METHODS OF USE THEREOF

(71) Applicants: PROCHON BIOTECH LTD., Ness Ziona (IL); HEPACORE LTD., Ness Ziona (IL)

(72) Inventors: Avner Yayon, Moshav Sitria (IL); Eran Rom, Rehovot (IL); Irina Chumakov, Rehovot (IL); Sara Blumenstein, Ramat Gan (IL)

(73) Assignees: PROCHON BIOTECH LTD., Ness Ziona (IL); HEPACORE LTD, Ness Ziona (IL)

( * ) Notice: Subject to any disclaimer, the term of this patent is extended or adjusted under 35 U.S.C. 154(b) by 0 days.

(21) Appl. No.: 14/629,019

(22) Filed: Feb. 23, 2015

(65) Prior Publication Data
US 2015/0322126 A1 Nov. 12, 2015

Related U.S. Application Data

(63) Continuation of application No. 12/443,638, filed as application No. PCT/IL2007/001199 on Oct. 7, 2007, now Pat. No. 8,962,556.

(60) Provisional application No. 60/847,658, filed on Sep. 28, 2006.

(51) Int. Cl.
*C07K 14/50* (2006.01)
*A61K 38/18* (2006.01)
*A61K 38/00* (2006.01)

(52) U.S. Cl.
CPC ........ *C07K 14/503* (2013.01); *A61K 38/1825* (2013.01); *C07K 14/50* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,296,100 | A | 10/1981 | Franco |
| 4,378,347 | A | 3/1983 | Franco |
| 4,683,195 | A | 7/1987 | Mullis et al. |
| 4,683,202 | A | 7/1987 | Mullis |
| 4,950,483 | A | 8/1990 | Ksander et al. |
| 4,965,188 | A | 10/1990 | Mullis et al. |
| 4,994,559 | A | 2/1991 | Moscatelli et al. |
| 5,155,214 | A | 10/1992 | Baird et al. |
| 5,191,067 | A | 3/1993 | Lappi et al. |
| 5,352,589 | A | 10/1994 | Bergonzoni et al. |
| 5,439,818 | A | 8/1995 | Fiddes et al. |
| 5,491,220 | A | 2/1996 | Seddon et al. |
| 5,512,460 | A | 4/1996 | Nauro et al. |
| 5,571,895 | A | 11/1996 | Kurokawa et al. |
| 5,576,288 | A | 11/1996 | Lappi et al. |
| 5,604,293 | A | 2/1997 | Fiddes et al. |
| 5,614,496 | A | 3/1997 | Dunstan et al. |
| 5,656,598 | A | 8/1997 | Dunstan et al. |
| 5,679,637 | A | 10/1997 | Lappi et al. |
| 5,859,208 | A | 1/1999 | Fiddes et al. |
| 5,998,170 | A | 12/1999 | Arakawa et al. |
| 6,294,359 | B1 | 9/2001 | Fiddes et al. |
| 6,352,971 | B1 | 3/2002 | Deisher et al. |
| 6,440,934 | B1 | 8/2002 | Whitehouse |
| 7,288,406 | B2 | 10/2007 | Bogin et al. |
| 8,962,556 | B2 | 2/2015 | Yayon et al. |

FOREIGN PATENT DOCUMENTS

| | | |
|---|---|---|
| WO | 91/09126 A1 | 6/1991 |
| WO | 01/39788 A2 | 6/2001 |
| WO | 02/22779 A2 | 3/2002 |
| WO | 02/36732 A2 | 5/2002 |
| WO | 03/012053 A2 | 2/2003 |
| WO | 03/094835 A2 | 11/2003 |

OTHER PUBLICATIONS

Aviezer et al., "Differential Structural Requirements of Heparin and Heparan Sulfate Proteoglycans That Promote Binding of Basic Fibroblast Growth Factor to its Receptor," The Journal of Biological Chemistry, vol. 269, No. 1, pp. 114-121,(1994).
Bellosta et al. "Identification of Receptor and Heparin Binding Sites in Fibroblast Growth Factor 4 by Structure-Based Mutagenesis," Molecular and Cellular Biology. vol. 21, No. 17, pp. 5946-5957, (2001).
Bikfalvi et al., "Biological Roles of Fibroblast Growth Factor-2," Endocrine Reviews, vol. 18,No. 1, pp. 26-45, (1997).
Imamura et al., "Recovery of Mitogenic Activity of a Growth Factor Mutant with a Nuclear Translocation Sequence" Science, vol. 249, pp. 1567-1570, (1990).
Kastrup et al., "X-ray Structure of the 154-Amino-Acid Form of Recombinant Human Basic Fibroblast Growth Factor. Comparison with the Truncated 146-Amino-Acid Form," Acta Crystallographica, Section D53, pp. 160-168(1997).
Kuroda et al., "Anabolic Effect of Aminoterminally Truncated Fibroblast Growth Factor 4 (FGF4) on Bone," Bone vol. 25, No. 4, Oct. 1999, p. 431-437, (1999).
Mohammadi et al., "Structural Basis for Fibroblast Growth Factor Receptor Activation," Cytokine & Growth Factor Reviews 16, pp. 107-137, (2005).
Okada-Ban et al., "Molecules in focus, Fibroblast Growth Factor-2," The International Journal of Biochemistry & Cell Biology 32, pp. 263-267, (2000).
Olsen et al., "Insights into the Molecular Basis for Fibroblast Growth Factor Receptor Autoinhibition and Ligand-Binding Promiscuity," Proc. Natl. Acad. Sci. vol. 101, pp. 935-940, (2004).
Ornitz et al. "Receptor Specificity of the Fibroblast Growth Factor Family," The Journal of Biological Chemistry, vol. 271, No. 25 Issue of Jun. 21, pp. 15292-15297, (1996).
Ornitz, "FGFs, Heparan Sulfate and FGFRs: Complex Interactions Essential for Development," Bioessays 22, pp. 108-112, (2000).

(Continued)

*Primary Examiner* — Christine J Saoud
(74) *Attorney, Agent, or Firm* — Brown Rudnick LLP; Thomas C. Meyers

(57) ABSTRACT

The present invention relates to the design, manufacture and use of fibroblast growth factor (FGF) polypeptides having improved receptor specificity. In particular, the invention relates to isolated FGF2 polypeptides comprising a truncated N-terminus and optionally N-terminal amino acid substitutions. The present invention provides polypeptides, nucleic acids encoding the polypeptides, compositions comprising same and methods for use thereof.

7 Claims, 24 Drawing Sheets

(56) References Cited

OTHER PUBLICATIONS

Ornitz and Itoh, "Protein Family Review, Fibroblast Growth Factors," Genome Biology, vol. 2, No. 3, pp. 3005.1-3005.12, (2001).
Plotnikov et al., "Crystal Structures of Two FGF-FGFR Complexes Reveal the Determinants of Ligand-Receptor Specificity," Cell vol. 101, pp. 413-424, (2000).
Presta et al., "Subcellular Localization and Biological Activity of Mr 18,000 Basic Fibroblast Growth Factor: Site-Directed Mutagenesis of a Putative Nuclear Translocation Sequence," Growth Factors, vol. 9, pp. 269-278, (1993).
Seno et al., "Carboxyl-Terminal Structure of Basic Fibroblast Growth Factor Significantly Contributes to its Affinity for Heparin" Eur. J. Biochem. 188, pp. 239-245, (1990).
Springer et al., "Identification and Concerted Function of Two Receptor Binding Surfaces on Basic Fibroblast Growth Factor Required for Mitogenesis," The Journal of Biological Chemistry, vol. 269, No. 43, Issue of Oct. 28, pp. 26879-26884, (1994).
Wong et al., "Analysis of Putative Heparin-binding Domains of Fibroblast Growth Factor-1," The Journal of Biological Chemistry, vol. 270, No. 43, Issue of Oct. 27, pp. 25805-25811,(1995).
Yayon et al. "Cell Surface, Heparin-like Molecules Are Required for Binding of Basic Fibroblast Growth Factor to its High Affinity Receptor," Cell, vol. 64, pp. 841-848, (1991).
Yayon et al. "Isolation of Peptides That Inhibit Binding of Basic Fibroblast Growth Factor to its Receptor From a Random Phage-Epitope Library," Proc. Natl. Acad. Sci. USA, vol. 90, pp. 10643-10647, (1993).
Zhu et al., Analysis of High-Affinity Binding Determinants in the Receptor Binding Epitope of Basic Fibroblast Growth Factor, Protein Engineering, vol. 10, pp. 417-421, (1997).
International Search Report, PCT/IL07/01199, dated Sep. 16, 2008.

Figure 1A

```
--β1---
KRLYCKN-GGFFLRIHPDGRVDGVREKSDPHIKLQLQAEERGVVSIKGVC
RRLYCNVGIGFHLQALPDGRIGGAHAD-TRDSLLELSPVERGVVSIFGVA

ANRYLAMKEDGRLLASKCVTDE-CFFFERLESNNYNTYRSRKYTSWYVALKRTGQ
SRFFVAMSSKGKLYGSPFFTDE-CTFKEILLPNNYNAYESYKYPGMFIALSKNGK
                       β8-β9 loop YKLGSKTGPGQKAILFLPMS  | FGF2-HUM (SEQ ID NO:1)
TKKGNRVSPTMKVTHFLPRL  | FGF4-HUM (SEQ ID NO:2)
```

Figure 1B

```
              Δ24Δ25Δ26  Δ31
                \ / /     /
1   MAAGSITTLP ALPEDGGSGA FPPGHFKDPK RLYCKNGGFF LRIHPDGRVD

51  GVREKSDPHI KLQLQAEERG VVSIKGVCAN RYLAMKEDGR LLASKCVTDE

101 CFFFERLESN NYNTYRSRKY TSWYVALKRT GQYKLGSKTG PGQKAILFLP

151 MSAKS (SEQ ID NO:3)
```

Figure 1C

```
1   MSGPGTAAVA LLPAVLLALL APWAGRGGAA APTAPNGTLE AELERRWESL
                                         ┌Δ78
51  VALSLARLPV AAQPKEAAVQ SGAGDYLLGI KRLRRLYCNV GIGFHLQALP

101 DGRIGGAHAD TRDSLLELSP VERGVVSIFG VASRFFVAMS SKGKLYGSPF

151 FTDECTFKEI LLPNNYNAYE SYKYPGMFIA LSKNGKTKKG NRVSPTMKVT

201 HFLPRL (SEQ ID NO:4)
```

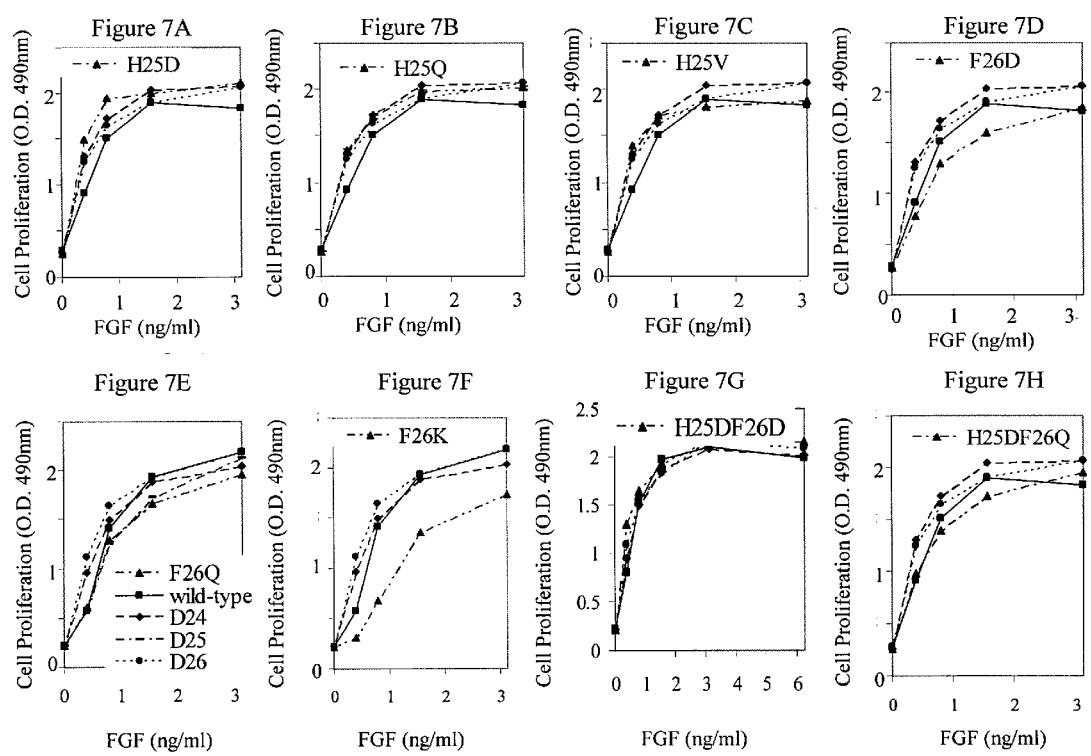

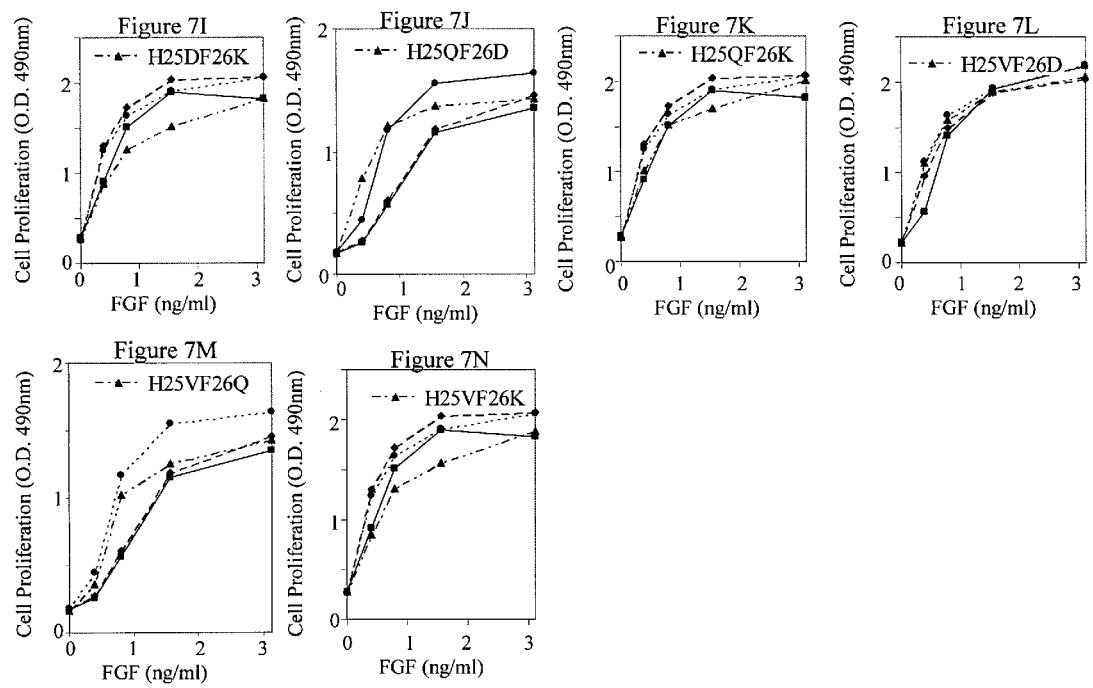

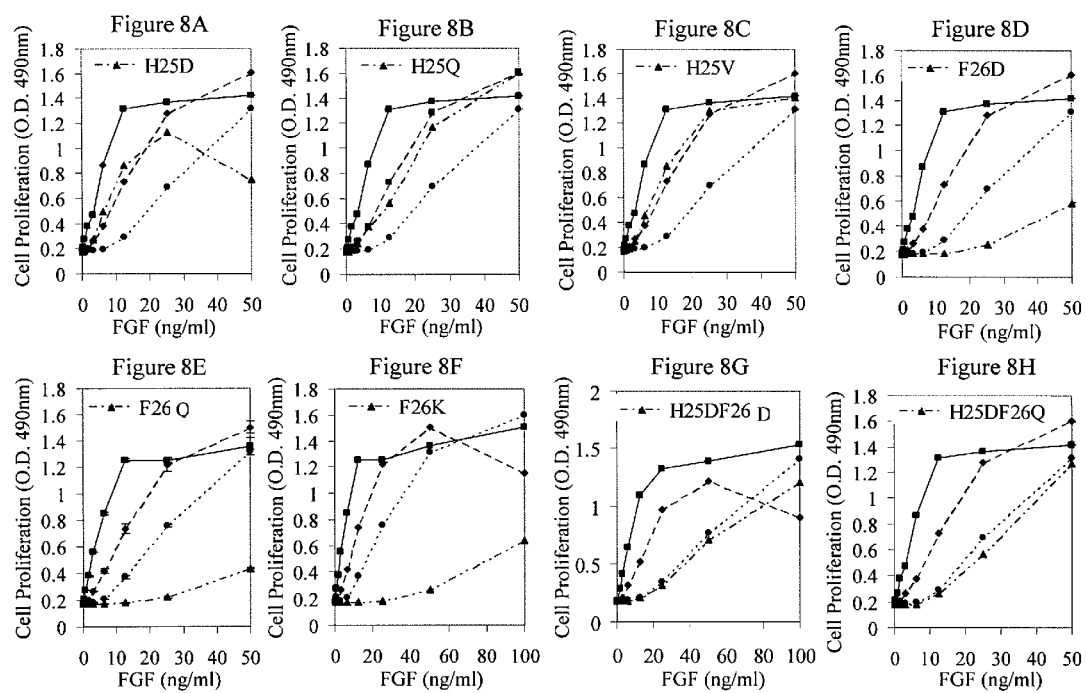

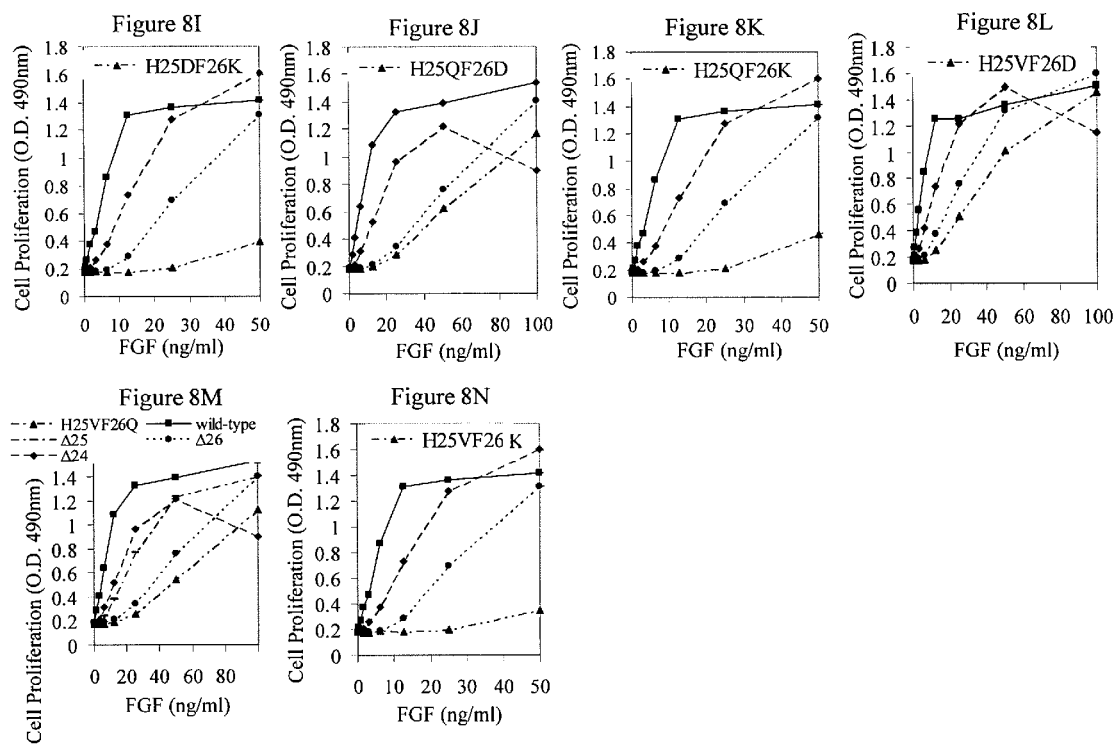

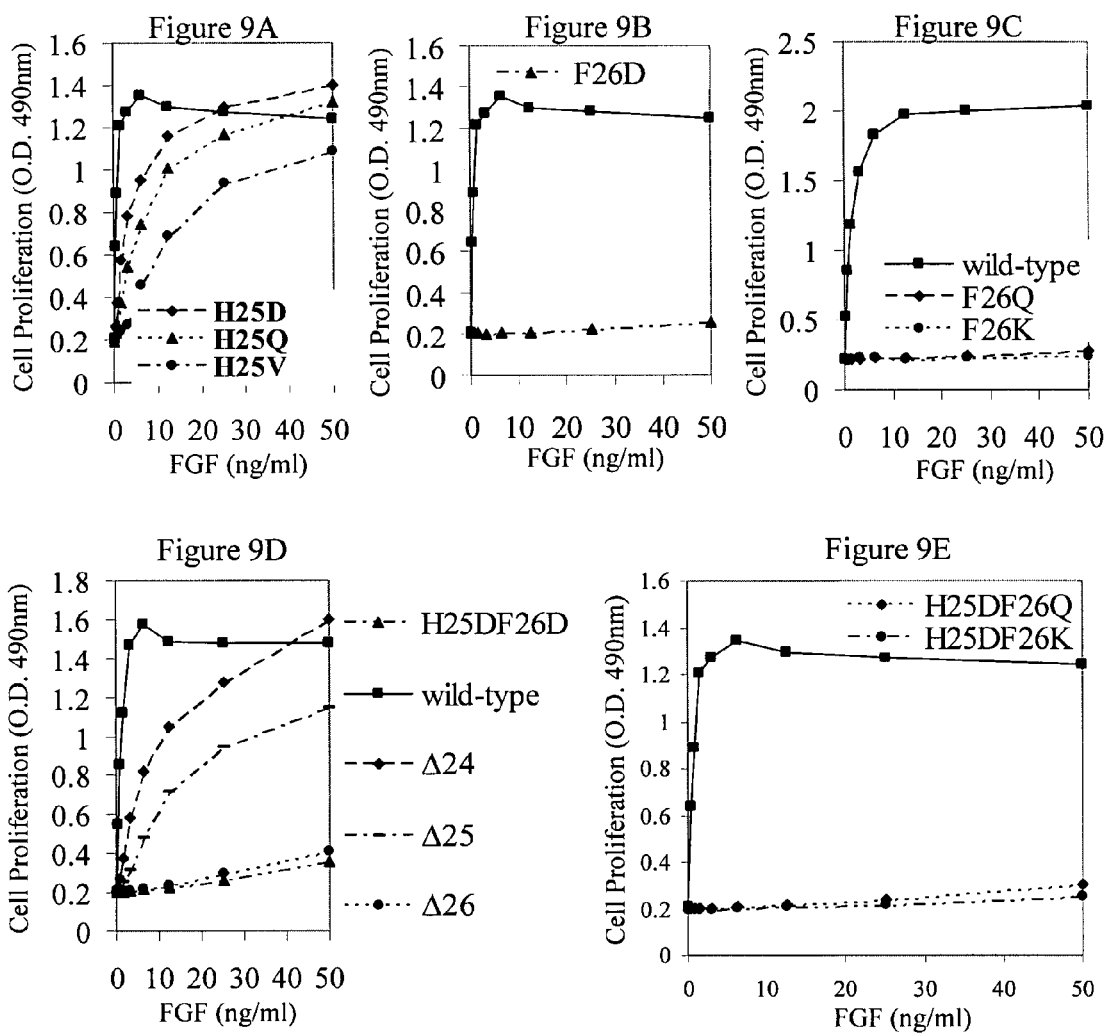

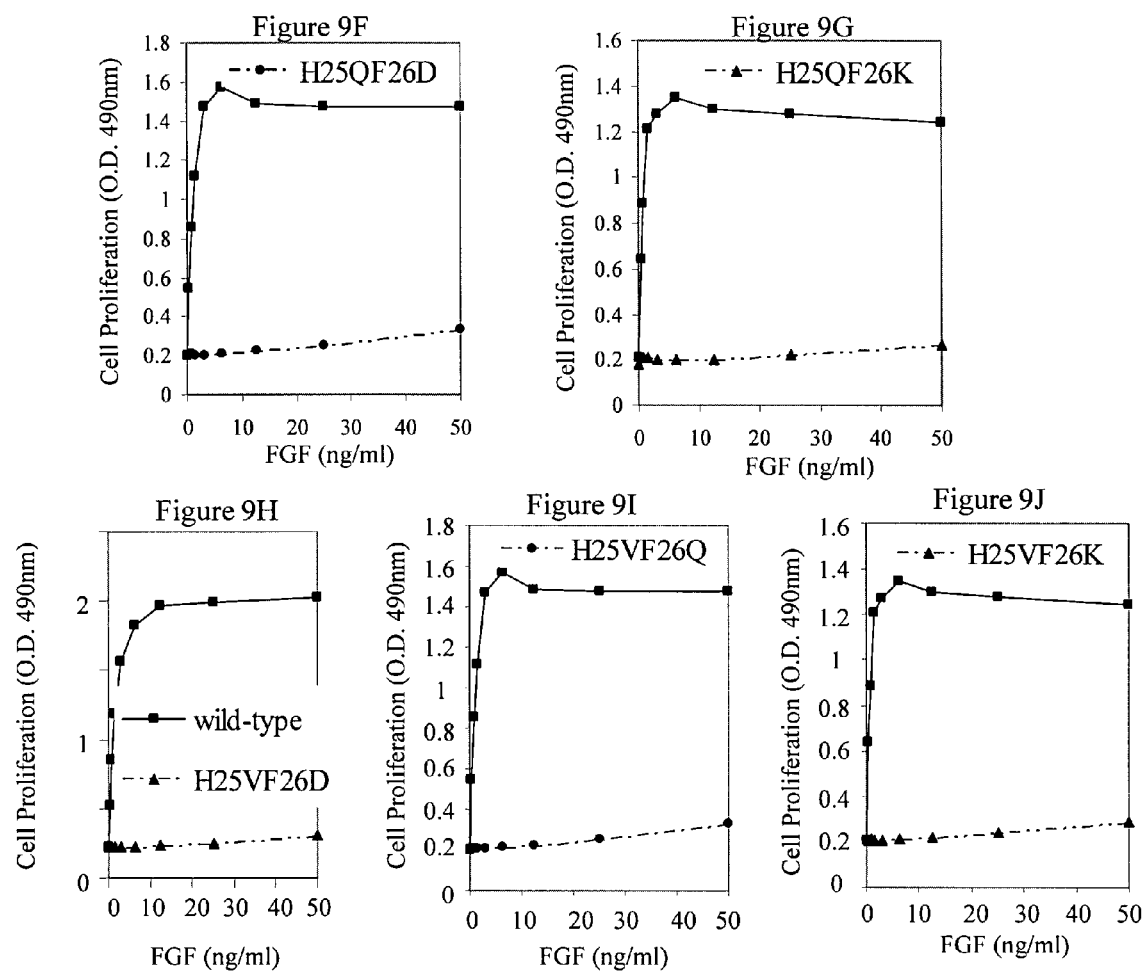

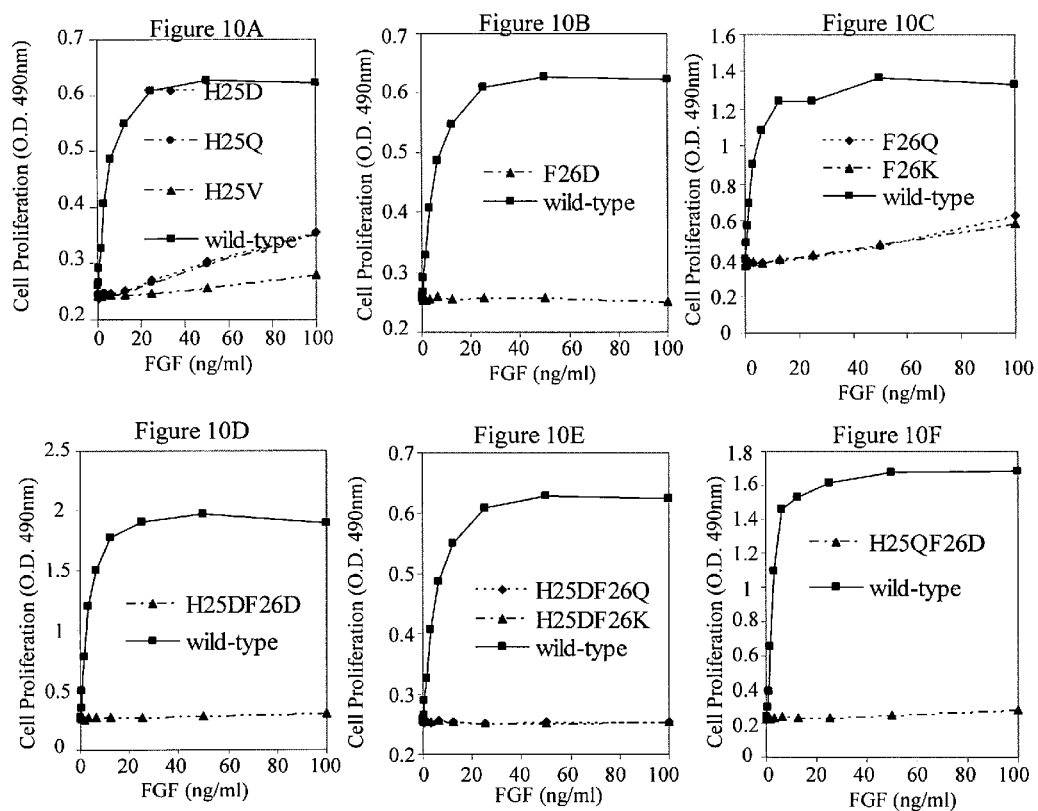

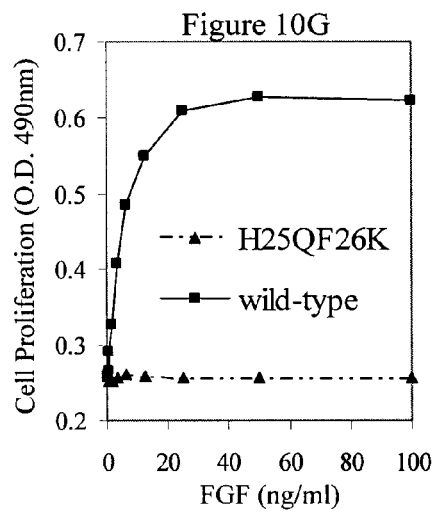
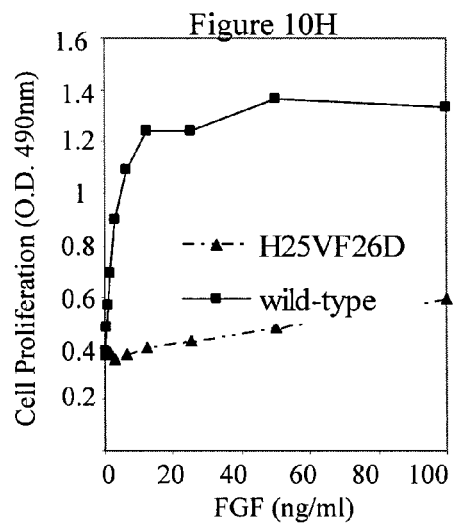
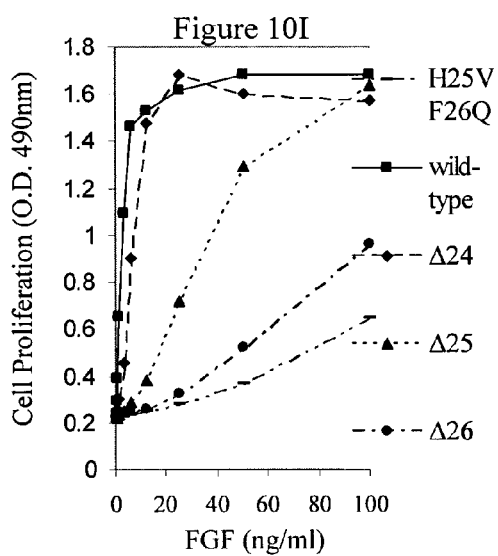
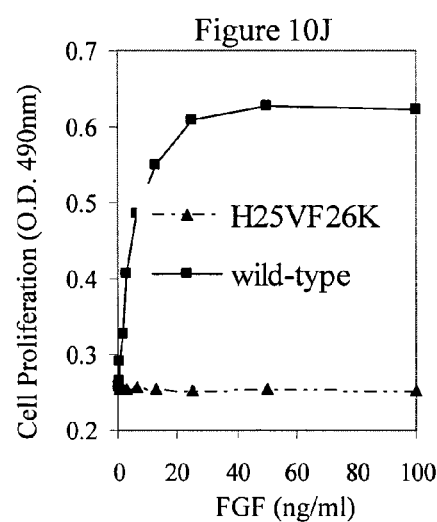

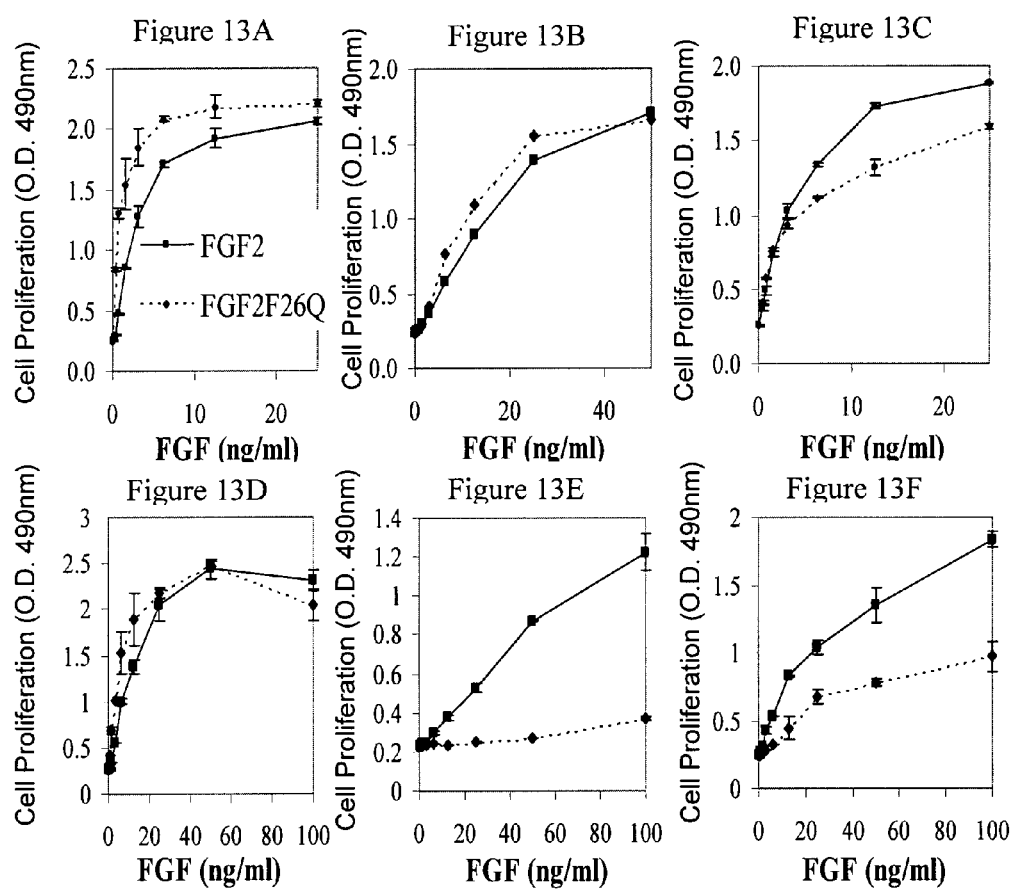

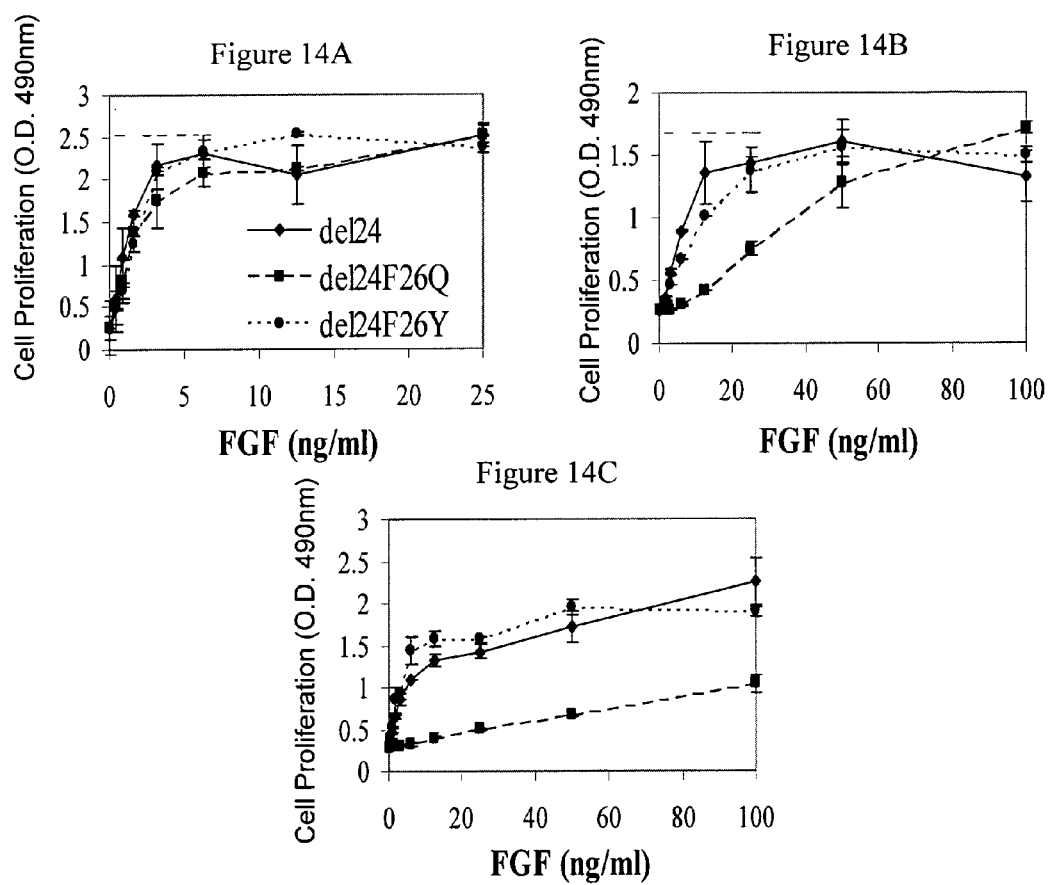

FGF-2 VARIANTS HAVING N-TERMINAL DELETIONS AND INCREASED RECEPTOR SELECTIVITY AND METHODS OF USE THEREOF

RELATED APPLICATIONS

This application is a continuation of U.S. non-provisional application Ser. No. 12/443,638 filed Nov. 2, 2010, which is a national stage entry of PCT/IL07/01199 filed Oct. 7, 2007, which claims the benefit of and priority to provisional application 60/847,658 filed Sep. 28, 2006, each of which is incorporated by reference.

FIELD OF THE INVENTION

The present invention relates to fibroblast growth factor (FGF) variants, having improved receptor specificity. In particular, the invention relates to isolated FGF2 and FGF4 polypeptides having specific N-terminus modifications including N-terminal truncations and N-terminal amino acid substitutions. The present invention provides polypeptides, nucleic acids encoding the polypeptides, compositions comprising same and methods for use thereof.

BACKGROUND OF THE INVENTION

Fibroblast Growth Factors and their Receptors

Fibroblast growth factors (FGFs) comprise a large family of evolutionarily conserved polypeptides involved in a variety of biological processes including morphogenesis, angiogenesis, and tissue remodeling as well as in the pathogenesis of numerous diseases. The various members of this family stimulate the proliferation of a wide spectrum of cells, including those deriving from mesenchymal, endothelial, epithelial and neuroectodermal origin. FGFs are expressed in a strict temporal and spatial pattern during development and have important roles in patterning and limb formation (reviewed in Ornitz, 2000). All members of the FGF family share a homology core domain of about 120 amino acids, 28 aa residues are highly conserved and four are identical. The adjacent N- and C-termini are of variable length and share limited homology. The core domain comprises both the primary receptor binding sites and a heparin-binding domain, which are distinct from each other (reviewed in Ornitz and Itoh, 2001).

Fibroblast growth factor 2, also known as FGF2, basic FGF, bFGF, prostatin and heparin binding growth factor 2, is highly conserved among species and has been shown to stimulate the proliferation of a wide variety of cell types. Human FGF2 is expressed in several forms, a 210 aa precursor, a 155 aa form, a 146 aa N-terminal truncated form and several others (reviewed in Okada-Ban et al., 2000). A method for purifying recombinant FGF2 has been disclosed in WO 91/09126.

The biological response of cells to FGF is mediated through specific, high affinity (Kd 20-500 pM) cell surface receptors that possess intrinsic tyrosine kinase activity and are phosphorylated upon binding of FGF. Five distinct Fibroblast Growth Factor Receptors (FGFRs) have been identified, FGFR1-4 are transmembrane-protein kinases while FGFR5 lacks a tyrosine kinase domain. The FGFR extracellular domain consists of three immunoglobulin-like (Ig-like) domains (D1, D2 and D3), a heparin binding domain and an acidic box. Alternative splicing of D3 in FGFR1-3 mRNAs generates six different receptor subtypes, each having unique ligand specificity and tissue distribution pattern.

Another critically functional component in receptor activation is the binding to soluble heparin or a heparan sulfate proteoglycan. Different models have been proposed to explain the role of heparan sulfate proteoglycans (HSPG) in FGF signaling, including the formation of a functional tertiary complex between FGF, FGFR and an HSPG (Yayon et al., 1991). Most naturally occurring heparan sulfate are incapable of promoting heparin dependent high affinity FGF receptor binding and activation (Aviezer et al., 1994). Moreover, heparan sulfate which is locally secreted by cells, masks receptor specificity of the FGF ligands.

FGFRs and Disease

A number of birth defects affecting the skeleton are associated with mutations in the genes encoding FGF receptors. Certain FGFRs have been implicated in certain malignancies and proliferative diseases. FGFR3 is the most frequently mutated oncogene in transitional cell carcinoma (TCC) of the bladder where it is mutated in about 50% of the cases; the FGFR3IIIc isoform is ectopically expressed in 15-20% of patients with multiple myeloma and is over expressed in the white blood cells of chronic myeloid leukemia (CML) patients. A mutation in FGFR3 is linked to cervical carcinoma. FGFR4 was shown to be associated with pituitary tumors and breast cancer progression. In contrast, certain FGF ligands have been shown to be highly useful for treating indications including wounds (U.S. Pat. Nos. 4,950,483, 5,859,208 and 6,294,359), myocardial infarction (U.S. Pat. Nos. 4,296,100 and 4,378,347), skeletal disorders (U.S. Pat. Nos. 5,614,496 and 5,656,598) and for remodeling cardiac tissue (U.S. Pat. No. 6,352,971).

FGF Variants and Receptor Specificity

All members of the FGF family share a homology core domain of about 120 amino acids (aa), 28 aa residues are highly conserved and four are identical. Structural studies on several FGFs identified twelve antiparallel β strands each one adjacent to β-loops comprising the core region, conserved throughout the family. The core domain comprises the primary FGFR and heparin binding sites. Receptor binding regions are distinct from heparin binding regions (reviewed in Ornitz and Itoh, 2001).

In view of the large number of FGFs and FGF receptor variants, a major question regarding FGF function is their receptor specificity or selectivity. Most FGF ligands bind more than one receptor subtype and such a degree of cross-reactivity is shared between all FGF receptors, demonstrating a highly redundant signaling network. All FGFRs tested so far bind FGF1 (acidic FGF, aFGF) with moderate to high affinity, further demonstrating the apparent redundancy in the FGF system (Ornitz et al., 1996).

Various types of FGF variants are known in the art. U.S. Pat. No. 6,294,359 discloses agonist and antagonist analogs of FGF2 that comprise amino acid substitutions in the C8 and C96 residues. U.S. Pat. No. 5,352,589 discloses derivatives in the C78 and C96 residues. U.S. Pat. No. 5,352,589 discloses derivatives of FGF2 that act as antagonists or speragonists. On particular construct comprises a human or boine derivatie wherein amino acids 27-32 have been deleted. Wong et al., (1995) identified putative heparin binding domains in FGF1 (154aa form) based on consensus sequence motifs, including amino acids 22-27. Nevertheless, according to that citation substitution of Lys23, Lys24 or Lys26 with glycine residues had no effect on the activity of FGF1.

Attempts have been made to achieve altered FGF receptor specificity by mutating or truncating the ligands, by means of mutations introduced at certain locations within the gene encoding for the proteins. Certain truncated and mutated variants have been disclosed by some of the inventors of the present invention in PCT publications WO 02/36732 and WO 03/094835. International patent applications WO 02/36732 and WO 03/094835 of some of the applicants of the present invention, disclose FGF variants having at least one amino acid substitution in the β8-β9 loop, and/or an N- and/or C-terminal truncation, having increased receptor specificity to one receptor subtype compared to the corresponding wild type FGF. PCT publication WO 02/36732 discloses specific FGF9 variants having 36, 44 or 63 amino acid truncations at the N-terminus. The shortest variant was shown to retain weak activity towards FGFR3 while losing almost all activity towards FGFR1. PCT publication WO 03/094835 teaches an FGF4 variant having both an N-terminal truncation (55 amino acids) and an amino acid substitution in the β8-β9 loop, the variant exhibiting enhanced receptor specificity towards FGFR3 with substantially unchanged activity towards FGFR1 and FGFR2.

Several investigators have demonstrated FGF mutants and variants affecting receptor and heparin binding. Kuroda et al., (1999) demonstrated that a full-length FGF4 polypeptide (191 aa) and an N-terminal truncated version containing 134 amino acid residues exhibit comparable cellular proliferation on NIH3T3 cells and increase of bone density. The shortest form of FGF4 tested, containing only 111 amino acid residues, exhibited limited growth stimulatory activity.

U.S. Pat. No. 5,998,170 discloses a biologically active FGF16 molecule having from one to thirty-four amino acids deleted from the N-terminus or from one to eighteen amino acids deleted from the C-terminus. The truncated ligands were shown to retain biological activity including hepatocellular proliferation and increased production of triglycerides and serum proteins, when administered to animals.

X-ray crystallography has been used in an attempt to study the basis of specificity of FGFs to their receptors (Plotnikov et al., 2000; Olsen, et al., 2004; Mohammadi et al., 2005). The role of the N-terminal domain of the FGFs was resolved in only a few of the abovementioned crystal structures. Olsen et al., (2004) compared receptor binding of a full length FGF1 (155 aa) to a N-terminal truncated form (21-155) and show that the N-terminus of FGF1 may be relevant to binding and activation of the FGFR3c isoform. The (21-155) form also exhibits reduced FGFR2 and FGFR3 phosphorylation.

Plotnikov et al., (2000) determined the crystal structures of FGF1 and FGF2 complexed with the ligand binding domains (Ig-like domains 2 and 3) of FGFR1 and FGFR2, respectively and shows that certain N-terminal residues of FGF, in particular Phe17 and Lys18 of FGF2 (Lys27 of 155 aa form), could be in contact with the D3 domain of FGFR2. The authors speculated, but did not provide experimental evidence, that amino acids 7-13 of FGF1 play a role in receptor binding. The deletion of that specific sequence, which had originally been proposed to be a nuclear localization sequence, reduces the ability of FGF1 to induce cell proliferation in endothelial cell lines by about 250-fold (Imamura et al., 1990). These findings neither suggest nor teach that the deletion of that specific sequence would affect receptor selectivity.

Seno et al., (1990) teach certain bFGF variants having N- and C-terminus truncations and have characterized their ability to bind heparin. The mitogenic activity of those variants in BALB/c3T3 cells was determined and the N14 variant (corresponding to a 22 amino acid truncation of the 155 aa bFGF species) showed an activity of 68% that of the mature form of bFGF. A much larger truncation, N41, which corresponds to a 49 amino acid truncation of the 155 aa species, exhibits only about 2% mitogenic activity. There is neither teaching nor suggestion of a truncated FGF exhibiting receptor selectivity toward one or another FGFR species.

In another study the basic residues in an analogous stretch of FGF2 (aa 27-31, 155 aa form) were modified to neutral glutamine residues, specifically K27Q, K30Q and R31Q (Presta et al., 1993). That mutant retains receptor binding capacity and mitogenic activity on endothelial cells yet exerts reduced uPA inducing activity.

The above disclosures show that modifications in certain N-terminal residues affect cell proliferation, yet they neither teach nor suggest that mutations or substitutions in N-terminal residues of FGF would affect receptor selectivity.

A hexapeptide, consisting of N-terminal amino acids 13-18 of FGF2 (146 aa form, corresponding to aa 22-27 of the 155 aa form), was shown to inhibit binding of FGF2 to FGFR-1, implicating this motif in receptor binding (Yayon et al, 1993). There was neither teaching nor suggestion of receptor specificity.

Attempts have been made to alter FGF receptor specificity and heparin binding by means of site directed mutagenesis within the FGF genes. U.S. Pat. No. 5,512,460 discloses a biologically active FGF9 (glia activating factor, GAF) molecule comprising N-terminus and C-terminus truncations of 53 aa and 13 aa, respectively. U.S. Pat. No. 5,571,895 discloses an N-terminus 54 aa deletion yielding a 154 aa protein retaining its biological activity, as measured by glial cell growth activity.

U.S. Pat. No. 5,491,220 to one of the inventors of the present application discloses structural analogues of FGF2 comprising substitution of the β9-β10 loop having altered biological properties and binding specificity.

Springer et al., (1994) identified two FGFR binding sites on FGF2, the first includes hydrophobic residues Y24, Y103, L140 and M142 and polar residues R44, and N101. The author concludes that R44 and N101 were the only polar residues observed to be important in the primary binding interaction between FGF2 and FGFR.

In an attempt to identify FGF2 antagonists having reduced binding affinity towards FGFR1. Zhu et al. (1997) tested N101A, N102A, Y103A, N104A and T105A muteins and their binding affinity to FGFR1. These correspond to amino acid residues N110, N111, Y112, N113 and T114 of the 155 aa species. The N101A and N102A muteins were shown to have FGFR1 binding similar to that of the wild type protein, while the N104A mutein exhibited 400 fold reduced FGFR1 binding.

There is neither teaching nor suggestion of receptor selectivity in the above-cited references.

Bellosta et al., (2001) have disclosed mutated and truncated FGF4 variants having reduced receptor binding and a low mitogenic potential. Of interest is a truncated variant, which lacks 78 N-terminal amino acids and, according to the published data, retains the core domain, exhibiting FGFR binding affinities similar to that of the wild type ligand. Certain mutations within the core domain were shown to have a deleterious effect on both DNA synthesis and receptor binding.

The extensive efforts made to produce truncation, deletion and point mutation variants in FGF have resulted in certain alterations in receptor specificity. There remains an unmet need for highly active and selective ligands for the various FGF receptor isoforms, useful in selective stimulation or inhibition of these receptors, thereby addressing the clinical manifestations associated with receptor mutations, and modulation of various biological functions.

It is to be understood that known variants of FGF are excluded explicitly from the present invention.

A need for FGF variants having increased receptor selectivity is manifest. Lack of receptor selectivity is often detrimental to tissue repair and regeneration both ex vivo and in vivo. For instance, FGFR1 activation is often critical for cell survival and proliferation; hence, a ligand having enhanced FGFR1 specificity would be ideal for supporting physiological FGF mediated activities in processes such as wound healing, independent of the heparan sulfate environment.

SUMMARY OF THE INVENTION

The present invention provides Fibroblast Growth Factor (FGF) polypeptides that show an increase in receptor selectivity when compared to the corresponding wild type protein. In particular, the invention provides FGF polypeptides in which the wild type amino acid sequence has been modified to introduce an N-terminal truncation. It is now disclosed that specific N-terminal modified FGF2 and FGF4 polypeptide variants having increased receptor selectivity, are useful in research and clinical applications.

The present inventors have found unexpectedly that certain N-terminal variants of FGF2 and FGF4 have enhanced receptor selectivity. Wild type FGF2 is known to activate FGFR1, FGFR2 and FGFR3 indiscriminately. In contrast, certain FGF2 variants of the present invention are now shown to selectively activate only one or two of those receptors. The clinical applications are manifold, including receptor selective agonist ligands useful for, inter alia, wound healing, bone and cartilage regeneration and stem cell proliferation and differentiation.

In one aspect the present invention provides an isolated N-terminal modified fibroblast growth factor polypeptide selected from FGF2 and FGF4. Accordingly, the present invention provides an isolated variant polypeptide of a fibroblast growth factor selected from the group consisting of FGF2 and FGF4 comprising an N-terminal deletion; wherein the FGF2 variant polypeptide retains between 0 and 11 amino acid residues at the N-terminus extending beyond the Leu-Tyr-Cys (LYC) motif of the β1 strand of the core domain; and wherein the variant polypeptide has increased receptor selectivity when compared to the corresponding isolated wild type FGF polypeptide by a gain of activity or loss of activity by at least a factor of two toward at least one receptor subtype but not toward all FGFR subtypes.

The FGF2 core domain is set forth in SEQ ID NO:1; the FGF4 core domain is set forth in SEQ ID NO:2. For reference purposes, the 155 aa FGF2 polypeptide (18 kD isoform) is set forth in SEQ ID NO:3 (NP_001997) and the 206 aa FGF4 polypeptide (FGF4 precursor) is set forth in SEQ ID NO:4 (NP_001998.).

The amino acid sequences of the FGF2 and FGF4 core domains are shown in FIG. 1A. The amino acid sequences of the β1 strand are bolded. The Leu-Tyr-Cys (LYC) motif is underlined.

In some embodiments the isolated FGF variant polypeptide is an FGF2 variant. In certain embodiments the FGF2 retains between 0 and 5 amino acid residues at the N-terminus extending beyond the LYC motif of the β1 strand of the core domain. In some embodiments the variant polypeptide is selected from a group of polypeptides having an amino acid sequence set forth in any one of SEQ ID NOS: 7-12. In one embodiment the FGF2 variant polypeptide has a sequence set forth in SEQ ID NO:7. In another embodiment the FGF2 variant polypeptide has a sequence set forth in SEQ ID NO:12.

A description of the FGF2 N-terminal variant polypeptides is set forth hereinbelow. It is to be noted that the N-terminal methionine residue (Met) is required for expression in the bacterial expression system, yet it is generally post-translationally cleaved and a polypeptide lacking the first Met is obtained. However, it is to be understood that variant polypeptides having the N-terminal methionine are encompassed in the present application.

The FGF2 variant polypeptides are characterized as follows:

SEQ ID NO:5, represents FGF2$^{\Delta 24}$, having a 23 amino acid N-terminal truncation with the Gly24 replaced by a Met residue. This polypeptide is encoded by a polynucleotide sequence set forth in SEQ ID NO:34. The expressed FGF2$^{\Delta 24}$ polypeptide has a 7 amino acid N-terminal sequence preceding the LYC motif of the β1 strand of the core domain. The sequence may further comprise a Met residue at the N-terminus.

SEQ ID NO:6, represents FGF2$^{\Delta 25}$, having a 24 amino acid N-terminal truncation with the His25 replaced by a Met residue. This polypeptide is encoded by a polynucleotide sequence set forth in SEQ ID NO:35. The expressed FGF2$^{\Delta 25}$ polypeptide has a 6 amino acid N-terminal sequence preceding the LYC motif of the β1 strand of the core domain. The sequence may further comprise a Met residue at the N-terminus.

SEQ ID NO:7, represents FGF2$^{\Delta 26}$, having a 25 amino acid N-terminal truncation with the Phe26 replaced by a Met residue. This polypeptide is encoded by a polynucleotide sequence set forth in SEQ ID NO:36. The expressed FGF2$^{\Delta 26}$ polypeptide has a 5 amino acid N-terminal sequence preceding the LYC motif of the β1 strand of the core domain. The sequence may further comprise a Met residue at the N-terminus.

SEQ ID NO:8, represents FGF2$^{\Delta 27}$, having a 26 amino acid N-terminal truncation with the Lys27 replaced by a Met residue. This polypeptide is encoded by a polynucleotide sequence set forth in SEQ ID NO:37. The expressed FGF2$^{\Delta 27}$ polypeptide has a 4 amino acid N-terminal sequence preceding the LYC motif of the β1 strand of the core domain. The sequence may further comprise a Met residue at the N-terminus.

SEQ ID NO:9, represents FGF2$^{\Delta 28}$, having a 27 amino acid N-terminal truncation with the Asp28 replaced by a Met residue. This polypeptide is encoded by a polynucleotide sequence set forth in SEQ ID NO:38. The expressed FGF2$^{\Delta 28}$ polypeptide has a 3 amino acid N-terminal sequence preceding the LYC motif of the β1 strand of the core domain. The sequence may further comprise a Met residue at the N-terminus.

SEQ ID NO:10, represents FGF2$^{\Delta 29}$, having a 28 amino acid N-terminal truncation with the Pro29 replaced by a Met residue. This polypeptide is encoded by a polynucleotide sequence set forth in SEQ ID NO:39. The expressed FGF2$^{\Delta 29}$ polypeptide has a 2 amino acid N-terminal sequence preceding the LYC motif of the β1 strand of the core domain. The sequence may further comprise a Met residue at the N-terminus.

SEQ ID NO:11, represents FGF2$^{\Delta 30}$, having a 29 amino acid N-terminal truncation with the Lys30 replaced by a Met residue. This polypeptide is encoded by a polynucleotide sequence set forth in SEQ ID NO:40. The expressed FGF2$^{\Delta 30}$ polypeptide has a 1 amino acid N-terminal sequence preceding the LYC motif of the β1 strand of the core domain. The sequence may further comprise a Met residue at the N-terminus.

SEQ ID NO:12, represents FGF2$^{\Delta 31}$, having a 30 amino acid N-terminal truncation with the Arg31 replaced by a Met residue. This polypeptide is encoded by a polynucleotide sequence set forth in SEQ ID NO:41. The expressed FGF2$^{\Delta 31}$ polypeptide has no N-terminal sequence preceding the LYC motif of the β1 strand of the core domain. The sequence may further comprise a Met residue at the N-terminus.

In some embodiments the FGF variant polypeptide further comprises at least one additional modification in its polypeptide sequence, wherein the modification is selected from an amino acid deletion, an amino acid substitution and an amino acid insertion. In some embodiments the additional modification is an amino acid residue substitution in the beta8-beta9 loop. In one embodiment the variant polypeptide is an FGF2 variant polypeptide denoted herein FGF2$^{\Delta 26}$N111G having sequence set forth in SEQ ID NO:13. The corresponding polynucleotide sequence is set forth in SEQ ID NO:42. The sequence may further comprise a Met residue at the N-terminus.

For convenience, the above-mentioned FGF2 variants are listed in table I with their sequence identifiers.

TABLE I

FGF2 variants and their associated sequence identifiers.

|  | SEQ ID NO: POLYPEPTIDE | SEQ ID NO: POLYNUCLEOTIDE |
|---|---|---|
| FGF2$^{\Delta 24}$ | 5 | 34 |
| FGF2$^{\Delta 25}$ | 6 | 35 |
| FGF2$^{\Delta 26}$ | 7 | 36 |
| FGF2$^{\Delta 27}$ | 8 | 37 |
| FGF2$^{\Delta 28}$ | 9 | 38 |
| FGF2$^{\Delta 29}$ | 10 | 39 |
| FGF2$^{\Delta 30}$ | 11 | 40 |
| FGF2$^{\Delta 31}$ | 12 | 41 |
| FGF2$^{\Delta 26}$N111G | 13 | 42 |

In other embodiments the variant polypeptide comprises at least one amino acid substitution in the retained N-terminus sequence. In some embodiments the variant polypeptide is an FGF2 variant having a sequence set forth in any one of SEQ ID NO:14-16.

SEQ ID NO:14 denoted herein FGF2$^{\Delta 24}$H25X1, wherein X1 is an amino acid residue other than His. In some embodiments X1 is selected from the group of amino acid residues consisting of Q, K and V. In certain embodiments X1 is selected from K and V. The sequence may further comprise a Met residue at the N-terminus.

SEQ ID NO:15 denoted herein FGF2$^{\Delta 24}$F26X2, wherein X2 is an amino acid residue other than Phe. In some embodiments X2 is selected from the group of amino acid residues consisting of D, Q, and K. The sequence may further comprise a Met residue at the N-terminus.

SEQ ID NO:16 denoted herein FGF2$^{\Delta 24}$H25X3-F26X4, wherein X3 is an amino acid residue other than His and X4 is an amino acid residue other than Phe. In some embodiments X3 is selected from the group of amino acid residues consisting of D, Q, K and V and X4 is selected from the group of amino acid residues consisting of D, Q and K. The sequence may further comprise a Met residue at the N-terminus.

In some embodiments the additional modification is an amino acid residue substitution at the N-terminus. In one embodiment the variant polypeptide is an FGF2 variant polypeptide in which Phe 26 is replaced by Gln denoted herein FGF2$^{F26Q}$ having the sequence set forth in SEQ ID NO:90. The corresponding polynucleotide sequence is set forth in SEQ ID NO:91.

According to some embodiments the FGF2 variant is selected from any one of SEQ ID NO:17-23 or 25-33, as characterized hereinbelow in Table II:

TABLE II

FGF2 variants and their associated sequence identifiers.

|  | POLYPEPTIDE SEQ ID NO: | POLYNUCLEOTIDE SEQ ID NO: |
|---|---|---|
| Δ24H25D | 17 | 43 |
| Δ24H25Q | 18 | 44 |
| Δ24H25V | 19 | 45 |
| Δ24H25K | 20 | 46 |
| Δ24F26D | 21 | 47 |
| Δ24F26Q | 22 | 48 |
| Δ24F26K | 23 | 49 |
| Δ24F26Y | 24 | 50 |
| FGF2$^{\Delta 24}$H25D-F26D | 25 | 51 |
| FGF2$^{\Delta 24}$H25D-F26Q | 26 | 52 |
| FGF2$^{\Delta 24}$H25D-F26K | 27 | 53 |
| FGF2$^{\Delta 24}$H25Q-F26D | 28 | 54 |
| FGF2$^{\Delta 24}$H25Q-F26K | 29 | 55 |
| FGF2$^{\Delta 24}$H25V-F26D | 30 | 56 |
| FGF2$^{\Delta 24}$H25V-F26Q | 31 | 57 |
| FGF2$^{\Delta 24}$H25V-F26K | 32 | 58 |
| FGF2$^{\Delta 24}$H25K-F26Q | 33 | 59 |

In some embodiments the isolated FGF variant polypeptide is an FGF4 variant. In certain embodiment the isolated FGF4 variant polypeptide retains from between 8 to 11 amino acid residues at the N-terminus extending beyond the LYC motif of the β1 strand of the core domain. The FGF4 variant polypeptides may further comprise a Met residue at the N-terminus.

In some embodiments the N-terminal truncated polypeptide is an FGF4 variant polypeptide selected from the group set forth in any one of SEQ ID NO:63-65. Variant sequences SEQ ID NO:60-62 have a similar activity to that of the FGF4 wild type, SEQ ID NO:67-68 are provided for comparison.

SEQ ID NO:60, representing FGF4$^{\Delta 72}$, has a 71 amino acid N-terminal truncation with the Gly72 replaced by a Met residue. This polypeptide is encoded by a polynucleotide sequence set forth in SEQ ID NO:69. The expressed FGF4$^{\Delta 72}$ polypeptide has a 13 amino acid N-terminal sequence preceding the LYC motif of the β1 strand of the core domain. The sequence may further comprise a Met residue at the N-terminus.

SEQ ID NO:61, representing FGF4$^{\Delta 73}$, has a 72 amino acid N-terminal truncation with the Ala73 replaced by a Met residue. This polypeptide is encoded by a polynucleotide sequence set forth in SEQ ID NO:70. The expressed FGF4$^{\Delta 73}$ polypeptide has a 12 amino acid N-terminal sequence preceding the LYC motif of the β1 strand of the core domain. The sequence may further comprise a Met residue at the N-terminus.

SEQ ID NO:62, representing FGF4$^{\Delta 74}$, has a 73 amino acid N-terminal truncation with the Gly74 replaced by a Met residue. This polypeptide is encoded by a polynucleotide sequence set forth in SEQ ID NO:71. The expressed FGF4$^{\Delta 74}$ polypeptide has an 11 amino acid N-terminal sequence preceding the LYC motif of the β1 strand of the core domain. The sequence may further comprise a Met residue at the N-terminus.

SEQ ID NO:63, representing FGF4$^{\Delta75}$, has a 74 amino acid N-terminal truncation with the Asp75 replaced by a Met residue. This polypeptide is encoded by a polynucleotide sequence set forth in SEQ ID NO:72. The expressed FGF4$^{\Delta72}$ polypeptide has a 10 amino acid N-terminal sequence preceding the LYC motif of the β1 strand of the core domain. The sequence may further comprise a Met residue at the N-terminus.

SEQ ID NO:64, representing FGF4$^{\Delta76}$, has a 75 amino acid N-terminal truncation with the Tyr76 replaced by a Met residue. This polypeptide is encoded by a polynucleotide sequence set forth in SEQ ID NO:73. The expressed FGF4$^{\Delta76}$ polypeptide has a 9 amino acid N-terminal sequence preceding the LYC motif of the β1 strand of the core domain. The sequence may further comprise a Met residue at the N-terminus.

SEQ ID NO:65, representing FGF4$^{\Delta77}$, has a 76 amino acid N-terminal truncation with the Leu77 replaced by a Met residue. This polypeptide is encoded by a polynucleotide sequence set forth in SEQ ID NO:74. The expressed FGF4$^{\Delta77}$ polypeptide has an 8 amino acid N-terminal sequence preceding the LYC motif of the β1 strand of the core domain. The sequence may further comprise a Met residue at the N-terminus.

SEQ ID NO:66 representing FGF4$^{\Delta78}$, has a 77 amino acid N-terminal truncation with the Leu78 replaced by a Met residue. This polypeptide is encoded by a polynucleotide sequence set forth in SEQ ID NO:75. The expressed FGF4$^{\Delta78}$ polypeptide has a 7 amino acid N-terminal sequence preceding the LYC motif of the β1 strand of the core domain. The sequence may further comprise a Met residue at the N-terminus. The truncated FGF4$^{\Delta78}$ polypeptide sequence has been disclosed in Bellosta et al., (2001) but according to the published data, exhibited binding affinities similar to that of the wild type ligand.

SEQ ID NO:67 representing FGF4$^{\Delta79}$, has a 78 amino acid N-terminal truncation with the Gly79 replaced by a Met residue. This polypeptide is encoded by a polynucleotide sequence set forth in SEQ ID NO:76. The expressed FGF4$^{\Delta79}$ polypeptide has a 6 amino acid N-terminal sequence preceding the LYC motif of the β1 strand of the core domain. The sequence may further comprise a Met residue at the N-terminus.

SEQ ID NO:68 representing FGF4$^{\Delta80}$, has a 79 amino acid N-terminal truncation with the Ile80 replaced by a Met residue. This polypeptide is encoded by a polynucleotide sequence set forth in SEQ ID NO:77. The expressed FGF4$^{\Delta78}$ polypeptide has a 5 amino acid N-terminal sequence preceding the LYC motif of the β1 strand of the core domain. The sequence may further comprise a Met residue at the N-terminus.

The sequence identifier numbers can be found hereinbelow in Table III.

TABLE III

| FGF4 variant and their associated sequence identifiers. | | |
|---|---|---|
| | SEQ ID NO: POLYPEPTIDE | SEQ ID NO: POLYNUCLEOTIDE |
| FGF4$^{\Delta72}$ | 60 | 69 |
| FGF4$^{\Delta73}$ | 61 | 70 |
| FGF4$^{\Delta74}$ | 62 | 71 |
| FGF4$^{\Delta75}$ | 63 | 72 |
| FGF4$^{\Delta76}$ | 64 | 73 |
| FGF4$^{\Delta77}$ | 65 | 74 |
| FGF4$^{\Delta78}$ | 66 | 75 |

TABLE III-continued

| FGF4 variant and their associated sequence identifiers. | | |
|---|---|---|
| | SEQ ID NO: POLYPEPTIDE | SEQ ID NO: POLYNUCLEOTIDE |
| FGF4$^{\Delta79}$ | 67 | 76 |
| FGF4$^{\Delta80}$ | 68 | 77 |

According to certain embodiments the N-terminal truncated FGF is an FGF4 polypeptide variant having amino acid sequence selected from any one of SEQ ID NO:63-65. According to another aspect the present invention provides a polynucleotide molecule whose sequence encodes an N-terminal FGF4 variant polypeptide of the invention, the polynucleotide sequence set forth in any one of SEQ ID NOS:72-74.

In a second aspect the present invention provides an isolated polynucleotide sequence encoding a variant polypeptide of a fibroblast growth factor selected from the group consisting of FGF2 and FGF4 comprising an N-terminal deletion; wherein the variant polypeptide retains between 0 and 11 amino acid residues at the N-terminus extending beyond the LYC motif of the β1 strand of the core domain; and wherein the variant polypeptide has increased receptor selectivity when compared to the corresponding wild type FGF polypeptide by a gain of activity or loss of activity by at least a factor of two toward at least one receptor subtype but not toward all FGFR subtypes.

In one aspect the present invention provides a vector comprising the polynucleotide sequences set forth in any one of SEQ ID NOS:34-59 or SEQ ID NOS:69-74 or SEQ ID NOS:76-77. According to some embodiments the present invention provides a vector comprising any one of polynucleotide sequences set forth in any one of SEQ ID NOS:36-42, SEQ ID NOS:43-49, SEQ ID NOS:51-59, SEQ ID NOS:72-74.

In another aspect, the present invention provides a host cell comprising a vector, the vector comprising a sequence set forth in any one of SEQ ID NOS:34-42 or SEQ ID NOS:43-59 or SEQ ID NOS:69-74 or SEQ ID NOS:76-77. According to some embodiments the present invention provides a host cell comprising a vector, the vector comprising any one of polynucleotide sequences set forth in any one of SEQ ID NOS:36-42, SEQ ID NOS:43-49, SEQ ID NOS:51-59 or SEQ ID NOS:72-74.

In another aspect the present invention provides a pharmaceutical composition comprising as an active ingredient an isolated N-terminal modified fibroblast growth factor polypeptide selected from FGF2 and FGF4. Accordingly the present invention provides an isolated variant polypeptide of a fibroblast growth factor selected from the group consisting of FGF2 and FGF4 comprising an N-terminal deletion; wherein the variant polypeptide retains between 0 and 11 amino acid residues at the N-terminus extending beyond the LYC motif of the β1 strand of the core domain; and wherein the variant polypeptide has increased receptor selectivity when compared to the corresponding isolated wild type FGF polypeptide by a gain of activity or loss of activity by at least a factor of two toward at least one receptor subtype but not toward all FGFR subtypes; and a pharmaceutically acceptable diluent or carrier.

According to another aspect the present invention provides a pharmaceutical composition comprising a therapeutic amount of at least one isolated polynucleotide sequence encoding an isolated variant FGF2 polypeptide comprising an N-terminal deletion; wherein the variant polypeptide retains between 0 and 5 amino acid residues at the N-terminus extending beyond the LYC motif of the β1 strand of the core domain; and wherein the variant polypeptide has increased receptor selectivity when compared to the corresponding isolated wild type FGF2 polypeptide by a gain of activity or loss of activity by at least a factor of two toward at least one receptor subtype but not toward all FGFR subtypes, and a pharmaceutically acceptable diluent or carrier. According to one embodiment the pharmaceutical composition comprises at least one polypeptide sequence having an amino acid sequence set forth in any one of SEQ ID NO:7-12, SEQ ID NO:17-23 or SEQ ID NO:25-33; and a pharmaceutically acceptable carrier, diluent or excipient. In some embodiments the pharmaceutical composition comprises a polypeptide having amino acid sequence set forth in SEQ ID NO:7.

According to another aspect the present invention provides a pharmaceutical composition comprising a therapeutic amount of an isolated polynucleotide sequence encoding an isolated variant FGF4 polypeptide comprising an N-terminal deletion; wherein the variant polypeptide retains between 8 and 11 amino acid residues at the N-terminus extending beyond the LYC motif of the β1 strand of the core domain; and wherein the variant polypeptide has increased receptor selectivity when compared to the corresponding isolated wild type FGF4 polypeptide by a gain of activity or loss of activity by at least a factor of two toward at least one receptor subtype but not toward all FGFR subtypes, and a pharmaceutically acceptable diluent or carrier. According to one embodiment the pharmaceutical composition comprises at least one polypeptide sequence having an amino acid sequence set forth in any one of SEQ ID NO:63-65; and a pharmaceutically acceptable carrier, diluent or excipient.

According to another aspect a single point mutation at the N-terminus has been found advantageous in terms of receptor selectivity, even without N-terminal truncation. According to another embodiment the FGF variant is an FGF2 polypeptide variant having amino acid sequence set forth in SEQ ID NO:90. In a specific embodiment the present invention provides an isolated polynucleotide sequence set forth in SEQ ID NO:91. In a specific embodiment the present invention provides a vector comprising the polynucleotide sequence set forth in SEQ ID NO:91. In another embodiment the present invention provides a pharmaceutical composition comprising as an active ingredient the isolated N-terminal modified fibroblast growth factor polypeptide set forth in SEQ ID NO:90. According to another embodiment the present invention provides a pharmaceutical composition comprising a therapeutic amount of the isolated polynucleotide sequence set forth in SEQ ID NO:91.

In some embodiments the pharmaceutical composition of the present invention is formulated for administration via intra-articular, intravenous, intramuscular, subcutaneous, intradermal, or intrathecal routes. In certain embodiments the pharmaceutical composition is formulated for administration to the site of a bone fracture or cartilage lesion. In other embodiment the pharmaceutical composition is formulated for application to a wound.

In another aspect the present invention provides a method of treating an individual in need thereof comprising the step of administering to that individual a pharmaceutical composition according to the present invention. The present invention includes methods of treating a subject with a wound, a bone disorder, a cartilage disorder. In other embodiments the present invention provides a method of treating a subject with coronary and peripheral vascular disease. These methods of treatment the abovementioned disorders or diseases comprise the administration of any of the following sequences set forth in SEQ ID NOS: 7-13, SEQ ID NOS: 17-23, SEQ ID NOS: 25-33, SEQ ID NOS: 63-65, and their corresponding nucleotides in SEQ ID NOS: 36-42, SEQ ID NOS: 43-49, SEQ ID NOS: 51-59 and SEQ ID NOS: 72-74.

In another embodiment the present invention provides a method of treating a subject with a wound, a bone disorder, a cartilage disorder, a coronary and peripheral vascular disease with the administration of a polypeptide having an amino acid sequence set forth in SEQ ID NO:66, or its corresponding polynucleotide having a sequence set forth in SEQ ID NO:75.

In yet another aspect the present invention provides a method of inducing cellular expansion, comprising the steps of:
  a. isolating a population of cells to be expanded; and
  b. exposing said cells to an N-terminal FGF polypeptide variant according to the present invention.

In some embodiments the population of cells to be expanded comprises hematopoietic cells. In other embodiments the population of cells to be expanded the cells are selected from stem cells or progenitor cells. Cells suitable for proliferation include cells selected from chondrocytes, osteoblasts, hepatocytes, fibroblasts or mesenchymal, endothelial, epithelial, urothelial, endocrine, neuronal, pancreatic, renal and ocular cell types.

In yet another aspect the present invention provides methods for the use of an isolated FGF polypeptide of the present invention to prepare medicaments useful for treating various diseases and disorders. In one embodiment the present invention provides the use of isolated FGF polypeptides of the present invention to prepare medicaments useful in bone and cartilage formation and regeneration, wound healing, neovascularization and treating FGFR related skeletal and proliferative disorders.

The isolated polypeptide variants of the present invention are useful for a variety of therapeutic applications including wound healing, induction of angiogenesis, tissue repair and tissue regeneration. It will be appreciated that the therapeutic methods of the invention the subject to be treated is preferably a mammal, more preferably a human.

The abbreviations used herein correspond to the one letter amino acid code followed by the number designating the amino acid position in the 155 aa form of FGF2 (SEQ ID NO:3), the 206 aa form of FGF4 (SEQ ID NO:4), and the one letter amino acid code for the substituted amino acid.

BRIEF DESCRIPTION OF THE FIGURES

FIG. 1A. The amino acid residues comprising the core domains of human FGF2 (SEQ ID NO:1) and human FGF4 (SEQ ID NO:2). FIG. 1B. Human FGF2 polypeptide sequence and N-terminal variants. Arrows indicate the penultimate amino acid of FGF2$^{\Delta24}$, FGF2$^{\Delta25}$, FGF2$^{\Delta26}$ and FGF2$^{\Delta31}$. FIG. 1C. Human FGF4 polypeptide sequence and N-terminal variants. An arrow indicates the penultimate amino acid of FGF4$^{\Delta78}$.

3A), while exhibiting reduced activity towards FGFR2 (FIG. 3B) and FGFR3 (FIG. 3C) in comparison to wild-type (diamonds) activity. FDCP cells were incubated 2 days with the wild-type FGF2 or FGF2$^{\Delta 26}$ ligands and cell proliferation was measured by XTT.

Figure 4:
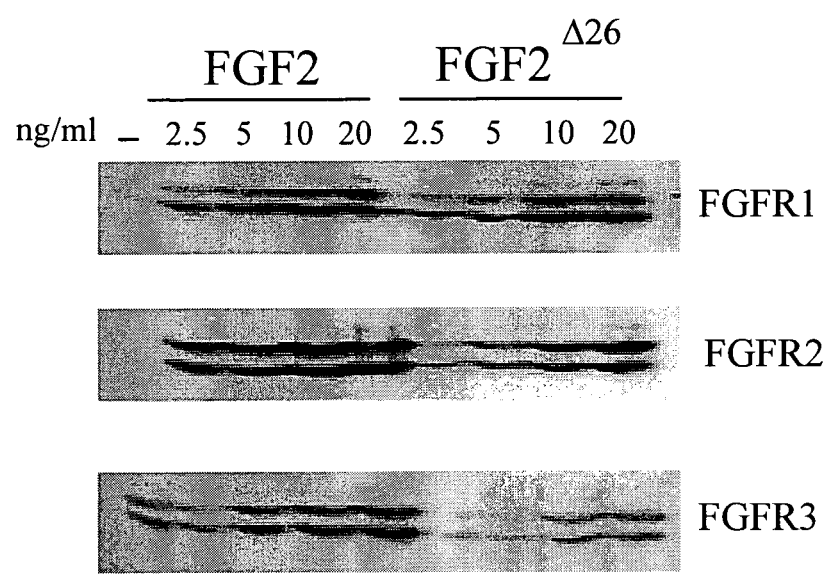

FIG. 4. RCJ cells expressing one of FGFR1, FGFR2 or FGFR3 were incubated for 5 minutes with FGF2 or FGF2$^{\Delta 26}$. Whole cell lysates were then analyzed by Western blot analysis using an anti-phosphorylated ERK (MAPK) antibody.

Figure 5A:
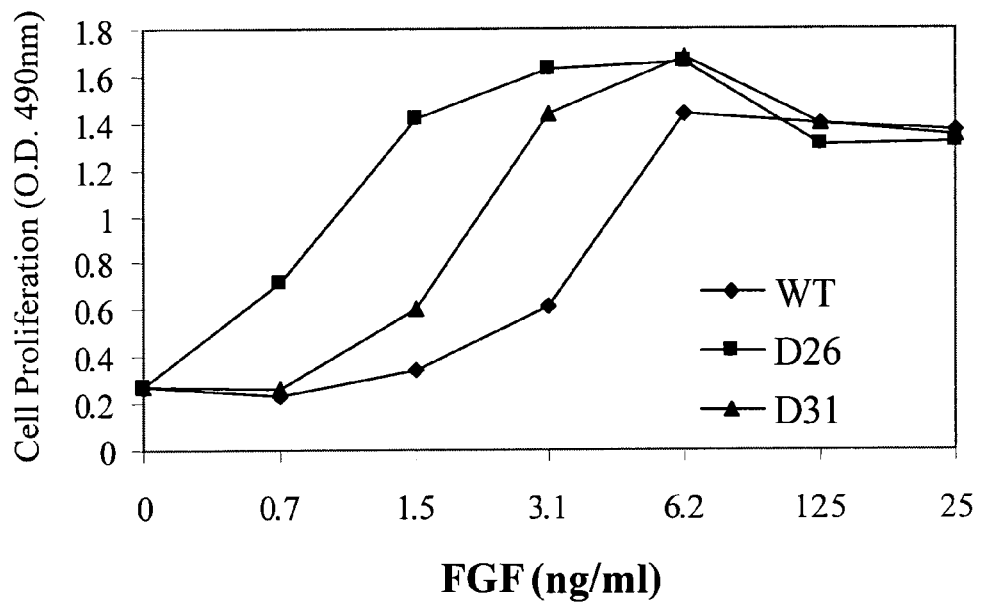
Figure 5B:
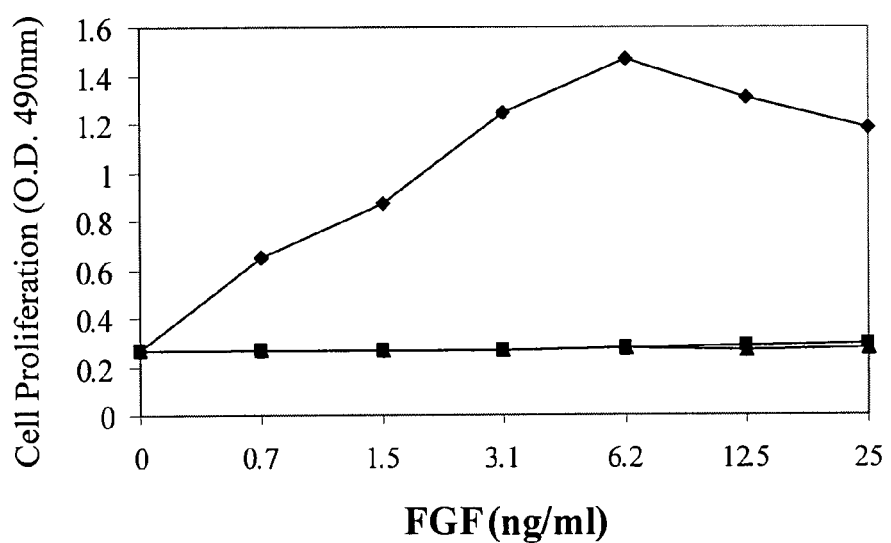

FIGS. 5A-5B. FGFR1 selectivity of N-terminal truncated FGF2 variants in FDCP cells. FDCP cells expressing FGFR1 (FIG. 5A) or FGFR3 (FIG. 5B) were stimulated with increasing amount of wild-type (FGF2; diamonds), FGF2$^{\Delta 26}$ (squares) or FGF2$^{\Delta 31}$ (triangles). The resulting cell proliferation was measured by XTT.

Figure 6A:
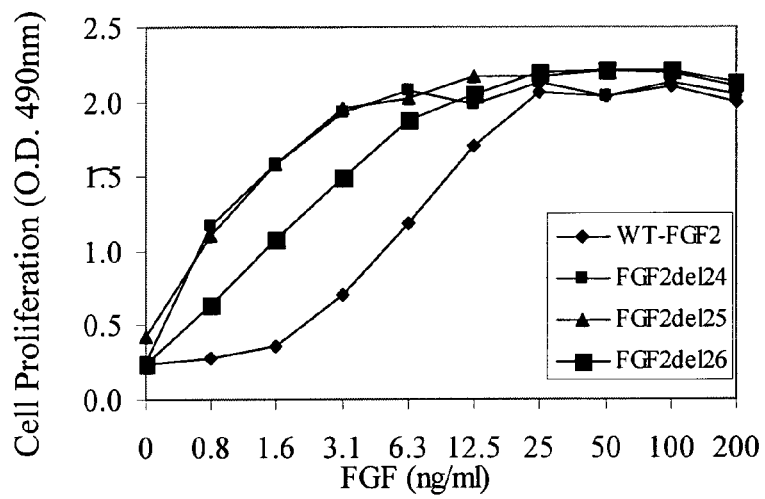
Figure 6B:
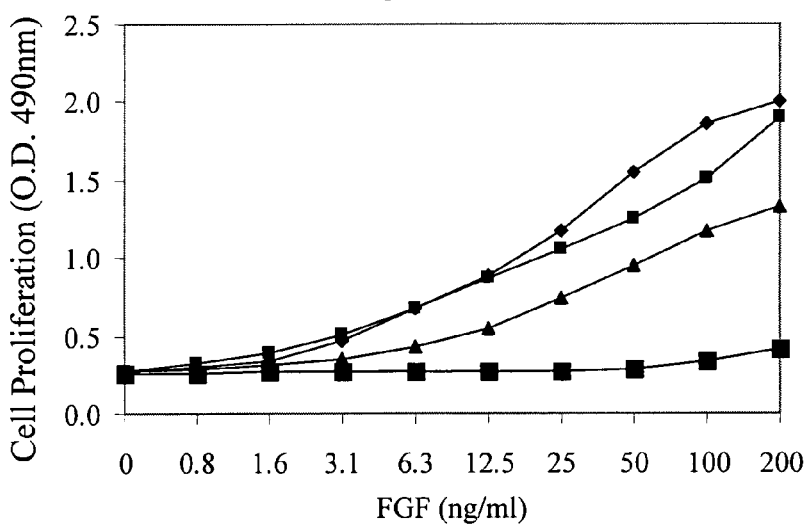
Figure 6C:
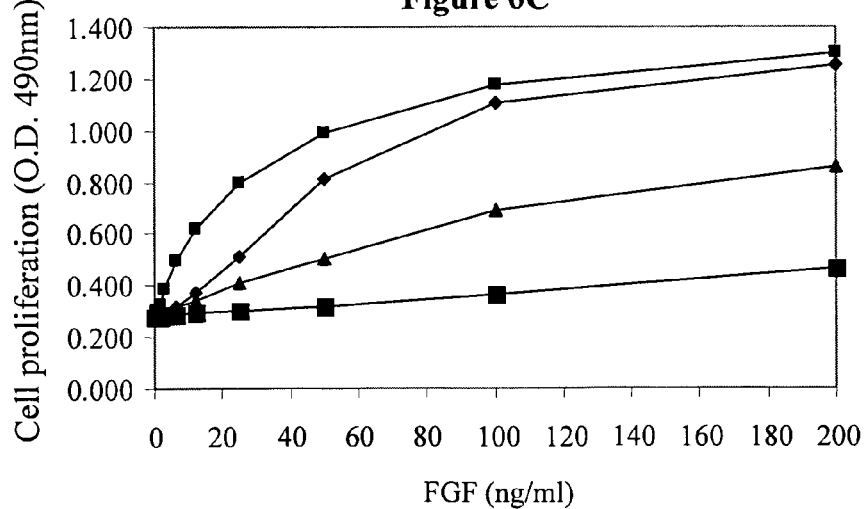
Figure 11A:
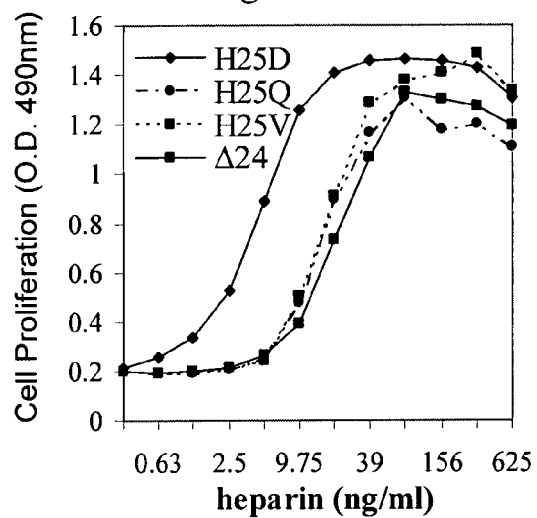
Figure 11B:
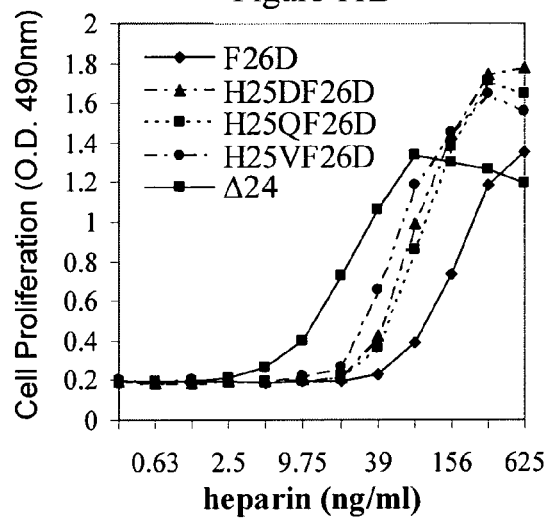
Figure 11C:
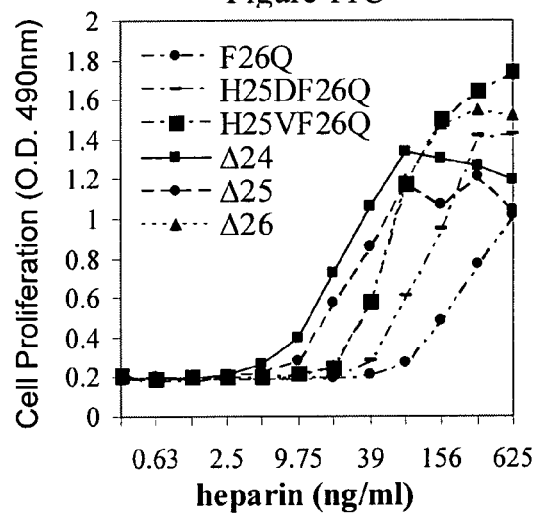
Figure 11D:
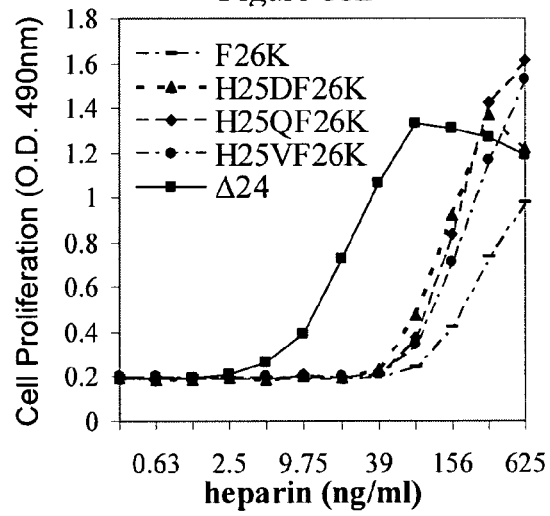

FIGS. 6A-6C. The activity of the N-terminal truncated variants FGF2$^{\Delta 24}$ (small squares), FGF2$^{\Delta 25}$ (triangles) and FGF2$^{\Delta 26}$ (large squares) compared to activity of wild-type FGF2 (diamonds) on FGFR1 (FIG. 6A), FGFR3 (FIG. 6B) and FGFR4 (FIG. 6C). Cell proliferation at the indicated dose of each ligand was measured by XTT analysis.

FIGS. 7A-7N. Activation of FGFR1 by N-terminal truncated FGF2 variants having substitutions at amino acid residues 25 and 26. FDCP-FGFR1 cells were cultured with increasing levels of FGF2 mutants for 2 days. Then, cell proliferation was measured by XTT analysis. Wild-type FGF2 (squares), FGF2$^{\Delta 24}$ (denoted D24; diamonds), FGF2$^{\Delta 25}$ (denoted D25; rectangles) and FGF2$^{\Delta 26}$ (denoted D26; circles) were included in the assay as controls. The following variants (triangles) are compared to the controls at each figure in the following manner: FGF2$^{\Delta 24H25D}$ (FIG. 7A), FGF2$^{\Delta 24H25Q}$ (FIG. 7B), FGF2$^{\Delta 24H25V}$ (FIG. 7C), FGF2$^{\Delta 24F26D}$ (FIG. 7D), FGF2$^{\Delta 24F26Q}$ (FIG. 7E), FGF2$^{\Delta 24F26K}$ (FIG. 7F), FGF2$^{\Delta 24H25DF26D}$ (FIG. 7G), FGF2$^{\Delta 24H25DF26Q}$ (FIG. 7H), FGF2$^{\Delta 24H25DF26K}$ (FIG. 7I), FGF2$^{\Delta 24H25QF26D}$ (FIG. 7J), FGF2$^{\Delta 24H25QF26K}$ (FIG. 7K), FGF2$^{\Delta 24H25VF26D}$ (FIG. 7L), FGF2$^{\Delta 24H25VF26Q}$ (FIG. 7M), FGF2$^{\Delta 24H25VF26K}$ (FIG. 7N). The data are average of duplicate cultures.

FIGS. 8A-8N. Activation of FGFR2 by N-terminal truncated FGF2 variants having substitutions at residues 25 and 26. FDCP-FGFR2 cells were cultured with increasing levels of FGF2 mutants for 2 days. Then, cell proliferation was measured by XTT analysis. Wild-type FGF2 (squares), FGF2$^{\Delta 24}$ (diamonds), FGF2$^{\Delta 25}$ (rectangles) and FGF2$^{\Delta 26}$ (circles) were included in the assay as controls. The following variants (triangles) are compared to the controls at each figure in the following manner: FGF2$^{\Delta 24H25D}$ (FIG. 8A), FGF2$^{\Delta 24H25Q}$ (FIG. 8B), FGF2$^{\Delta 24H25V}$ (FIG. 8C), FGF2$^{\Delta 24F26D}$ (FIG. 8D), FGF2$^{\Delta 24F26Q}$ (FIG. 8E), FGF2$^{\Delta 24F26K}$ (FIG. 8F), FGF2$^{\Delta 24H25DF26D}$ (FIG. 8G), FGF2$^{\Delta 24H25DF26Q}$ (FIG. 8H), FGF2$^{\Delta 24H25DF26K}$ (FIG. 8I), FGF2$^{\Delta 24H25QF26D}$ (FIG. 8J), FGF2$^{\Delta 24H25QF26K}$ (FIG. 8K), FGF2$^{\Delta 24H25VF26D}$ (FIG. 8L), FGF2$^{\Delta 24H25VF26Q}$ (FIG. 8M), FGF2$^{\Delta 24H25VF26K}$ (FIG. 8N). The data are average of duplicate cultures.

FIGS. 9A-9J. Activation of FGFR3 by N-terminal truncated FGF2 variants having substitutions at residues 25 and 26. FDCP-FGFR3 cells were cultured with increasing levels of FGF2 variants for 2 days. Then, cell proliferation was measured by XTT analysis. As controls, wild-type FGF2, FGF2$^{\Delta 24}$, FGF2$^{\Delta 25}$ and FGF2$^{\Delta 26}$ were included in the assay. The following variants are compared to the FGF2 wild-type (squares) in the following manner: FGF2$^{\Delta 24H25D}$ (diamonds), FGF2$^{\Delta 24H25Q}$ (triangles) and FGF2$^{\Delta 24H25V}$ (circles) in FIG. 9A; FGF2$^{\Delta 24F26D}$ (triangles) in FIG. 9B; FGF2$^{\Delta 24F26Q}$ (diamonds) and FGF2$^{\Delta 24F26K}$ (circles) in FIG. 9C; FGF2$^{\Delta 24H25DF26D}$ (triangles), FGF2$^{\Delta 24}$ (diamonds), FGF2$^{\Delta 25}$ (rectangles) and FGF2$^{\Delta 26}$ (circles) in FIG. 9D; FGF2$^{\Delta 24H25DF26Q}$ (diamonds) and FGF2$^{\Delta 24H25DF26K}$ (circles) in FIG. 9E; FGF2$^{\Delta 24H25QF26D}$ (circles) in FIG. 9F; FGF2$^{\Delta 24H25QF26K}$ (triangles) in FIG. 9G; FGF2$^{\Delta 24H25VF26D}$ (triangles) in FIG. 9H; FGF2$^{\Delta 24H25VF26Q}$ (circles) in FIG. 9I; and FGF2$^{\Delta 24H25VF26K}$ (triangles) in FIG. 9J. The data are average of duplicate cultures.

FIGS. 10A-10J. Activation of FGFR4 by N-terminal truncated FGF2 variants having substitutions at residues 25 and 26. FDCP-FGFR4 cells were cultured with increasing levels of FGF2 variants for 2 days. Then, cell proliferation was measured by XTT analysis. As controls, wild-type FGF2, FGF2$^{\Delta 24}$, FGF2$^{\Delta 25}$ and FGF2$^{\Delta 26}$ were included in the assay. It is noteworthy that all substitutions which appear in the figure are in addition to a Δ24 N-terminal truncation. The data are average of duplicate cultures.

FIGS. 11A-11D. Heparin dependent activation of FGFR1 by N-terminal truncated FGF2 variants having substitutions at residues 25 and 26. FDCP-FGFR1 cells were incubated with 1.5 ng/ml of the indicated FGF2 mutants at limiting heparin levels and cell proliferation was measured by XTT analysis. It is noteworthy that all substitutions which appear in the figure are in addition to a Δ24 N-terminal truncation.

Figure 12A:
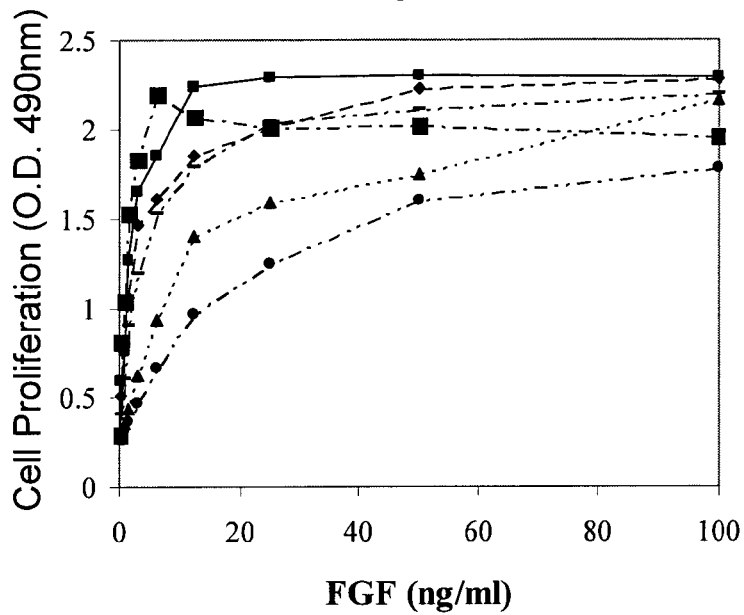
Figure 12B:
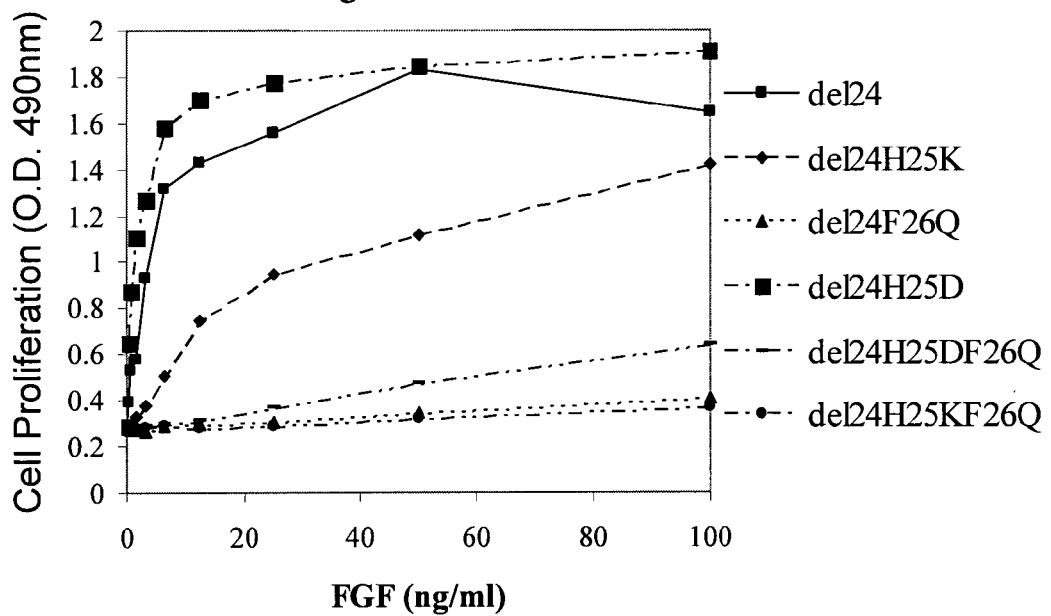

FIGS. 12A-12B. Activation of FGFR1 (FIG. 12A) and FGFR3 (FIG. 12B) by FGF2 N-terminal truncated variants at residues 25 and/or 26. N-terminal truncated FGF2 with the indicated replacement at position 25 and/or 26 were added at increasing concentrations to FDCP-FGFR1 or FDCP-FGFR3 cells. The variants are denoted as follows: FGF2$^{\Delta 24}$ (small squares), FGF2$^{\Delta 24H25K}$ (diamonds), FGF2$^{\Delta 24F26Q}$ (triangles), FGF2$^{\Delta 24H25D}$ (large squares), FGF2$^{\Delta 24H25DF26Q}$ (rectangles), and FGF2$^{\Delta 24H25KF26Q}$ (circles). Cell proliferation (average of duplicate cultures) was measured 2 days later by XTT analysis.

FIGS. 13A-13F. Activity of FGF2$^{F26Q}$ under saturating (FIGS. 13A-13C), or limiting (FIGS. 13D-13F) heparin concentrations. FDCP-FGFR1 (FIGS. 13A, 13D), FDCP-FGFR2 (FIGS. 13B, 13E) or FDCP-FGFR3 (FIGS. 13C, 13F) cells were cultured with increasing FGF2 (squares) or FGF2$^{F26Q}$ (diamonds) levels under saturating (5 μg/ml) or limiting (20 ng/ml) heparin concentrations. Cell proliferation was measured after 2 days by XTT. Data are average of 2 cultures+/−SD.

FIGS. 14A-14C. Activity of FGF2$^{\Delta 24F26Y}$ on FDCP-FGFR1 (FIG. 14A), FDCP-FGFR2 (FIG. 14B) and FDCP-FGFR3 (FIG. 14C). FGF2$^{\Delta 24F26Y}$ (circles), FGF2$^{\Delta 24F26Q}$ (squares) or FGF2$^{\Delta 24}$ (diamonds) were added at increasing amounts to FDCP-FGFR1, FDCP-FGFR2 and FDCP-FGFR3 cells. Cell proliferation was evaluated 2 days later by XTT analysis.

Figure 15:
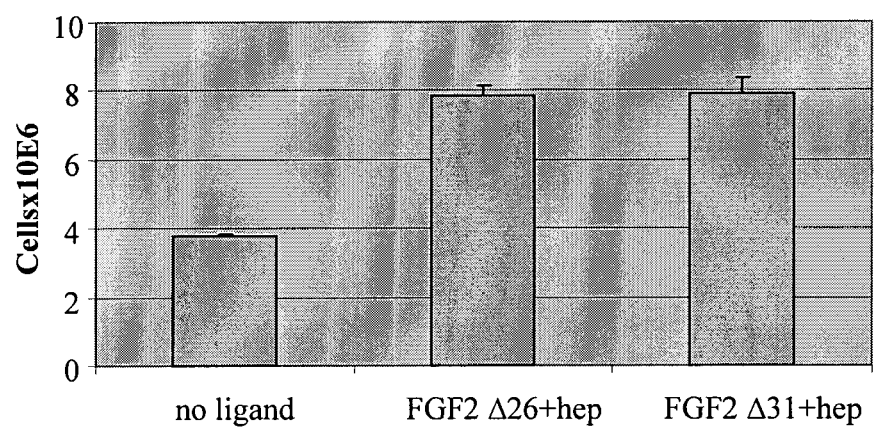

FIG. 15. Effect of N-terminal truncated FGF2 variants on primary human articular chondrocytes proliferation. Primary human articular chondrocytes were isolated from cartilage piece and expanded for 10 days in DMEM/F12, 20% human serum and 10 ng/ml of FGF2$^{\Delta 26}$ or FGF2$^{\Delta 31}$+ heparin (5 μg/ml). Every 3 days medium was replaced. Cells were counted after 10 days.

Figure 16A:
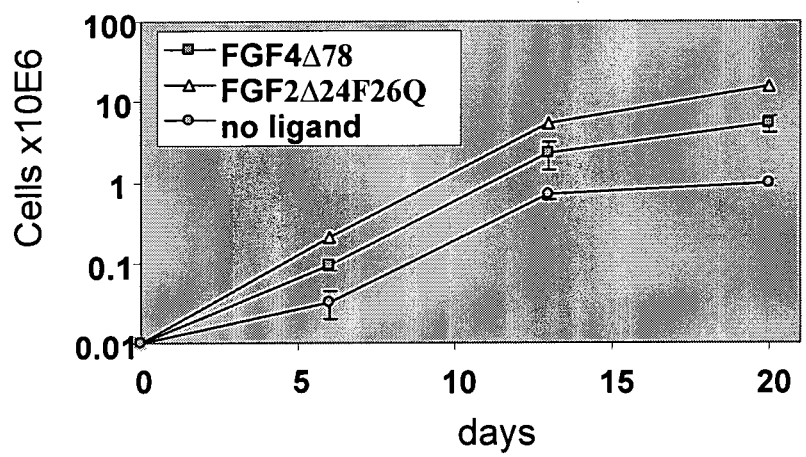
Figure 16B:
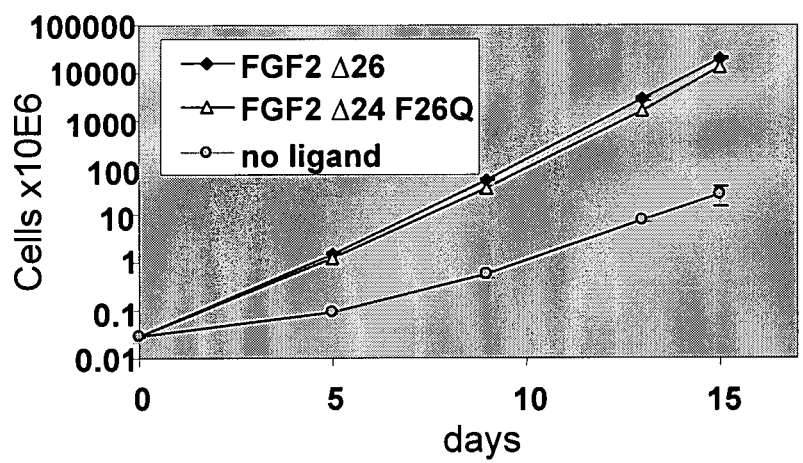

FIGS. 16A-16B. Effect of N-terminal truncated FGF2 and FGF4 variants on human bone marrow derived mesenchymal stem cells (hBM-MSC) proliferation. Samples of human bone marrow were seeded on 10 cm plates in DMEM-LG, 20% HS, and 5 μg/ml LMW Heparin and FGF4$^{\Delta 78}$/FGF2$^{\Delta 24F26Q}$/no ligand (FIG. 16A) or FGF2$^{\Delta 26}$/FGF2$^{\Delta 24F26Q}$/no ligand (FIG. 16B). After 6 days the cells were used for proliferation assay: 1-5×10⁴ cells were seeded in 24 wells plate and in several time points cells were counted and reseeded.

Figure 17:
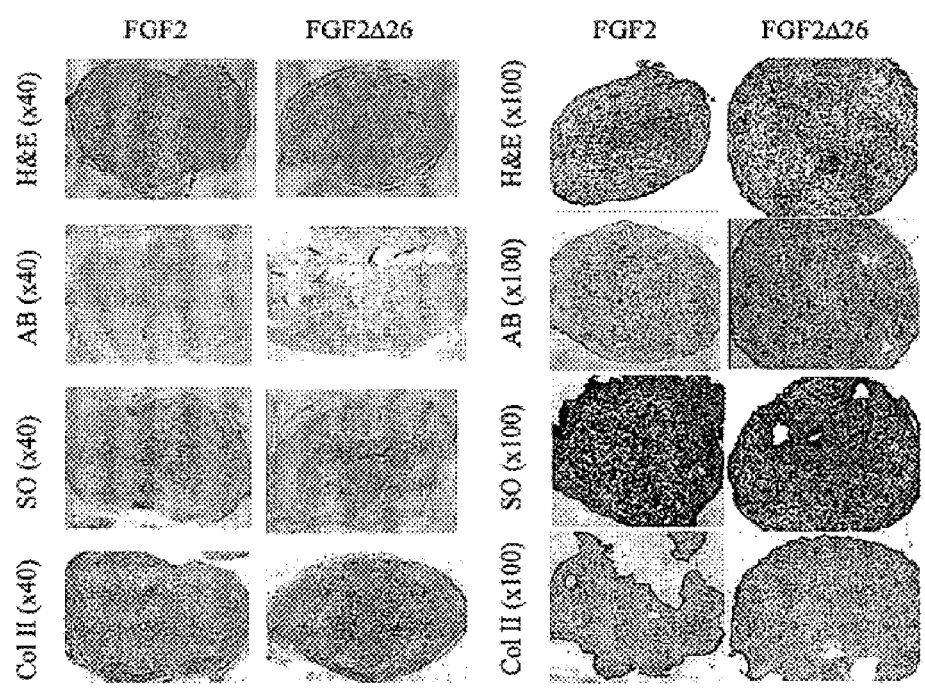

FIG. 17. Histology analysis of pellet cultures produced from hBM-MSC. Human BM-MSCs were expanded in DMEM-LG medium supplemented with 20% human serum and 10 ng/ml FGF2, or FGF2$^{\Delta 26}$+Heparin (5 µg/ml). Pellet culture assay was performed on the cells expanded for 10-14 days. The pellet cultures were incubated in differentiation medium for 21 days and histologically analyzed. Histology included hematoxylin eosin (H&E), Alcian blue (AB), and Safranin O (SO) and immunohistochemistry with anti-Collagen II antibodies (Col II).

Figure 18:
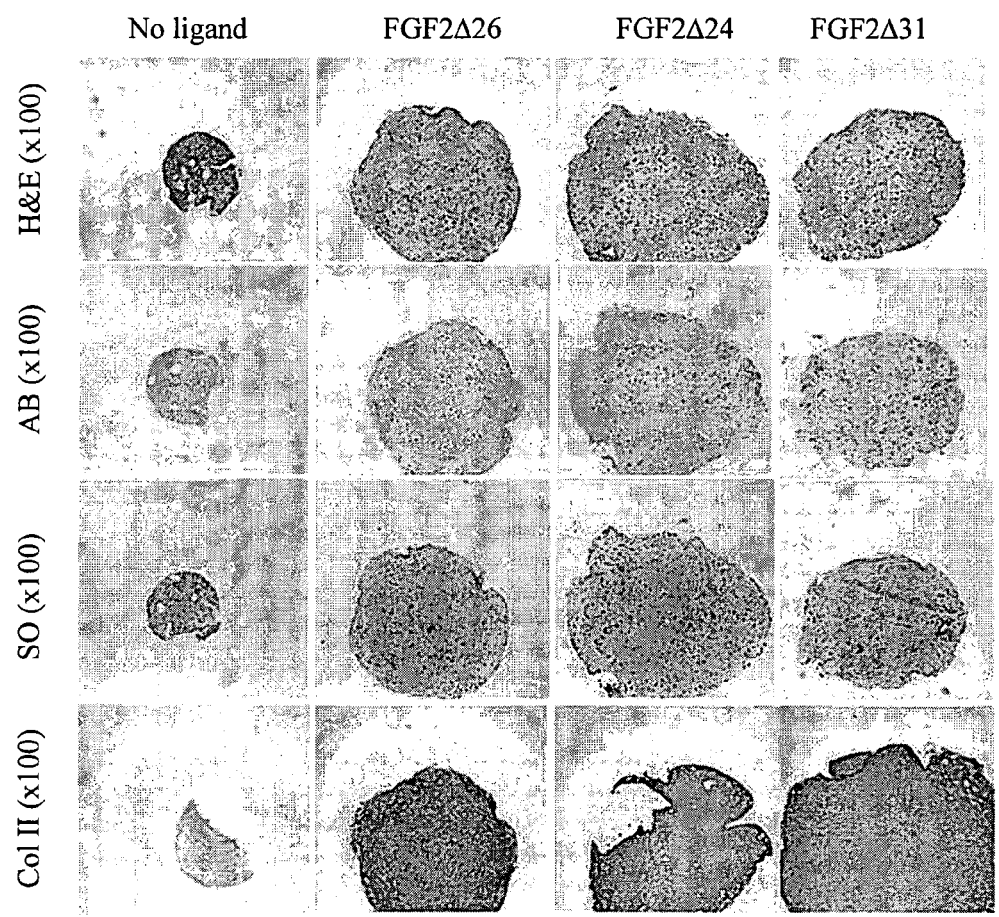

FIG. 18. Histology analysis of pellet cultures produced from hBM-MSC. Human BM-MSCs were expanded in DMEM-LG medium supplemented with 20% human serum and 10 ng/ml FGF2$^{\Delta 26}$, or FGF2$^{\Delta 24}$, or FGF2$^{\Delta 31}$+Heparin (5 µg/ml). Pellet culture assay was performed on the cells expanded for 14 days. The pellet cultures were incubated in differentiation medium for 21 days and histologically analyzed. Histology included hematoxylin eosin (H&E), Alcian blue (AB), and Safranin O (SO) and immunohistochemistry with anti-Collagen II antibodies (Col II).

Figure 19A:
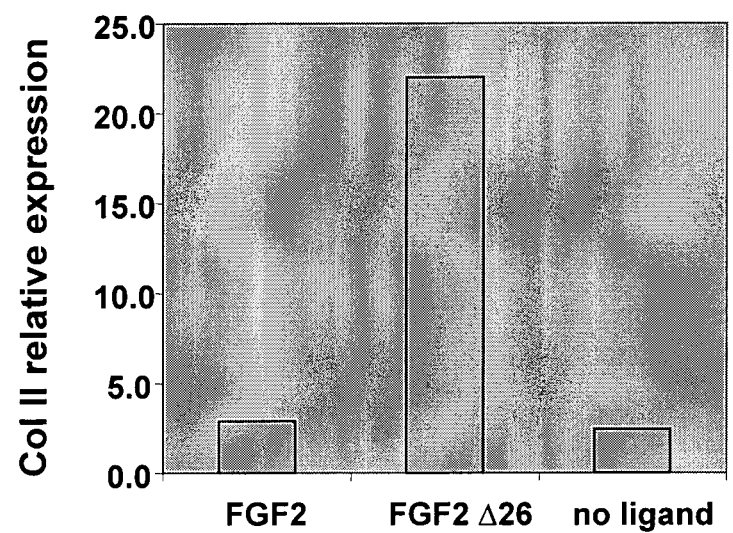
Figure 19B:
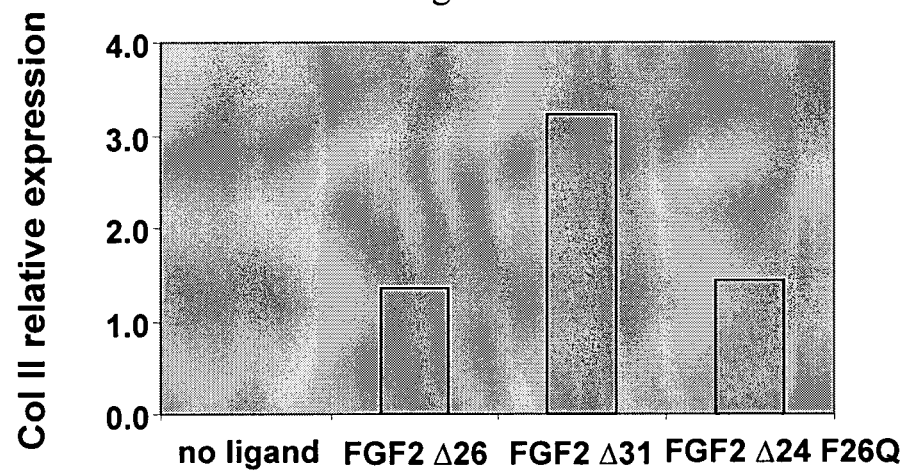

FIGS. 19A-19B. qPCR analysis of Col II in pellet culture produced from hBM-MSC expanded with FGF2, FGF2$^{\Delta 26}$ variant and with no ligand for comparison (FIG. 19A), or with FGF2$^{\Delta 26}$, FGF2$^{\Delta 31}$ and FGF2$^{\Delta 24F26Q}$ variants and with no ligand for comparison (FIG. 19B). Expression of Col II was analyzed by qPCR of RNA isolated from pellet culture produced from hBM-MSC expanded for 14 days.

Figure 20:
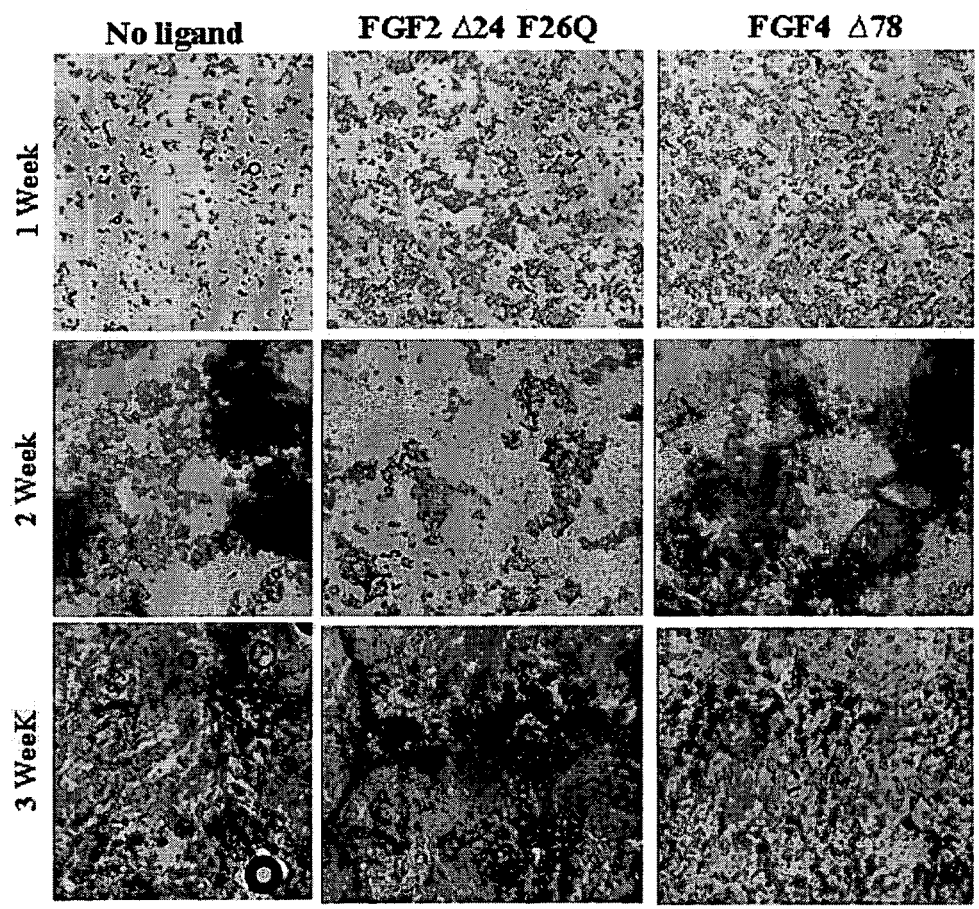

FIG. 20. In-vitro osteogenesis assay of hBM-MSC expanded in the presence of different ligands. Mesenchymal stem cells (MSC) isolated from human bone marrow sample were expanded for 14 days in MSC expansion medium containing 10 ng/ml FGF2$^{\Delta 24F26Q}$ or FGF4$^{\Delta 78}$ and 5 µg/ml heparin. The cells (1×10⁵ per well) were then seeded on 6 well plate and cultured for 1, 2 or 3 weeks in osteoblast differentiation medium (DMEM-HG, 10% FCS, 100 nM Dexamethasone, 0.05 mM Ascorbic acid, 10 mM β-glycerolphosphate).

DETAILED DESCRIPTION OF THE INVENTION

According to the principles of the present invention, it is now disclosed that isolated FGF variant polypeptides of the present invention comprising amino acid truncations of the N-terminus adjacent to the β1 strand or extending into β1 strand of the core structure, while retaining the LYC motif, yield variants with improved properties, in addition to altered specificity to FGFRs. The variants thus obtained will have improved properties in terms of receptor specificity, stability and/or affinity in addition to enhanced mitogenic activity and/or differentiation potential. These variants may further comprise additional modifications providing variants with improved stability, solubility or yield.

Definitions

For convenience certain terms employed in the specification, examples and claims are described here.

The term "FGF2", also known as basic FGF, bFGF, prostatin and heparin binding growth factor 2, is highly conserved among species and has been shown to stimulate the proliferation of a wide variety of cell types. The sequence of FGF2 has been disclosed in U.S. Pat. Nos. 4,994,559; 5,155,214; 5,439,818 and 5,604,293. Human FGF2 is expressed in several forms, a 210 aa precursor, a 157 aa form, a 155 aa form, a 146 aa N-terminal truncated form and several others (reviewed in Bikfalvi et al., 1997). The 155 aa form serves as the template for the truncated polypeptides disclosed herein. FGF2$^{QQ}$ refers to an FGF2 ligand having wild type activity towards all FGF receptor subtypes. As it is essentially indistinguishable from the wild type it has been used as a reference in some experiments. FGF2$^{QQ}$ has amino acid substitutions of glutamine at positions 3 and 5 (Alanine 3 is replaced by glutamine, Ala3Gln; Serine 5 is replaced with glutamine, Ser5Gln).

Fibroblast growth factors (FGFs) constitute a large family of structurally related, heparin binding polypeptides, expressed in a wide variety of cells and tissues. Overall, the FGFs share between 17-72% amino acid sequence homology and a high level of structural similarity. A homology core of about 120 amino acids is highly conserved and has been identified in all members of the family. Twelve antiparallel strands have been identified in the core structure, labeled β1 through β12, linked one to another by loops of variable lengths, organized into a trefoil internal symmetry. FIG. 1 in Mohammadi et al. (2005) shows amino acid sequence alignment of the β-trefoil strands for FGF1 through FGF23.

The core domain of FGF2 extends from amino acid Lys30 to Lys154; the core domain of FGF4 extends from amino acids Arg84 to Leu206.

The term "the N-terminal domain" refers to the amino acid residues included in the N-terminus and adjacent to the β1 strand. The β1 strand of FGF2 consists of the amino acid sequence: KRLYCK (SEQ ID NO:92); the β1 strand of FGF4 consists of the amino acid sequence: RRLYCN (SEQ ID NO:93). The Leu-Tyr-Cys (LYC) amino acid motif is a constant feature of the β1 strand of all wild type FGF ligands. Most of the wild type FGF ligands have an LYC, LYS or LYT motif. As used herein and in the claims the term "beta1" or "β1" "β1 strand" refers to the most N-terminal antiparallel β strand of the core structure as disclosed herein. The β1 strand is adjacent to the N-terminal amino acid sequence.

As used herein and in the claims the terms "amino terminus" and "N-terminus" of a polypeptide may be used interchangeably. Similarly, the terms "carboxy terminus" and "C-terminus" may be used interchangeably.

The beta8-beta9 loop of FGF2 consists of amino acids LESNNYNTY (SEQ ID NO:94; See FIG. 1A, underlined and labeled sequence).

The FGF ligands with increased receptor selectivity are useful in the treatment of various pathological conditions including tissue repair and regeneration, wound and ulcer healing, bone and cartilage disorders, bone fracture healing, osteoporosis and other skeletal disorders. Other uses include remodeling cardiac tissue and improving cardiac function, in particular for new blood vessel growth thereby providing an alternative route for blood to bypass clogged and blocked arteries in the heart.

Variant polypeptides are useful as site-specific carriers for delivery and concentration of bioactive agents to cells, tissues, or organs in which a therapeutic effect is desired to be effected. These variants may be therapeutically beneficial for treating skeletal disorders, including but not limited to achondroplasia, and proliferative diseases including but not limited to multiple myeloma, transitional cell carcinoma (TCC) of the bladder, breast cancer and cervical carcinoma. The targeting polypeptides are fusion proteins, chimeric recombinants, hybrid proteins or conjugates.

For pharmaceutical use the FGF variants of the present invention are formulated for administration via intra-articular, intravenous, intramuscular, subcutaneous, intradermal, or intrathecal routes according to conventional methods of use. The dosage will be prescribed according to common regimes in the art, while taking into consideration variables such as: weight, age, location of injury, extent of injury etc. The pharmaceuticals will include FGF variants of the present invention in addition to a carrier, namely, saline, buffered saline, 5% dextrose in water and alike. Additional excipients which prolong the half-life or biological activity of the active ingredients might also be added, for instance: preservatives, solubilizers, buffering agents, hyaluronic acid, albumin etc. Other compounds which are known to increase the resistance to proteolitic degradation might also be added. The treatment is suitable for an acute injury as well as for a chronic condition requiring prolonged treatment.

For convenience certain terms employed in the specification, examples and claims are described here.

As used herein and in the claims the term "FGFR" denotes a receptor specific for FGF molecule(s), which is necessary for transducing the signal, exerted by FGF to the cell interior, typically comprising an extracellular ligand-binding domain, a single transmembrane helix, and a cytoplasmic domain that contains a tyrosine kinase activity. The term "FGFR" includes various isotypes of the receptors including soluble versions comprising the extracellular domain and lacking the transmembrane and kinase domains.

As used herein and in the claims the term "weak FGF" denotes an FGF molecule or variant which, after binding to an FGF receptor, elicits stimulation of mitogenesis at most half that of the same cells exposed to the wild type parent FGF molecule, as measured in cell based assays known in the art. "Inactive FGF" denotes the variant that elicits stimulation of mitogenesis at most one tens that of the same cells exposed to the wild type parent FGF molecule.

As used herein and in the claims the term "an isolated FGF polypeptide having increased receptor selectivity" denotes an isolated FGF polypeptide molecule, having either enhanced or reduced biological activity toward at least one but not all FGFR, compared to the corresponding wild type FGFR. The biological activity toward at least one receptor, but not all FGF receptors, is reduced or increased by a factor of at least two. In some embodiments the biological activity toward at least one receptor, but not all FGF receptors, is reduced or increased by a factor of at least four, at least five, at least seven or at least ten.

Biological activity can be measured by methods known in the art. In some embodiments biological activity is measured as cell proliferation and/or substrate phosphorylation.

The term "affinity" as used herein denotes the ability of a ligand or variant of said ligand to bind to a specific receptor. Modifications to a ligand that stabilize favorable conformation or enhance amino acid side chain interactions will result in increased receptor affinity while those, which destabilize favorable conformation or decrease amino acid side chain interactions will result in decreased receptor affinity. A competitive binding assay was established to determine the relative affinity of isolated FGF polypeptides compared to that of wild type parent FGF towards an FGF receptor.

As used herein the term "differentiation factor" refers to a substance, in particular a polypeptide, which determines the fate that a cell will acquire upon exposure to that substance, alone or in combination with other substances. In a non-limiting example, differentiation is determined by morphological and phenotypic changes or by biochemical or molecular changes.

As used herein the term "mitogen" or "proliferation factor" refers to a substance that induces an increase in the number of cells.

As used herein and in the claims the term "core", "core domain" or "core structure" denotes a region of homology of about 120 amino acids that is found in all native FGFs. Twenty eight amino acid residues are highly conserved and four are identical. Twelve structurally conserved anti-parallel β strands have been identified within the core domain in all the FGFs. The core domain further comprises the FGFR- and heparin-binding sites. Sequence alignment and location and length of the β strands for FGF-1 through FGF-23 is depicted in FIG. 1 of Mohammadi et al. (2005). The amino acid sequences of the core structure of FGF2 and FGF4 are depicted herein in FIG. 1A.

"Nucleic acid sequence" or "polynucleotide" as used herein refers to an oligonucleotide or nucleotide and fragments or portions thereof, and to DNA or RNA of genomic or synthetic origin, which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring, synthetic or recombinant molecules. The terms listed herein are not meant to limit the amino acid sequence to the complete, wild type amino acid sequence associated with the recited protein molecule.

The term "variant" as used herein refers to a polypeptide sequence that possesses some modified structural property of the wild type or parent protein. For example, the variant may be truncated at either the amino or carboxy terminus or both termini or may have one or more amino acids deleted, inserted and or substituted. The most preferred method for producing the variants is through recombinant DNA technologies, well known to those skilled in the art. For example, the variants may be prepared by Polymerase Chain Reaction (PCR) using specific primers for each of the truncated forms or the amino acid substitutions as disclosed herein below. The PCR fragments may be purified on an agarose gel and the purified DNA fragment may be cloned into an expression vector and transfected into host cells. The host cells may be cultured and the protein harvested according to methods known in the art.

As used herein, the term "polymerase chain reaction" ("PCR") refers to the methods of amplifying nucleic acids, as disclosed in U.S. Pat. Nos. 4,683,195; 4,683,202 and 4,965,188 hereby incorporated by reference.

The term "expression vector" and "recombinant expression vector" as used herein refers to a recombinant DNA molecule containing a desired coding sequence and appropriate nucleic acid sequences necessary for the expression of the operably linked coding sequence in a particular host organism. The expression vector may comprise sequences encoding heterologous domains including but not limited to protein detection, purification or cleavage sequences that may be fused at the N- or C-terminus to the desired coding sequence, to yield a fusion protein. The present invention encompasses expression vectors that are integrated into host cell genomes, as well as episomal vectors.

As used herein, the "amino acids" used in the invention are those that are natural, those that are available commercially or are available by routine synthetic methods. Certain amino acid residues may require special methods for incorporation into the peptide, and sequential, divergent or convergent synthetic approaches to the peptide sequence are useful in this invention. Natural coded amino acids and their derivatives are represented by either the one-letter code or three-letter codes according to IUPAC conventions. When there is no indication, the L isomer is used.

As used herein and in the claims a "bioactive agent" is any agent which is desired to be delivered to cells, tissues or organs for modulating or modifying cell function, including for therapeutic effects. In accordance with the present invention, bioactive agents include, but are not limited to, pharmaceutically active compounds or diagnostic compounds. These include, but are not limited to, peptides and peptide analogs, peptidomimetics, oligopeptides, proteins, apoproteins, glycoproteins, antigens and antibodies or antibody fragments thereto, receptors and other membrane proteins, aptamers, enzymes, coenzymes, enzyme inhibitors, amino acids and their derivatives, hormones, lipids, phospholipids, liposomes; toxins; tyrosine kinase inhibitors, photoreactive agents, antibiotics; analgesics and anti-inflammatory substances; antimicrobial agents; antihypertensive agents; antiviral agents; antihistamines; anti-cancer drugs including chemotherapeutic agents; tranquilizers; neuroprotective agents; antispasmodics; anti-Parkinson agents; vitamins. Other bioactive agents include nucleotides; oligonucleotides; polynucleotides; and their biologically functional analogs and derivatives; plasmids, cosmids, artificial chromosomes, other nucleic acid vectors; antisense polynucleotides including those substantially complementary to at least one endogenous nucleic acid; promoters; enhancers; inhibitors; other ligands for regulating gene transcription and translation.

"Bone defect" or "bone disorder" may result from mutation, fracture, from surgical intervention, from a proliferative disease such as multiple myeloma or metastases, of from dental or periodontal disease. By "cartilage defect" or "cartilage disorder" is meant cartilage that has been damaged by disease, injury or trauma. Contemplated are indications including rheumatoid arthritis, osteoarthritis and joint injuries.

Representative uses of the compounds of the present invention include: repair of bone defects and deficiencies, such as those occurring in closed, open and non-union fractures; prophylactic use in closed and open fracture reduction; promotion of bone and cartilage healing in plastic surgery; stimulation of bone ingrowth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; treatment of articular chondrocytes prior to transplantation and treatment of other skeletal disorders, such as age-related osteoporosis, post-menopausal osteoporosis, glucocorticoid-induced osteoporosis or disuse osteoporosis and arthritis. Certain variants may be useful in other tissue regeneration and repair indications, for example in liver, pancreas, nerve regeneration and repair. The compounds of the present invention are useful in repair of congenital, trauma-induced or surgical resection of bone (for instance, for cancer treatment), and in cosmetic surgery. Treatment includes direct application of the variants to the traumatized area or systemic therapy as well as treatment of cells ex vivo and in vitro for tissue engineering and tissue regeneration. Additionally the variants may be provided in cell therapy.

As used herein, the terms "fusion protein" or "chimera", "chimeric recombinant" or "hybrid" refer to a single polypeptide produced using host cells expressing a single polynucleotide encoding an isolated FGF polypeptide of the invention and a bioactive agent including a polypeptide, peptide or peptide analog contiguous and in open reading frame. Certain peptide linkers may separate the FGF and the bioactive polypeptide, peptide or peptide analog. The present invention provides a highly effective system for delivery of an activity-inducing moiety into a particular type or class of cells. The fusion proteins generated can be screened for the desired specificity and activity utilizing the methods set forth in the examples and by various routine procedures. As used herein, the term "conjugate" refers to a bioactive agent covalently bound to a carrier or targeting moiety. Certain variants of the invention provide carriers or targeting agents for bioactive agents. An FGF "targeting molecule" or "complex molecule" refers to an isolated FGF polypeptide of the invention linked to a bioactive agent.

Provided in the present invention are pharmaceutical compositions comprising an isolated FGF polypeptide and a bioactive agent as a fusion protein or alternatively an isolated FGF polypeptide conjugate comprising an isolated FGF polypeptide and a bioactive agent useful for FGF targeting. The present invention further provides methods for inhibiting proliferation of cells that express FGFRs comprising administering an FGF variant targeting composition to the cells. For example, the composition is administered in a therapeutically effective amount to a subject that has a tumor, wherein the tumor cells express specific FGFR.

FGF activity is conveniently determined using biological assays performed in-vitro, ex-vivo and in vivo. The assays are used to demonstrate the activity elicited upon binding of an FGF molecule to its receptors. The biological assays routinely used to test activities of variant FGFs include, but are not limited to, the following:

binding of variant FGFs to cloned FGF receptors expressed on immortalized cell lines, thereby eliciting a biological response including cell proliferation or inhibition of cell proliferation;

cell proliferation and differentiation in cell culture systems;

phosphorylation assays;

stimulation of bone growth in animal models of bone growth and cell cultures;

enhancement of cartilage repair in animal models of cartilage disease and trauma.

Polynucleotide Sequences

The present invention also provides for an isolated nucleic acid molecule, which comprises a polynucleotide sequence encoding the protein of the invention and a host cell comprising this nucleic acid molecule. Furthermore, also within the scope of the present invention is a nucleic acid molecule containing a polynucleotide sequence having at least 90% sequence identity, preferably about 95%, and more preferably about 97% identity to the above encoding nucleotide sequence as would well understood by those of skill in the art.

The invention also provides isolated nucleic acid molecules that hybridize under high stringency conditions to polynucleotides having SEQ ID NO:34-59 or SEQ ID NO:69-77 or SEQ ID NO:91 or the complement thereof. As used herein, highly stringent conditions are those which are tolerant of up to about 5-20% sequence divergence, preferably about 5-10%. Without limitation, examples of highly stringent (−10° C. below the calculated Tm of the hybrid) conditions use a wash solution of 0.1×SSC (standard saline citrate) and 0.5% SDS at the appropriate Ti below the calculated Tm of the hybrid. The ultimate stringency of the conditions is primarily due to the wash conditions, particularly if the hybridization conditions used are those which allow less stable hybrids to form along with stable hybrids. The wash conditions at higher stringency remove the less stable hybrids. A common hybridization condition that can be used with the highly stringent to moderately stringent wash conditions described above may be performed by hybridizing in a solution of 6×SSC (or 6×SSPE), 5×Denhardt's reagent, 0.5% SDS, 100 μg/ml denatured, fragmented salmon sperm DNA at an appropriate incubation temperature Ti. See generally Sambrook et al. (1989) for suitable high stringency conditions.

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization and hybridization duration. The hybridization rate is maximized at a Ti (incubation temperature) of 20-25° C. below Tm for DNA:DNA hybrids and 10-15° C. below Tm for DNA:RNA hybrids. It is also maximized by an ionic strength of about 1.5M Na$^+$. The rate is directly proportional to duplex length and inversely proportional to the degree of mismatching. Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA: DNA hybrids using the equation of Meinkoth, as $$Tm=81.5° C.+16.6(\log M)+0.41(\% GC)-0.61(\% \text{form})-500/L$$

and for DNA:RNA hybrids, as $$Tm=79.8° C.+18.5(\log M)+0.58(\% GC)-11.8(\% GC)^2-0.56(\% \text{form})-820/L$$

where

M, molarity of monovalent cations, 0.01-0.4 M NaCl,
% GC, percentage of G and C nucleotides in DNA, 30%-75%,
% form, percentage formamide in hybridization solution, and
L, length hybrid in base pairs.

Tm is reduced by 0.5-1.5° C. (an average of 1° C. can be used for ease of calculation) for each 1% mismatching. The Tm may also be determined experimentally.

Filter hybridization is typically carried out at 68° C., and at high ionic strength (e.g., 5-6×SSC), which is non-stringent, and followed by one or more washes of increasing stringency, the last one being of the ultimately desired high stringency. The equations for Tm can be used to estimate the appropriate Ti for the final wash, or the Tm of the perfect duplex can be determined experimentally and Ti then adjusted accordingly.

The present invention also relates to a vector comprising the nucleic acid molecule of the present invention. The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

The use of FGFs and FGF fragments for targeting cytotoxic agents has been disclosed in WO 01/39788 and U.S. Pat. Nos. 5,191,067; 5,576,288; 5,679,637. A mitogenically active FGF molecule provides a route for introducing the selected agents into the cell.

Pharmacology

The present invention also provides for a composition comprising at least one polypeptide of the present invention.

"Therapeutic" refers to any pharmaceutical, drug or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term pharmaceutical or drug.

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. Pharmaceutical compositions may also include one or more additional active ingredients.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

The pharmaceutical composition of this invention may be administered by any suitable means, such as orally, intranasally, subcutaneously, intramuscularly, intravenously, intra-arterially, or parenterally. Ordinarily, intravenous (i.v.) or parenteral administration will be preferred.

Methods of the Present Invention

According to another aspect of the present invention it is disclosed that the preferred variant FGFs have improved therapeutic utility in diseases and disorders involving FGF receptors. For example, the FGF2 or FGF4 variant promotes fibroblast growth factor activity in a cell and enhances a biological process associated with fibroblast growth factor activity. Biological activity may be selected from the group consisting of: promotion of cell proliferation, induction or repression of terminal differentiation in a cell, promotion of angiogenesis, promotion of wound healing, promotion of chondrogenesis or osteogenesis, and promotion of neurogenesis. Certain FGF variants of the present invention may be used in the treatment of myocardial infarction (For example U.S. Pat. No. 4,296,100 and U.S. Pat. No. 4,378,347), treating degenerative neurological disorders, including Alzheimer's disease and Parkinson's disease, promoting angiogenesis, promoting bone healing, and promoting muscle healing. Additional therapeutic uses include surgical or non-surgical administration of angiogenic FGF polynucleotides and polypeptides for treating coronary and peripheral vascular disease.

An FGF ligand having increased receptor selectivity is expected to reduce the severity of side effects associated with ligands recognizing and activating multiple FGF receptor subtypes.

Accordingly the present invention provides a method of treating an individual in need thereof comprising the step of administering to that individual a pharmaceutical composition comprising a therapeutically effective amount of at least one N-terminal truncated FGF2 and or FGF4 polypeptide variant according to the present invention.

In another aspect the present invention provides a method of inducing cellular expansion, comprising the steps of:
 a. isolating a population of cells to be expanded; and
 b. exposing said cells to at least one N-terminal truncated FGF2 or FGF4 polypeptide variant according top the principles of the present invention.

The principles of the invention are demonstrated by means of the following non-limitative examples.

EXAMPLES

Example 1: Preparation of FGF Polynucleotide and Polypeptide Variants

The FGF variants were prepared by standard PCR amplification and cloning into a p89BS expression vector. The details of the vector are disclosed in PCT publication WO 02/022779, of some of the inventors of the present invention. The vector has unique NdeI-BamHI restriction sites and the PCR-generated DNA fragments encompassing the coding region of a number of proteins and variants were produced having NdeI and BamHI sites at the 5' and 3' ends respectively. The polynucleotide fragments encoding the proteins were ligated into digested p89BS and the plasmid was used to transform E. coli cells, such as JM109, TG1, TG2, DHα, and XL1blue, using standard transformation protocols.

The primers used for construction of the variants are shown in Table IV, herein below.

TABLE IV forward and reverse primers used in preparation of the FGF2 and FGF4 polynucleotide variants of the present invention.

| Poly-nuleo-tide | SEQ ID NO: | Forward Primer | Backward Primer |
|---|---|---|---|
| FGF2-Δ24 | 34 | 5'GGAATTCCATATGCA CTTCAAGGACCCCAAG SEQ ID NO: 78 | 5'CGGGATCCTCAGCT CTTAGCAG SEQ ID NO: 88 |
| FGF2-Δ25 | 35 | 5'GGAATTCCATATGTT CAAGGACCCCAAGCG SEQ ID NO: 79 | SEQ ID NO: 88 |
| FGF2-Δ26 | 36 | 5'GGAATTCCATATGAA GGACCCCAAGCGGCTG SEQ ID NO: 80 | SEQ ID NO: 88 |
| FGF2-Δ31 | 41 | 5'GGAATTCCATATGCTG TACTGCAAAAACGGGGC SEQ ID NO: 81 | SEQ ID NO: 88 |
| FGF4-Δ72 | 69 | 5'GGAATTCCATATGGCC GGCGACTACCTGCTGG SEQ ID NO: 82 | 5'CGGGATCCTCACAG CCTGGGGAGGAAGTG SEQ ID NO: 89 |
| FGF4-Δ73 | 70 | 5'GGAATTCCATATGGGC GACTACCTGCTGGGCATC SEQ ID NO: 83 | SEQ ID NO: 89 |
| FGF4-Δ74 | 71 | 5'GGAATTCCATATGGAC TACCTGCTGGGCATCAAG SEQ ID NO: 84 | SEQ ID NO: 89 |
| FGF4-Δ75 | 72 | 5'GGAATTCCATATGTAC CTGCTGGGCATCAAGCG SEQ ID NO: 85 | SEQ ID NO: 89 |
| FGF4-Δ76 | 73 | 5'GGAATTCCATATGCTG CTGGGCATCAAGCGG SEQ ID NO: 86 | SEQ ID NO: 89 |
| FGF4-Δ77 | 74 | 5'GGAATTCCATATGCTG GGCATCAAGCGGCTGC SEQ ID NO: 87 | SEQ ID NO: 89 |
| FGF4-Δ78 | 75 | Basilico, et al. | |

A single colony was selected and grown overnight (ON) at 37° C. in a two-liter flask containing 330 ml of TB125 medium (Tryptone 15 gr/L, Yeast extract 30 gr/L, KH$_2$PO$_4$ 2.31 gr/L, K$_2$HPO$_4$ 12.5 gr/L, Glycerol 5 gr/L) supplemented with 200 µg/ml ampicillin. The bacterial suspension was centrifuged at 4000 rpm (4° C.) for 15 minutes, and the medium was discarded. The bacterial pellet was then suspended in 25 ml of 1×PBS buffer containing protease inhibitors, sonicated on ice, and centrifuged at 10,000 rpm (4° C.) for 15 minutes. The protein supernatant was collected and 3 ml of heparin-Sepharose® beads slurry was added and shaken gently for 6 hours at 4° C. The beads were loaded onto a column, washed extensively with PBS buffer containing 0.3M NaCl, and eluted in 7 ml PBS containing 2-2.5M NaCl. The FGF variant proteins were then dialyzed against 1×PBS and repurified on FPLC using a heparin Sepharose column (HiTrap™ Heparin, Amersham Pharmacia biotech) with a 0-2.5M NaCl (in PBS-0.05% CHAPS) linear gradient in the same dialysis buffer. The purified proteins were later stored at −70° C.

Example 2: FGF Variant Binding to FGFR-Transfected FDCP Cell Lines

The FDCP cell line is a murine immortalized, interleukin 3 (IL-3)-dependent cell line of myelocytic bone marrow origin that does not express endogenous FGF Receptors (FGFR). Upon transfection with FGFR cDNA, the FDCP cell line exhibits a dose-dependent proliferative response to FGF that can replace the dependence on IL-3. FGFR transfected FDCP cells can therefore be used to screen variant FGFs for specific inhibitors, activators or for FGFR signaling. FDCP cells response to various ligands is quantitated by a cell proliferation assay with XTT reagent (Cell Proliferation Kit, Biological Industries Co.). The method is based on the capability of mitochondrial enzymes to reduce tetrazolium salts into a colorogenic compound, which can be quantitated and is indicative of cell viability.

Specifically, FDCP cells stably expressing FGFR4, FGFR3-IIIc, FGFR3-IIIb isoforms, FGFR2IIIc or FGFR1IIIc were grown in "full medium" (Iscove's Medium containing 2 ml glutamine, 10% FCS, 100 µg/ml penicillin, 100 µg/ml streptomycin) supplemented with 5 µg/ml heparin and 10 ng/ml FGF. Cells were split every 3 days and kept in culture for up to one month. One day prior to the experiment the cells were split. Before the experiment the cells were washed 3 times (1000 rpm, 6 min) with full medium. The cells were resuspended and counted with Trypan Blue. Twenty thousand (2×10$^4$) cells were added to each well of 96-well plate in 50 µl full medium containing heparin. Conditioned medium containing FGF wild type parent or variants at varying concentrations with heparin was added in an additional volume of 50 µl full medium to bring the final volume to 100 µl. The plate was incubated for 48 hours at 37° C. To assay cell proliferation, 100 µl of PMS reagent was added to 5 ml of XTT reagent and mixed well (according to manufacturer's protocol). Fifty micro-liters (50 µl) of the latter solution were added into each well, and the plates incubated at 37° C. for 4 hours and the color was read by a spectro-ELISA reader at $A_{490nm}$.

In these experiments FDCP cells expressing FGFR4, the FGFR3 isoforms FGFR3IIIb and FGFR3IIIc, FGFR2 or FGFR1 were grown in the presence of varying concentrations of the polypeptides of the invention Example 3. Effect of Variants on Growth Arrest of RCS Chondrocytes RCS is a rat chondrosarcoma derived cell line expressing preferentially high levels of FGFR2 and FGFR3 and low levels of FGFR1. In this cell line, FGFR functions as an inhibitor of cell proliferation similar to its expected role in the achondroplasia phenotype. In order to inhibit cell proliferation, the variants have to specifically induce FGFR signal transduction allowing the measuring of FGF affinity and specificity to the FGFRs reflected by the concentration dependence of induced growth arrest.

The screening was performed on RCS cells in 96 well plates. Cells were seeded at a concentration of about 2,000 cells/well. The following day 10 ng/ml FGF or FGF variants and 5 µg/ml heparin were added to the cells. Positive and negative controls for cell proliferation are included in this assay at the same concentrations as the tested compounds. On the fourth day of incubation, plates were observed under the microscope. If all cells were viable, no quantitative assay to measure the effect of the variants was performed. If cell death was observed, the Cy-Quant® assay kit is used to measure the amount of the cells. The results are measured in a fluoro ELISA reader.

Example 4. JNK Activation by FGF Variants

JNK activation by wild type and variant FGF2 proteins is determined in an in vitro cell assay using stably transfected RCJ (Rat calvaria) cell lines expressing in an inducible manner either the FGFR1IIIC, 2IIIC, 3IIIC or 4 isoforms. In summary, RCJ over-expressing FGFR subtypes are grown in α-MEM++ medium (15% FCS, G-418 600 µg/ml, hygromycin and tetracycline 2-3 µg/ml). The concentration of cells seeded ranges between $7.5 \times 10^4$ and $6 \times 10^5$ cells/well in a 6 well plate. The cell medium is removed 14-16 hours prior to beginning of experiment. Four to five hours before addition of the FGF ligand or variants, the cells are serum-starved. Either wild type or variant FGF are added at a concentration range of 0.1-100 ng/ml for 5-7 minutes at 37° C. FGF stimulation is stopped by cooling the cells on ice followed by washing 3 times with cold PBS. The cells are lysed by addition of lysis buffer (1 mM EGTA, 1 mM EDTA, 25 mM Tris/50 mM Hepes, 25 mM NaF, 50 mM β-glycerophosphate, 50 mM NaCl, 10% Glycerol, 1% NP40, pH 7.5, freshly prepared Orthovanadate to 2 mM, and protease inhibitors) for 10 minutes on ice. The cell lysates are collected and spun for 10 minutes at 15,000 rpm. Protein aliquots are loaded on SDS-PAGE and activation is viewed in a standard Western assay using rabbit anti-active JNK antibodies (Promega). In each lane, cell lysate of RCJ cells exposed to 0, 12.5, 25, 50 or 100 ng of wild-type or variant FGF is loaded.

Example 5: Phosphorylation Assay Using Anti-MAPK/ERK Antibodies

FGF/FGFR-dependent ERK activation signal transduction is measured in an ELISA assay using monoclonal anti-diphosphorylated ERK antibodies. The assay is followed by reading $A_{450nm}$ after addition of the TMB reagent to monitor the total ERK activation.

RCJ over-expressing FGFR subtypes were grown as described hereinabove in Example 4. Following the collection of cell lysates, SDS was added to the supernatants to 1.5% final concentration and the mixture incubated for 15 min at room temperature. Following protein determination, the protein and SDS concentrations were adjusted with lysis buffer to a final concentration of 7 µg protein and 0.15% SDS in 100 µl. 100 µl of sample lysate is added to a Maxisorp® 96 well plate (Nunc immuno-plate430341) precoated with monoclonal anti-diphosphorylated MAPK/ERK (Sigma M8159) diluted to 1:3000 with a mixture 4% BSA in TBST and lysis buffer adjusted to 0.15% SDS. The plates are incubated, shaken, for 2 hours at room temperature. The wells were washed and each well incubated with 100 µl of 1:10,000 dilution of HRP-conjugated goat anti-mouse IgG (Jackson Immunoresearch 800-367-5296) in 2% BSA/TBST for 1-1.5 hrs at room temp, with shaking. Following incubation, the samples were washed 5-6 times with TBST, and 100 µl of developing medium (1:1 mixtures A and B of ImmunoPure® TMB substrate kit) is added for 10 minutes at room temperature. The reaction was stopped by the addition of $H_2SO_4$ and the absorbance was read at 450 nm.

Example 6: Chondrocyte Expansion

The effect of FGF and FGF variants on proliferation of articular chondrocytes was tested. Articular Chondrocyte culture: Chondrocytes are isolated from pig or human biopsies and cultured using the FGF variants of the present invention to identify the effect of the variants on proliferation and differentiation. The procedure employed for the isolation and propagation of articular chondrocytes is presented below.

Reagents:
Dulbecco's MEM (DMEM) (Gibco BRL)
MEM Non-Essential Amino Acids (Gibco BRL)
Sodium Pyruvate (Gibco BRL)
Fetal Bovine Serum (FBS) (Gibco BRL)
Streptomycin, Penicillin, Nystatin Solution (Biological Indus. Ltd.)
Trypsin-EDTA (Gibco BRL, cat. no. T8154) or Versene-Trypsin (Bio LAB Ltd.)
Collagenase Type 2 (Worthington Biochem. Corp.). A stock solution of 1700 units/ml Collagenase in DMEM was prepared and filtered (0.2 µm).
EZ-RNA kit (Biological Industries Israel Beit Haemek)
Reverse-iT strand synthesis kit (AB gene)
GeneAmp® 5700 Sequence detection system (Applied Biosystems)
RPLPO Assays-on Demond™ (Applied Biosystems)
Preparation of FBS-DMEM Medium:
FBS (50 ml), 5 ml of antibiotic solution, 5 ml Sodium Pyruvate, 5 ml MEM non-essential amino acids were added to a 500 ml bottle of DMEM. Where specified, FGF2, FGF4 or FGF variants were added to a final concentration of 10 ng/ml.

Isolation of Cells from Cartilage Biopsy:
A piece of cartilage tissue is minced into 2 to 4 mm pieces with a sterile scalpel. The collagenase solution is diluted 1:4 in FBS-DMEM, added to the tissue sample and left to incubate on a rotator at 37° C., overnight (ON). The cells are centrifuged (1200 rpm, 5-10 min). The medium is aspirated, the cells washed in 5 ml medium and recentrifuged. The cells are resuspended in culture medium and seeded in 25 cm² or 75 cm² flasks at a concentration of approximately 1×10⁶ cells per flask. The cells were incubated in a 5% $CO_2$ incubator at 37° C. The cell medium was replaced every 2-3 days.

Procedure for Passaging Cells (Trypsinization):

When the cell culture reached the desired confluency the medium was removed and the cells trypsinized in the following manner: One milliliter (1 ml) of the trypsin solution was added to a 25 cm² flask or 2.5 ml to a 75 cm² flask. The flask was gently shaken by hand for two seconds and the trypsin solution was immediately removed. Another 1 ml of trypsin was added to a 25 cm² flask or 2.5 ml to a 75 cm² flask. The flask was gently shaken by hand for ~30 seconds and left to incubate at 37° C. for 3-5 minutes. Verify under the microscope that cells are detached. The trypsin was neutralized by adding FBS-MEM; add 10 ml to a 25 cm² flask and 25 ml to a 75 cm² flask. The cells were split to 2-3 new flasks and 20 ml fresh pre-warmed medium was added. The expansion of cells and trypsinization was performed as necessary.

Furthermore, the cell population grown on the above matrices expresses several of the chondrocyte differentiation markers. One of several phenotypes expressed during chondrocyte differentiation is glycosaminoglycan (GAG) production. The production of GAGs is identified in histological staining using Alcian blue and quantitated using the DMB (3,3'-dimethoxybenzidine dihydrochloride) dye method.

Proliferation of the cartilage cells in the presence of the different variants can be quantitated by one of two methods, CyQUANT® (Molecular Probes) or XTT reagent (Biological Industries, Co.). Human or porcine articular chondrocytes (10⁴-10⁶ cells/30-100 µl) are grown in the presence of the variants of the invention in microwell plates. The cells are grown overnight in MEM, collected and XTT reagent is added for 3-4 hours and the plates read in an ELISA reader at $A_{490}$ nm.

Example 7: Effect of FGF Variants on Bone Fracture Healing

Ulnas are fractured in New Zealand Rabbits in compliance with the Animal Care Committees. The ulna was chosen because it is only slightly weight-bearing and allows the creation of a bone defect without requiring a cast or other immobilization treatment. In addition, this gap constitutes a spontaneously healing defect that allows the evaluation of the tested agent. The primary indices of fracture healing are accelerated duration of healing and callus formation.

A 0.6 cm radial gap osteotomy is created under anesthesia with rotary saw in both ulnas of each animal. Approximately 1 ml of a composition comprising the test compounds is administered by injection into the gap. The periosteum, which is not resected during the surgery, is used to close the gap. Fracture healing is radiologically evaluated every week up to 4 weeks p.o. (post osteotomy). An X-ray closure of both limbs in a lateral position was taken. X-ray films are examined by a Film Digitizer, and the following parameters were measured: Total area of regenerated bone appearing around and within the bone gap defect (callus area) and the relative density of the newly regenerated bone in the gap defect. Histopathological evaluation was made by preparing thin sections that were stained with hematoxylin and eosin for cytoplasm and nucleus. Indigo-Carmin staining is also applied for detection of new generated callus.

Example 8: Bone Marrow Stem Cells: Isolation and Proliferation

Human articular chondrocytes were isolated from pieces of cartilage using digestion enzymes. Isolated primary chondrocytes were seeded in 75 cm² flasks (5×10⁴ cells) containing DMEM/F12, 20% human serum, 10 ng/ml of different FGF variant of the present invention and 5 µg/ml low molecular heparin (LMW). Cells were counted in different time points using the Vi-Cell XR.

Example 9: Bone Marrow Stem Cells: Isolation and Expansion

Samples of human bone marrow were used to isolate mesenchymal stem cells by adherence to plastic dishes in the presence of MSC expansion medium, namely, DMEM-LG containing 20% human serum (HS), or 10 ng/ml FGF2 and FGF4 variants of the present invention and with or without 5 mg/ml low molecular weight (LMW) Heparin. For proliferation assay 2×10⁴ cells were seeded per well in a 24 wells plate. Cells were counted every 6-7 days using the Vi-Cell XR and reseeded to obtain several time points.

Example 10: Bone Marrow Stem Cells: In-Vitro Chondrogenesis Assay

The expanded chondrocytes or hBM-MSC were used for in-vitro chondrogenesis assay to produce high density pellet cultures. There pellet cultures were incubated for 21 days in chondrocytes differentiation medium containing DMEM, 10 ng/ml TGF-b, 100 mM Dexamethasone, 0.28 mM Ascorbic acid, 1 mM Sodium pyruvate, 40 µg/ml Proline, 10 µg/ml Bovine insulin, 5.5 µg/ml Human transferin, 5 µg/ml Sodium selenite, 0.5 mg/ml Bovine serum albumin and 1.7 µg/ml Linoleic acid.

Example 11: Bone Marrow Stem Cells: Histology Analysis of Pellet Cultures

Pellet cultures incubated for 3 weeks in differentiation medium were fixed in PFA solution and paraffin block were prepared. Sections were used for analysis of proteoglycans by Alcian blue (AB) and Safranin O (SO) stains and for examine Col II expression by immunohistochemistry with anti Col II antibodies.

Example 12: Bone Marrow Stem Cells: qPCR Analysis of Col II

RNA was isolated from pellet cultures by EZ-RNA kit (Biological Industries Israel Beit Haemek). The RNA was used to prepare cDNA using the Reverse-iT strand synthesis kit (AB gene). qPCR was performed using GeneAmp® 5700 Sequence detection system (Applied Biosystems). cDNA samples were analyzed for quantitative expression of Col II and the reference gene RPLPO using Assays-on Demond™ (Applied Biosystems). For each cDNA sample, the threshold cycle (Ct) value of target sequence was subtracted by Ct value of RPLPO, to derive ΔCt. Relative level of Col II was calculated as 2ΔCt.

Example 13: Bone Marrow Stem Cells: In-Vitro Osteogenesis Assay

Cells (2×10⁴ per well) were seeded on 6 well plate and cultures for 1, 2 or 3 weeks in osteoblast differentiation medium (DMEM-HG, 10% FCS, 100 nM Dexamethasone, 0.05 mM Ascorbic acid, 10 mM β-glycerolphosphate). Cells were stained with Alizarin Red for analysis of calcium in matrix.

Example 14: Effects of FGF Variants on Femoral Growth

Femoral bone cultures are performed by excising the hind limbs of wild type mice. The limbs are carefully cleaned from the surrounding tissue (skin and muscles) and the femora exposed. The femora are removed and further cleared from tissue remains and ligaments. The femora are measured for their initial length, using a binocular with an eyepiece micrometer ruler. The bones are grown in 1 ml of medium with FGF2 or FGF4 variants in a 24 well tissue culture dish. The growing medium is α-MEM supplemented with penicillin (100 units/ml), streptomycin (0.1 mg/ml) and Nystatin (12.5 units/ml). In addition, the medium contains BSA (0.2%), β-glycerophosphate (1 mM) and freshly prepared ascorbic acid (50 µg/ml). The bones are cultured for 15 days. Measurements of bone length and medium replacement are performed every three days. At the end of the experiment, the growth rate of the bones are determined from the slope of a linear regression fit on the length measurements obtained from day 3 to 12. Units given can be converted to length, 40 units=1 mm.

Example 15: Effect of FGF2 Variants in Bone Fracture Healing

Suitable animal models are used to create bilateral osteotomies to demonstrate the efficacy of the novel variants of the present invention. In a rabbit model a 6 mm osteotomy is created in New Zealand Rabbits in compliance with the Animal Care Committee of the Hebrew University. The ulna was chosen because it is only slightly weight-bearing and allows the creation of a bone defect without requiring a cast or other immobilization treatment. In addition, this gap constitutes a spontaneously healing defect that allows the evaluation of the tested agent. The primary indices of fracture healing are accelerated duration of healing and callus formation. The test compounds consist of FGF2 or FGF4 variants in a polymeric scaffold which facilitates bone growth.

Surgical Procedure:

Animals are anesthetized according to standard protocol. Gap formation is performed in the mid Ulna bone. A standard volume of 0.2 ml of treatment formulation is put into the gap area in each limb and the fracture is closed. Animals are treated with analgesics for 3 days post operation. The duration of the experiment is 6 weeks.

Healing Time and Quality Assessment:

Healing time evaluation: X-ray grading provides fracture healing status assessment. Rabbits are x-rayed every other week for 5 weeks after surgery. Two orthopedic surgeons score X-rays in a blinded manner according to standard grading scale protocol.

Quality Evaluation:

At the end of the experiment rabbits are sacrificed and fracture area is sent for histological and mechanical strength evaluation. Histology is scored by a pathologist for evaluation of histological changes during the healing process using standard staining methods, using hematoxylin and eosin for cytoplasm and nucleus. Indigo-Carmin staining is also applied for detection of newly generated callus. Mechanical strength evaluation is performed using the "4 points bending" method.

The treatments groups are:

Osteotomy without treatment, Osteotomy treated with polymeric scaffold alone, Osteotomy treated with scaffold containing FGF2 and an osteotomy treated with scaffold containing FGF2 variants.

Example 16: Efficacy of FGF Variants in Distraction Osteogenesis

Distraction osteogenesis is a useful method for bone elongation of extremities in short stature and for the treatment of extensive bone defects. Several procedures for bone lengthening have been developed for use in the clinic. The problems encountered in using this technique include an extended healing time and complications such as non-union or poor quality of the regenerated bone.

The maximal rate of elongation used in the current procedure of limb elongation, while maintaining proper bone healing and reconstitution, is 1 mm/day. Faster elongation rates have resulted in lack of fusion or in the formation of weak bone that breaks easily or cannot bear body weight. In this process, extreme conditions of elongation (1.5 mm/day) will be performed in order to observe a more significant effect of the added compounds on the background of natural healing.

The objectives of the experiment are to assess the quality of bone formation, time of bone formation and safety after elongation using a calcium phosphate (CaP) scaffold embedded with the FGF2 or FGF4 variant.

Treatment Arms:

Treatment 1 (Control): 5 lambs (5 limbs), no treatment
Treatment 2: 5 lambs (5 limbs): CaP alone
Treatment 3: 5 lambs (5 limbs): CaP with FGF2 or FGF4 variant Materials and Methods:

Lambs are assigned randomly into one of the five treatment arms. Surgical lengthening of the right femur is performed in 25 lambs aged from 3 to 4 months.

Anesthesia and Pre-Mediation:

General anesthesia is given without endotracheal intubation. Intramuscular atropine is given as premedication (0.5 mg/kg), and thiopentone sodium-2.5% (10-15 mg/kg), Fentanyl® (0.0015 mg/kg) and Diazepam® (0.2 mg/kg) is administered intravenously.

Fixation:

A monolateral external fixator (Monotube-Triax®, Stryker Trauma, Geneva, Switzerland) with four pins, two proximal and two distal in each of its pin clamps, is positioned so that the pins are kept away from the growth plates and the surface of the joint. The osteotomy is performed using a pneumatic saw.

Lengthening:

Lengthening begins seven days after surgery for all treatment groups: Lengthening continues until the limb has been lengthened by 4.5 cm. The total elongation period lasts 30 days at a rate of 1.5 mm/day starting the 8 h day after surgery.

Treatment:

Lambs are assigned randomly into one of the four treatment arms. All treatments take place during the consolidation period, at day 44.

Treatment 1 (control): To assess the effect during the consolidation period, animals remain without treatment until the end of the trial period.

Treatment 2: To assess the effect of CaP alone during the consolidation period, it will be administered once, one week after completion of elongation.

Treatment 3: To assess the effect of the variant protein during consolidation period, CaP with FGF2 or FGF4 variant is administered once, one week after completion of elongation.

Follow Up:

Animals are in a restricted area during the extent of the whole experiment and are allowed to feed and walk ad libitum in own cage. Animals are weighed at fixed intervals and general well-being is monitored.

To study the bone formation in the host bone, four different fluorochromes are used as bone markers, administered IM, according to the following schedule: one week after surgery: calcein (green; Sigma®); two weeks after surgery: alizarin (red; Sigma®); three weeks after surgery: xylenol (orange; Fluka®) and three days before sacrifice oxytetracycline will be given (Duphacycline®). The Spalteholz technique is performed after intra-arterial injection of Berlin blue studied through the femoral artery before sacrifice to analyze the vascularization of the lengthened callus in each group.

Completion:

The animals are sacrificed three months after initial surgery by IV injection of 5 µg of KCl, after anesthesia with sodium pentobarbital (1.5 mg/kg weight).

Assessment of Efficacy:

Success is determined in terms of healing time and bone quality obtained after elongation and treatment with FGF2 or FGF4 variant and if no major adverse effects are observed.

X-Ray:

Progress of bone healing is followed by X-ray at weeks 1, 2 and 4 after beginning of elongation. The parameters to be assessed from the X-ray are:
1. Degree of callus formation
2. Gap closure
3. Remodeling achieved during treatment.

X-ray scoring is performed by an orthopedic surgeon, according to an established bone healing grading system, according to the following: No callus—0, primary callus response at one end of bone—1, primary cluus response at both ends of bone—2, partial external callus union—3, complete external callus union—4, <30% gap closure—5, >30% gap closure—6, complete gap closure—7, partial callus remodeling—8, complete callus remodeling—9; Gap filling calculation: (A/A+B)×100 equals the percentage of gap filling.

Histology:

The callus is divided into two parts, one for embedding in paraffin, and the other for embedding in methylmethacrylate. For the histological study, the specimens will be fixed in Bouin for 24 hours and decalcified in a solution of PVP-EDTA, at 4° C. Once specimens have been decalcified, they are dehydrated using increasing concentration of alcohols (70%, 80%, 96% and 100%), and after 4 hours in xylene, they are embedded in paraffin at a temperature of 60° C. The specimens are sectioned to 4 µm, and stained with Masson's trichrome, hematoxylin and eosin (H&E), Safranin O and von Kossa.

To analyze the mineralization by fluorochromes, the specimens are fixed in formol for one week, then dehydrated using alcohols of increasing proof. After one week in PMMA-alcohol and three weeks in PMMA (Technovit 7200 VLC®), specimens will be sectioned with a diamond saw (Exakt®) and trimmed to a thickness of 14 µm. After measuring the sections with ultraviolet light the distance of the bone markers is measured and the bone index formation calculated (distance mm/days). The proximal parts of both, lengthened and control, tibiae are extracted and cut in lateral and medial parts. The lateral portion is placed in 4% buffered formaldehyde. After decalcification of all the specimens in EDTA, are proceed to embed them in paraffin and cut them into 4 µm slices. Stains of H&E, Masson's trichrome, Safranin 0 and Alcian blue-PAS are applied.

Immunohistochemistry:

Specific antibodies recognizing collagen L collagen II, FGFa (FGF1), and S-100 are applied to the lengthened callus sections by an indirect two-step method The 4 µm paraffin sections are dewaxed in xylene and taken through ethanol 100%. After trypsinization, following deparaffinization, endogenous peroxidase is blocked by placing the sections in hydrogen peroxidase solution for 30 min. They are then incubated in the following reagents with appropriate Tris-buffered-saline (TBS: 0.55 M, pH 7.36) washes: normal pig serum for 30 min, abovementioned primary antibodies for 1 hour, a secondary biotinylated antibody for 30 min, and avidin-biotin complex (Dako K0355) for 30 min. The reaction is visualized with chromogen substrate solution (di-aminobenzidine, hydrogen peroxidase, TB) and sections are counterstained with Harris's hematoxylin, dehydrated, and mounted. As a negative control, TBS is used in the procedure instead of the primary antibodies. All stained sections are examined and photographed with use of a microscope (Nikon Optiphot-2®, Japan).

Morphometric Analysis:

With an image analyzing system (Leica Q 500 MC®) the histomorphometric parameters are determined. With Masson's trichrome stain the following parameters are determined:
1. Trabecular width.
2. Trabecular area.
3. Trabecular erosion surface.
4. Index of trabecular erosion.
5. Number of osteoblasts.
6. Number of osteoclasts per field.
7. Number of osteoclast nuclei.
8. Index of bone reabsorption or number osteoclast nuclei/osteoclasts.

With von Kossa's stain the following parameters are obtained.
1. Osteoid width.
2. Osteoid-trabecular index, and fluorescence will be used to measure.
3. Bone formation index.

Example 17: Goat Articular Cartilage Repair Model

A comparative study to evaluate the efficacy of the FGF variants in treating articular cartilage defects in a goat knee injury model is performed. A total of 6 adult female goats are used. AR of the animals undergo a chondrocyte harvest procedure prior to implantation. The collected tissue will be used for preparation of autologous primary chondrocytes. Three weeks post operative, a 4.5 mm diameter and 1.5 mm deep hole are punched out and natural matrix matrices, with or without FGF variants, pre-seeded with different concentrations of allogeneic cells are implanted in the corresponding individual goat for a long term experiment (12 weeks). After 12 weeks, all animals are humanely euthanized. The joints are grossly evaluated for specific changes of the femoral condyle and the contacting surfaces. Histological analysis is performed to determine the structural and cellular response to the implant materials.

Materials and Methods:

Six adult female goats (11-12 months old) are used. In one particular experimental system the different tests include:

Antibiotics: 2 ml of amoxycillin is injected IM immediately before the procedure and once a day for 4 days after the procedure.

Anesthesia: Pre-medication: 0.05 mg/kg xylazine followed by ketamine-diazepam (4 mg/kg and 2 mg/kg IV) is administered IM.

Surgery and Implantation:

The basic surgical procedure is identical for all subjects. All surgeries are performed under strict asepsis. Peri-operative antibiotics are dosed IM at 2.4 million units of Penicillin procaine (40,000 units/kg SID) at the beginning of the procedure. Anesthesia is induced with xylazine 0.05 mg/kg IM followed by ketamine-diazepam (4 mg/kg and 2 mg/kg IV). The subject is intubated in ventral position and then positioned to left recumbency. Anesthesia is maintained with a gaseous mixture of Isoflurane and oxygen. Analgesia, carprofen 2-4 mg/kg SQ, SID.

Harvest Procedure:

The surgical approach consists of a curved, lateral skin incision made from the distal one-third of the left femur to the level of the tibial plateau and across to the medial side of the tibial spine. Using this method, the skin is bluntly dissected and retracted to allow a lateral parapatellar approach into the stifle joint. An incision is made parallel to the lateral border of the patella and patellar ligament. This extends from the lateral side of the fascia lata along the cranial border of the biceps femoris and into the lateral fascia of the stifle joint. The biceps femoris and attached lateral fascia are retracted allowing an incision into the joint capsule. The joint is extended and the patella luxated medially exposing the stifle joint.

The harvest site is the same as the location of the planned trochlear defect which is created in the right femoral condyle. The defects is approximately 5 mm in diameter and approximately 2.5 mm in depth, and will pass into the subchondral bone. The defects are made on either the lateral or medial wall of the distal trochlear sulcus dependent on individual anatomy. The harvested cartilage layer is approximately 5 mm in diameter and approximately 0.5 mm in depth. The harvested cells are transferred to cell culture medium immediately after harvest for expansion and matrix seeding. The incision is closed in layers using appropriate suture and patterns.

Implantation Procedure:

The trochlear defect is created in the right femoral condyle. The defects are approximately 5 mm in diameter and approximately 2.5 mm in depth, and pass into the subchondral bone. The defects are made on either the lateral or medial wall of the distal trochlear sulcus dependent on individual anatomy. Each defect is filled with the appropriate test article.

The surgical approach consists of a curved, lateral skin incision made from the distal one-third of the left femur to the level of the tibial plateau and across to the medial side of the tibial spine. Using this method, the skin is bluntly dissected and retracted to allow a lateral parapatellar approach into the stifle joint. An incision is made parallel to the lateral border of the patella and patellar ligament. This extends from the lateral side of the fascia lata along the cranial border of the biceps femoris and into the lateral fascia of the stifle joint. The biceps femoris and attached lateral fascia are retracted allowing exposure to the joint capsule. The joint is extended and the patella luxated medially exposing the stifle joint.

With the knee joint fully flexed, the appropriate location for the points of drilling the defect on the trochlear sulcus are identified and marked with a surgical marker. A specially designed cartilage cutter is used to slice through the cartilage outer layer and prevent tearing of the cartilage. The approximate 5 mm diameter core cutter is used under power to create a fixed depth of approximately 2.5 mm, maintaining a plane perpendicular to the tangent of the sulcus. The core of subchondral bone and cartilage is carefully removed. The cutter is carefully removed and any loose cartilage edging is carefully dissected with a scalpel blade. If needed, a handheld powered drill with a specially designed drill bit is used to chamfer the edge of the created defect. This undercutting may assist in providing a mechanical lock with the matrix.

The cartilage defects are copiously flushed with sterile saline prior to insertion of the test article. The appropriate test material is then placed into the defect such that it is in line with the surrounding cartilage and covered with biological glue to maintain in place. A final saline flush of the joint is carefully done. The patella is then reduced and the joint moved through a complete range-of-motion to ensure that there is no impingement due to the implants. This is followed by routine closure of the joint in three or four layers using appropriate suture material.

Post operatively, a modified Thomas splint is applied to the leg. This remains in place for 2 weeks to limit flexing of the operated knee. Post operative checks are made for any animal displaying signs of post operative discomfort. Post operative analgesics are given for 5 days if the animals display any signs of distress of discomfort. All treatments are recorded in the appropriate study documentation.

Necropsy:

Animals are humanely sacrificed at 12 weeks postoperatively. Bodyweights are recorded immediately prior to sacrifice. Deep anesthesia is induced with a mixture of ketamine-xylazine and the subject exsanguinated according to the guidelines set forth by the AVMA Panel on Euthanasia (JAVMA, March 2000).

Gross evaluation and sample collection are performed. Lymph node in close proximity to the joint is examined. The articulating surfaces opposing the defect sites are examined for any abnormal joint surface. Additionally, gross evaluations of the knee joints are made to determine the cartilage repair. Femora, patellae, synovium, and popliteal lymph nodes are harvested and placed into appropriately labeled containers. Immediately following tissue harvest, gross morphological examination of the cartilage surface is done as described above and photographic records made of each specimen.

Gross Morphological Observations:

After collection of the knee joints, the joints are opened, photographed and the surface of the defect site is scored. The synovial membrane is examined for any inflammation. Joint fluid is collected and analyzed.

Histology and Histological Evaluation:

Immediately after dissection and following gross joint surface observations, the joints is placed in 10% phosphate buffered formalin (at least ten-fold volume) for at least 48 hours and sent for histological processing. After fixation in 10% phosphate buffered formalin, the specimens are grossly trimmed to remove extra tissue. The tissue blocks are cut approximately {fraction (1/3)} of the distance in from the exterior implant/tissue interface in order to examine them grossly. Contact radiographs are taken prior to the commencement of decalcification.

The tissues are decalcified in 10% EDTA until radiographs of the decalcified sections assures complete decalcification. Once complete decalcification is determined, the specimens are dehydrated through an ethanol series and paraffin embedded. The specimens are sectioned. One section is stained with H&E and another sequential section with Safranin O counter-stained with Fast Green. For histologic analysis of the sections, the scoring scale according to Frenkel is used.

Histological evaluation is performed to measure the following parameters: Characteristics of the neo-formed tissue, regularity of the joint surface of the regenerated tissue, structural integrity and thickness of the regenerated tissue, endochondral ossification and state of the cells in the remaining cartilage.

Example 18: Pharmacokinetics

Methods for detecting administered compounds in the blood or tissue of treated mammals are known in the art. The pharmacokinetic properties of the administered compounds are determined using such methods. In animal models, radiolabelled oligonucleotides or peptides can be administered and their distribution within body fluids and tissues assessed by extraction of the oligonucleotides or peptides followed by autoradiography. Other methods include labeling of a peptide with a reporter moiety, including fluorescent or enzyme labels, administration to an animal, extraction of the peptide from body fluids and organs followed by HPLC analysis. Alternatively, immunohistochemical methods are used for detection of the administered peptide in tissue. The present invention contemplates reporter labeled FGF polypeptides and chimeras, fusion protein, hybrids and conjugates using the same.

Results:
FGF4: Activity and specificity of hFGF4$^{\Delta 78}$ and FGF4$^{\Delta 54 N 165 R}$ The hFGF4$^{\Delta 78}$ N-terminal polypeptide was disclosed in Bellosta et al. (2001) as an FGF4 ligand having wild type characteristics. The N-terminal truncated FGF4$^{\Delta 54}$ and the N-terminal truncated and mutated FGF4$^{\Delta 54 N 16512}$, which were disclosed in International patent application WO 03/094835 were shown to have normal activity towards FGFR3 and FGFR1 and thus were used for comparison.

FDCP-FGFR1, FGFR2 or FGFR3 cells were grown with increasing FGF4$^{\Delta 78}$ or FGF4$^{\Delta 54 N 165 R}$ concentrations and the resulting proliferation response was measured by XTT. FDCP-FGFR1 and FDCP-FGFR2 cells responded similarly to both ligands. Unexpectedly, the FGF4$^{\Delta 78}$ behaved as a poor ligand for FGFR3, inducing a growth response at only 25 ng/ml and more, while FDCP-FGFR3 cells proliferate at as little as 0.1 ng/ml hFGF4$^{\Delta 54 N 165 R}$.

Figure 2:
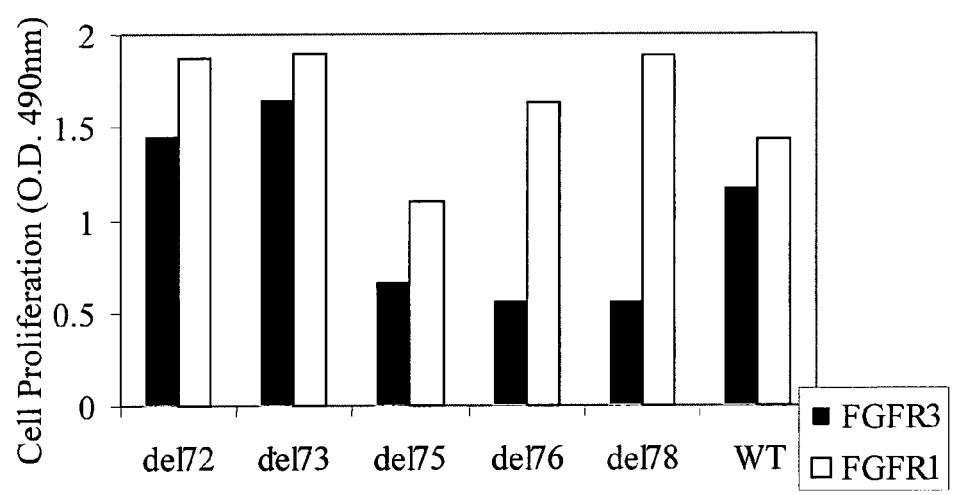
FIG. 2. Structure function analysis of FGF4. Successive N-terminal deletion mutants were added to FDCP-FGFR1 (white columns) or FDCP-FGFR3 (black columns) cells. Cell proliferation was determined 2 days followed by the XTT assay.

To precisely map the amino-terminal domain required for full activity of FGF4, a series of one amino acid successive N-terminal deletions, $\Delta 72$-$\Delta 77$, was prepared. These constructs were generated by PCR, cloned into p89, expressed and purified as described for the above variants. FDCP-FGFR1 and FGFR3 cells were exposed to the different truncated mutants for 2 days and then followed cell proliferation. FIG. 2 shows hFGF4$^{\Delta 72}$ and hFGF4$^{\Delta 73}$ induced FDCP-FGFR3 cell proliferation as well as the wild-type FGF4, yet larger deletions demonstrated decreasing activation of the FGFR3 bearing cells. Such reduced activity was not observed with FDCP-FGFR1 cells, emphasizing the importance of amino acids 74-78 for FGFR3 activation.

FGF2: Activity and Specificity of N-Truncated FGF2 Polypeptides

Figure 3A:
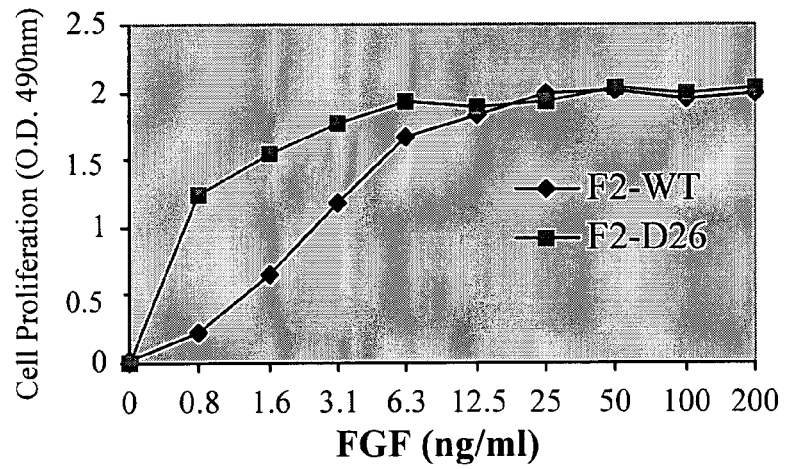
FIGS. 3A-3C. Activity of N-terminal truncated FGF2 (FGF2$^{\Delta26}$) towards different FGF receptors. FGF2$^{\Delta26}$ (squares) retains wild-type activity towards FGFR1 (FIG.
Figure 3B:
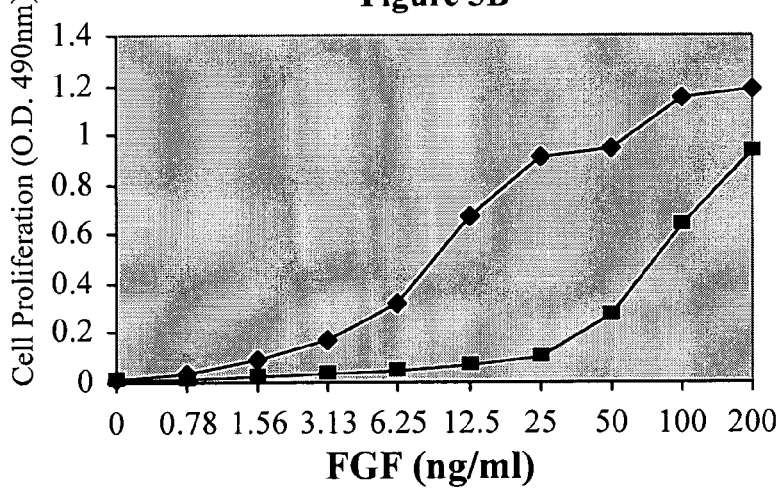
Figure 3C:
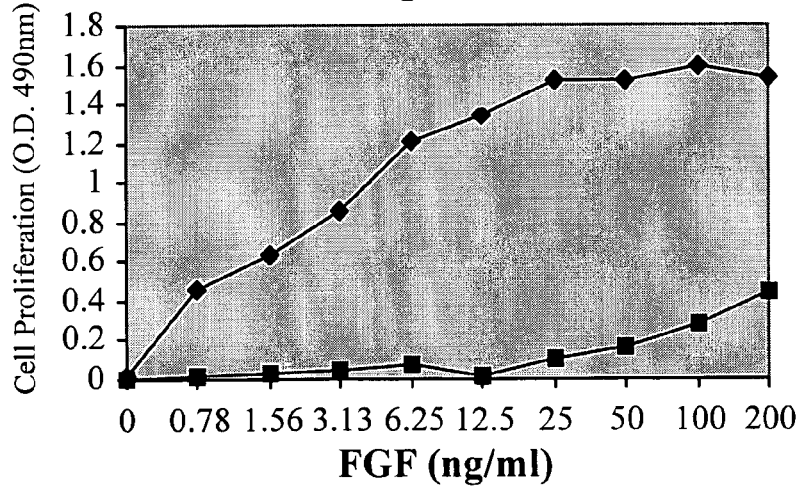

A series of FGF2 N-terminal truncated variants were prepared. The FGF2$^{\Delta 26}$ variant was tested in FDCP proliferation assays. FGFR2 and FGFR3 activation by FGF2$^{\Delta 26}$ is severely reduced while that of FGFR1 remained intact as compared to the activation by the wild-type FGF2 ligand (F2-WT; FIG. 3A-3C).

The ligands were then tested in the RCJ system. RCJ cells expressing either FGFR1, FGFR2 or FGFR3 were stimulated with an increasing dose of wild-type or mutant FGF2 and lysates from stimulated cells were analyzed by Western with a phospho MAPK (antiphospho ERK; FIG. 4). The activity of FGF2$^{\Delta 26}$ mirrored that observed in the FDCP cell system showing equal activation, as the wild-type, of MAPK in RCJ-FGFR1 cells and a relatively reduced one in RCJ-FGFR2 and -FGFR3 cells. Thus the increased specificity of N-terminal truncated FGF2 might be relevant to a broad range of biological systems. FIGS. 5A and 5B show the proliferative response of FGFR1 (A) and FGFR3 (B) expressing cells to FGF2$^{\Delta 26}$ and FGF2$^{\Delta 31}$ variant ligands.

In an effort to map the N-terminal residues required for FGFR2, FGFR3 and FGFR4 recognition successively smaller N-terminal variants that lack either residues 2-25 (FGF2$^{\Delta 25}$) or 2-24 (FGF2$^{\Delta 24}$) were generated and subjected to a proliferation assay of FDCP-FGFR cells. Both FGF2$^{\Delta 25}$ and FGF2$^{\Delta 24}$ demonstrated potent activation of FGFR1 similar to that obtained with FGF2$^{\Delta 26}$ (FIG. 6A). As demonstrated previously, FGF2$^{\Delta 26}$ was a poor activator of the other 3 receptors (the activity towards FGFR2 is shown in FIG. 8M). The activity of FGF2$^{\Delta 26 N 111 G}$ was similar to that of the FGF2$^{\Delta 26}$ variant. It did, however, show a larger stability in comparison to FGF2$^{\Delta 26}$ lacking the N111G mutation. The addition of a single amino acid to the FGF2$^{\Delta 26}$, namely phenylalanine 25 in FGF2$^{\Delta 25}$ reactivated, at least in part, its ability to induce a proliferative response in cells expressing FGFR3 and FGFR4. In line with these data, FGF2$^{\Delta 24}$ demonstrated wild-type activity in FDCP-FGFR3 and FDCP-FGFR4 cells suggesting that phenylalanine 24 and histidine 25 may be required for full activation of these receptors (FIG. 6B-6C).

The nearly full activation of FGFRs by FGF2$^{\Delta 24}$ compared to the remarkable FGFR1 specificity of FGF2$^{\Delta 26}$ suggests that positions 25 and 26 are important for receptor binding. A set of 15 oligonucleotides that encompass these 2 positions and code for representatives of acidic, basic, polar or non-polar amino acids were designed at these two sites. The 15 mutants were cloned in p89 as $\Delta 24$ N-terminal truncated ligands. Production of 14 out of 15 mutants was demonstrated ($\Delta 24$H25QF26Q expression was undetectable). The mutants were purified using heparin-Sepharose® beads and quantified by gel densitometry.

The mutant ligands were then added at increasing dose to FDCP-FGFR1 cells and the resulting cell proliferation was measured by XTT analysis (FIGS. 7A-7N; Table V).

TABLE V

Activation of FGFR1-4 by N-terminal truncated FGF2 variants

|  | SEQ ID NO: | FGFR1 | FGFR2 | FGFR3 | FGFR4 |
|---|---|---|---|---|---|
| FGF2 (wt) | 3 | ++++ | ++++ | ++++ | ++++ |
| FGF2$^{\Delta 24}$ | 5 | ++++ | +++ | +++ | +++ |
| FGF2$^{\Delta 25}$ | 6 | ++++ | +++ | ++ | ++ |
| FGF2$^{\Delta 26}$ | 7 | ++++ | ++ | + | + |
| $\Delta 24$H25D | 17 | ++++ | +++ | +++ | ++ |
| $\Delta 24$H25Q | 18 | ++++ | +++ | +++ | ++ |
| $\Delta 24$H25V | 19 | ++++ | +++ | +++ | + |
| $\Delta 24$H25K | 20 | ++++ | +++ | + | + |
| $\Delta 24$F26D | 21 | +++ | + | − | − |
| $\Delta 24$F26Q | 22 | ++++ | + | − | + |

TABLE V-continued

Activation of FGFR1-4 by N-terminal truncated FGF2 variants

|  | SEQ ID NO: | FGFR1 | FGFR2 | FGFR3 | FGFR4 |
|---|---|---|---|---|---|
| Δ24F26K | 23 | +++ | + | − | + |
| Δ24F26Y | 24 | ++++ | +++ | +++ | +++ |
| Δ24H25DF26D | 25 | ++++ | ++ | + | − |
| Δ24H25DF26Q | 26 | ++++ | ++ | − | − |
| Δ24H25DF26K | 27 | ++++ | + | − | − |
| Δ24H25QF26D | 28 | ++++ | ++ | + | − |
| Δ24H25QF26K | 29 | ++++ | + | − | − |
| Δ24H25VF26D | 30 | ++++ | ++ | − | + |
| Δ24H25VF26Q | 31 | ++++ | ++ | + | + |
| Δ24H25VF26K | 32 | ++++ | + | − | − |
| Δ24H25KF26Q | 33 | +++ | − | − | − |

All mutants activated FGFR1 efficiently yet slight differences were observed (Table V). Specifically, all single mutants with substitution at His25 were slightly more active towards FGFR1 than wild-type FGF2 while those harboring a mutation at Phe26, either as a single or double mutant were as active as, or slightly less active than the wild-type. These mutants were then analyzed in FDCP cells that express the other three receptor types.

This experiment showed that the single His mutants, FGF2$^{\Delta 24H25D}$, FGF2$^{\Delta 24H25Q}$ and FGF2$^{\Delta 24H25V}$ were, at least as active as FGF2$^{\Delta 24}$ in activating FGFR2 (FIG. 8; Table V). In contrast, all variants with substitution at Phe26 were less active than FGF2$^{\Delta 24}$ and except FGF2$^{\Delta 24H25DF26Q}$ and FGF2$^{\Delta 24H25VF26D}$ were also less active than FGF2$^{\Delta 26}$. This suggests that the deleterious effect of mutations at Phe26 to Asp or Gln may be alleviated by the substitution of the positively charged His at position 25 for a non-polar or a negatively charged residue. In general, the effect of the different mutations on FGFR3 activation was very similar to that on FGFR2 except that FGF2$^{\Delta 24H25DF26Q}$ and FGF2$^{\Delta 24H25VF26D}$ were as inactive as the other variants (FIG. 9).

The only receptor that responded less to the FGF variants FGF2$^{\Delta 24H25D}$, FGF2$^{\Delta 24H25Q}$, FGF2$^{\Delta 24H25V}$ than to FGF2$^{\Delta 24}$ was FGFR4 (FIG. 10). This suggests that His25 has a role in FGFR4 activation and that Phe26, is important for FGFR4 activation as it is for FGFR2 and FGFR3.

The heparin requirement of the different mutants for activating FGFR1 was analyzed under very low heparin concentrations (FIG. 11). This allowed the discrimination between different His 25 mutants, showing that FGF2$^{\Delta 24H25D}$ requires the lowest heparin concentrations for its biological activity (FIG. 11A). As before, any mutation at Phe26 reduced the ability of the ligand to induce FDCP-FGFR1 cell proliferation and all tested ligands with a double mutation at His 25 and Phe 26 required less heparin than the respective single Phe 26 mutants (FIG. 11B-11D).

Since a positive charge at position 25 showed a negative effect on ligand activity, His 25 was replaced with amino acids that possess higher pK values. The following mutants: FGF2$^{\Delta 24H25K}$ and FGF2$^{\Delta 24H25KF26Q}$ were thus prepared as described for the above variants and compared with FGF2$^{\Delta 24}$, FGF2$^{\Delta 24H25D}$, FGF2$^{\Delta 24F26Q}$ and FGF2$^{\Delta 24H25DF26Q}$ (FIG. 12). FDCP-FGFR3 cells (FIG. 12B) showed that FGF2$^{\Delta 24H25D}$ was more potent while FGF2$^{\Delta 24H25K}$ was less potent than FGF2$^{\Delta 24}$. Moreover, the double mutant FGF2$^{\Delta 24H25DF26Q}$ rescued in part the loss of activity of FGF2$^{\Delta 24F26Q}$ while FGF2$^{\Delta 24H25KF26Q}$ was as inactive as FGF2$^{\Delta 24F26Q}$. In general, FDCP-FGFR1 cells (FIG. 12A) are strongly activated even by the mutant FGF variants. However, qualitative differences similar to those found in FDCP-FGFR3 cells were also observed in FDCP-FGFR1 cells. Hence, replacing His 25 with amino acids that have higher pK values rendered the mutant less active than wild-type FGF2.

To further confirm the role of Phe 26 in receptor binding, a mutation was introduced in the context of wild-type FGF2. The activity of FGF2$^{F26Q}$ was compared to that of wild-type FGF2. XTT analysis in the presence of saturated heparin concentrations showed similar FGFRs activation by both ligands (FIGS. 13A-13C). However, when the activity of the FGF2$^{F26Q}$ mutant was compared to that of the wild-type FGF2 under limiting concentrations of heparin, the mutant ligand was considerably less active than the wild-type FGF2 in FDCP-FGFR2 and FDCP-FGFR3 (FIGS. 13E-13F) but not in FDCP-FGFR1 cells (FIG. 13D).

In contrast to the non-conservative mutations described above, a conservative mutation at position 26 replacing Phe26 with Tyr (FGF2$^{\Delta 24F26Y}$) did not alter the activity of the mutant compared to its native counterpart (FGF$^{\Delta 24}$), (FIG. 14; Table V). Thus, aromatic amino acids at position 26 fulfill the structural requirements for FGFR activation.

FGF2 and FGF4 Variants: Chondrogenic and Osteogenic Potential

The chondrogenic and osteogenic potential of bone marrow stem cells was determined by culturing the cells in FGF2 or FGF4 variants of the present invention. The cells cultured in the presence of the different ligands were examined for their in-vitro chondrogenic potential using the pellet culture assay. The effect of novel FGF2 variants, namely FGF2$^{\Delta 26}$ and FGF2$^{\Delta 31}$ on primary human articular chondrocytes proliferation is shown in FIG. 15. Both FGF2 variants enhanced the proliferation rate of primary human articular chondrocytes.

A high proliferation rate was observed when both the FGF2 variants (FGF2$^{\Delta 24F26Q}$ and FGF2$^{\Delta 26}$) and the FGF4 variant (FGF4$^{\Delta 78}$) were included in the medium of all bone marrow samples tested (FIG. 16). The proliferation rate of the FGF2 variants was very similar and higher than with no ligand. The proliferation rate of FGF4$^{\Delta 78}$ was slightly lower than that of the FGF2 variants, yet it showed a higher proliferation rate in comparison to the one lacking a ligand. The chondrogenic potential of the chondrocytes cultured with the FGF2 and FGF4 variants was improved and showed stronger marker for hyaline cartilage.

Results of pellet cultures histology of the bone marrow stem cells showed that cells cultured with FGF2 and FGF2$^{\Delta 26}$ gave pellet culture similar in size and with massive amount of GAG's and sulfated GAG's (FIG. 17). It seems that cells cultured with FGF2 showed slightly larger signal in Safranin O stain (SO) than cells cultured with FGF2$^{\Delta 26}$. Also, high amount of Collagen II was observed by immunohistochemistry with anti Col II antibodies of the pellets produced from the cells cultured with FGF2 and FGF2$^{\Delta 26}$ variant. Human bone marrow derived mesenchymal stem cells expanded without FGF showed poor chondrogenic potential in comparison to that obtained with FGF2 variants FGF2$^{\Delta 24}$, FGF2$^{\Delta 26}$ and FGF2$^{\Delta 31}$ (FIG. 18).

qPCR analysis of Col II in pellet culture produced from human bone marrow derived mesenchymal stem cells expanded with different FGF2 variants of the present invention, showed high chondrogenic potential (FIG. 19). Moreover, the chondrogenic potential of hBM-MSC cultured with FGF2$^{\Delta 31}$ was higher than those of cells cultured with FGF2$^{\Delta 26}$. FGF2$^{\Delta 26}$ showed similar results to FGF2$^{\Delta 24F26Q}$ yet significantly higher chondrogenic potential than FGF2. In general the qPCR results, which provide RNA information, are in good agreement with the chondrogenic potential observed for the FGF variants.

To examine the multipotency of the expanded bone marrow stem cells with the various ligands an in-vitro osteogenic assay was set up. Results shown in FIG. 20 showed very similar intensity of Alizarin red stain for all cultures.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aviezer et al. *J. Biol. Chem.* 269, p. 114, 1994
Bellosta et al. *Mol. Cell Biol.* 21(17), p. 5946, 2001
Bikfalvi et al. *Endo. Rev.* 18, p. 26, 1997
Imamura et al. *Sci.* 249, p. 1567, 1990
Kuroda et al. *Bone* 25, p. 431, 1999
Mohammadi et al. *Cyto. Growth Factor Rev.* 16(2), p. 107, 2005
Okada-Ban et al. *Int. J. Biochem. Cell Biol.* 32, p. 263, 2000
Olsen et al. *Proc. Natl. Acad. Sci. US* 101, p. 935, 2004
Ornitz, *Bioessays* 22, p. 108, 2000
Ornitz et al. *J. Biol. Chem.* 271, p. 15292, 1996
Ornitz and Itoh, *Gen. Biol.* 2(3), p. 30005, 2001
Plotnikov et al. *Cell* 101, p. 413, 2000
Presta et al. *Growth Factors* 9, p. 269, 1993
Sambrook et al. *Molecular Cloning: A Laboratory Manual*, 2$^{nd}$ Ed., Cold Spring Harbor Press, 1989
Seno et al. *Eur. J. Biochem.* 188, p. 239, 1990
Springer et al. *J. Biol. Chem.* 269: p. 26879, 1994
Wong et al. *J. Biol. Chem.* 270, p. 25805, 1995
Yayon et al. *Cell* 64, p. 841, 1991
Yayon et al. *Proc. Natl. Acad. Sci. US* 90, p. 10643, 1993
Zhu et al. *Protein Eng.* 10, p. 417, 1997

---

The invention claimed is:

1. A human fibroblast growth factor 2 (FGF2) variant whose activity toward a fibroblast growth factor receptor (FGFR) subtype selected from FGFR2, FGFR3, and FGFR4 is less than half of the activity of human wild-type FGF2 toward FGFR2, FGFR3, or FGFR4, respectively, at normal physiological conditions;
    whose activity toward FGFR1 is similar to the activity of human wild-type FGF2 toward FGFR1 at normal physiological conditions; and
    wherein the FGF2 variant comprises an N-terminal deletion and a polypeptide sequence selected from SEQ ID NO: 22-23 and 25-33.

2. A pharmaceutical composition comprising as an active ingredient a human fibroblast growth factor 2 (FGF2) variant according to claim 1 and a pharmaceutically acceptable diluent or carrier.

3. The pharmaceutical composition according to claim 2 formulated for administration via intra-articular, intravenous, intramuscular, subcutaneous, intradermal, or intrathecal routes.

4. A method of inducing cellular expansion, comprising the steps of:
    isolating a population of cells to be expanded; and
    exposing said cells to a human fibroblast growth factor 2 (FGF2) variant whose activity toward a fibroblast growth factor receptor (FGFR) subtype selected from FGFR2, FGFR3, and FGF is less than half of the activity of human wild-type FGF2 toward FGFR2, FGFR3, or FGF, respectively, at normal physiological conditions;
    whose activity toward FGFR1 is similar to the activity of human wild-type FGF2 toward FGFR1 at normal physiological conditions; and wherein the FGF2 variant comprises an N-terminal deletion and a polypeptide sequence selected from SEQ ID NO: 22-23 and 25-33.

5. The method of claim 4, wherein the population of cells to be expanded the cells are selected from stem cells or progenitor cells.

6. The method of claim 4, wherein the population of cells to be expanded comprises hematopoietic cells.

7. The method of claim 4, wherein the population of cells to be expanded comprises cells selected from chondrocytes, osteoblasts, hepatocytes, fibroblasts or mesenchymal, endothelial, epithelial, urothelial, endocrine, neuronal, pancreatic, renal and ocular cell types.

* * * * *

SEQUENCE LISTING

```
<160> NUMBER OF SEQ ID NOS: 94

<210> SEQ ID NO 1
<211> LENGTH: 123
<212> TYPE: PRT
<213> ORGANISM: Artificial
<220> FEATURE:
<223> OTHER INFORMATION: Synthetic

<400> SEQUENCE: 1

Lys Arg Leu Tyr Cys Lys Asn Gly Gly Phe Phe Leu Arg Ile His Pro
1               5                   10                  15

Asp Gly Arg Val Asp Gly Val Arg Glu Lys Ser Asp Pro His Ile Lys
            20                  25                  30

Leu Gln Leu Gln Ala Glu Glu Arg Gly Val Val Ser Ile Lys Gly Val
        35                  40                  45

Cys Ala Asn Arg Tyr Leu Ala Met Lys Glu Asp Gly Arg Leu Leu Ala
    50                  55                  60

Ser Lys Cys Val Thr Asp Glu Cys Phe Phe Phe Glu Arg Leu Glu Ser
65                  70                  75                  80

Asn Asn Tyr Asn Thr Tyr Arg Ser Arg Lys Tyr Thr Ser Trp Tyr Val
                85                  90                  95

Ala Leu Lys Arg Thr Gly Gln Tyr Lys Leu Gly Ser Lys Thr Gly Pro
            100                 105                 110

Gly Gln Lys Ala Ile Leu Phe Leu Pro Met Ser
        115                 120

<210> SEQ ID NO 2
<211> LENGTH: 123
<212> TYPE: PRT
<213> ORGANISM: Artificial
<220> FEATURE:
<223> OTHER INFORMATION: Synthetic

<400> SEQUENCE: 2

Arg Arg Leu Tyr Cys Asn Val Gly Ile Gly Phe His Leu Gln Ala Leu
1               5                   10                  15

Pro Asp Gly Arg Ile Gly Gly Ala His Ala Asp Thr Arg Asp Ser Leu
            20                  25                  30
```

```
Leu Glu Leu Ser Pro Val Glu Arg Gly Val Val Ser Ile Phe Gly Val
             35                  40                  45

Ala Ser Arg Phe Phe Val Ala Met Ser Ser Lys Gly Lys Leu Tyr Gly
 50                  55                  60

Ser Pro Phe Phe Thr Asp Glu Cys Thr Phe Lys Glu Ile Leu Leu Pro
 65                  70                  75                  80

Asn Asn Tyr Asn Ala Tyr Glu Ser Tyr Lys Tyr Pro Gly Met Phe Ile
                 85                  90                  95

Ala Leu Ser Lys Asn Gly Lys Thr Lys Lys Gly Asn Arg Val Ser Pro
                100                 105                 110

Thr Met Lys Val Thr His Phe Leu Pro Arg Leu
            115                 120

<210> SEQ ID NO 3
<211> LENGTH: 155
<212> TYPE: PRT
<213> ORGANISM: Homo sapiens

<400> SEQUENCE: 3

Met Ala Ala Gly Ser Ile Thr Thr Leu Pro Ala Leu Pro Glu Asp Gly
 1                   5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 4
<211> LENGTH: 206
<212> TYPE: PRT
<213> ORGANISM: Homo sapiens

<400> SEQUENCE: 4

Met Ser Gly Pro Gly Thr Ala Ala Val Ala Leu Leu Pro Ala Val Leu
 1                   5                  10                  15

Leu Ala Leu Leu Ala Pro Trp Ala Gly Arg Gly Gly Ala Ala Ala Pro
                 20                  25                  30

Thr Ala Pro Asn Gly Thr Leu Glu Ala Glu Leu Glu Arg Arg Trp Glu
             35                  40                  45

Ser Leu Val Ala Leu Ser Leu Ala Arg Leu Pro Val Ala Ala Gln Pro
 50                  55                  60

Lys Glu Ala Ala Val Gln Ser Gly Ala Gly Asp Tyr Leu Leu Gly Ile
 65                  70                  75                  80
```

```
Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
            115                 120                 125

Phe Gly Val Ala Ser Arg Phe Phe Val Ala Met Ser Ser Lys Gly Lys
130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
            195                 200                 205
```

<210> SEQ ID NO 5
<211> LENGTH: 131
<212> TYPE: PRT
<213> ORGANISM: Artificial
<220> FEATURE:
<223> OTHER INFORMATION: Synthetic

<400> SEQUENCE: 5

```
His Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
                20                  25                  30

Asp Pro His Ile Lys Leu Gln Leu Gln Ala Glu Glu Arg Gly Val Val
            35                  40                  45

Ser Ile Lys Gly Val Cys Ala Asn Arg Tyr Leu Ala Met Lys Glu Asp
50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
            115                 120                 125

Ala Lys Ser
130
```

<210> SEQ ID NO 6
<211> LENGTH: 130
<212> TYPE: PRT
<213> ORGANISM: Artificial
<220> FEATURE:
<223> OTHER INFORMATION: Synthetic

<400> SEQUENCE: 6

```
Phe Lys Asp Pro Lys Arg Leu Tyr Cys Lys Asn Gly Gly Phe Phe Leu
1               5                   10                  15

Arg Ile His Pro Asp Gly Arg Val Asp Gly Val Arg Glu Lys Ser Asp
                20                  25                  30

Pro His Ile Lys Leu Gln Leu Gln Ala Glu Glu Arg Gly Val Val Ser
            35                  40                  45
```

```
Ile Lys Gly Val Cys Ala Asn Arg Tyr Leu Ala Met Lys Glu Asp Gly
     50                  55                  60

Arg Leu Leu Ala Ser Lys Cys Val Thr Asp Glu Cys Phe Phe Phe Glu
 65                  70                  75                  80

Arg Leu Glu Ser Asn Asn Tyr Asn Thr Tyr Arg Ser Arg Lys Tyr Thr
                     85                  90                  95

Ser Trp Tyr Val Ala Leu Lys Arg Thr Gly Gln Tyr Lys Leu Gly Ser
                100                 105                 110

Lys Thr Gly Pro Gly Gln Lys Ala Ile Leu Phe Leu Pro Met Ser Ala
            115                 120                 125

Lys Ser
    130

<210> SEQ ID NO 7
<211> LENGTH: 129
<212> TYPE: PRT
<213> ORGANISM: Artificial
<220> FEATURE:
<223> OTHER INFORMATION: Synthetic

<400> SEQUENCE: 7

Lys Asp Pro Lys Arg Leu Tyr Cys Lys Asn Gly Gly Phe Phe Leu Arg
 1                5                  10                  15

Ile His Pro Asp Gly Arg Val Asp Gly Val Arg Glu Lys Ser Asp Pro
                 20                  25                  30

His Ile Lys Leu Gln Leu Gln Ala Glu Glu Arg Gly Val Val Ser Ile
             35                  40                  45

Lys Gly Val Cys Ala Asn Arg Tyr Leu Ala Met Lys Glu Asp Gly Arg
 50                  55                  60

Leu Leu Ala Ser Lys Cys Val Thr Asp Glu Cys Phe Phe Phe Glu Arg
 65                  70                  75                  80

Leu Glu Ser Asn Asn Tyr Asn Thr Tyr Arg Ser Arg Lys Tyr Thr Ser
                 85                  90                  95

Trp Tyr Val Ala Leu Lys Arg Thr Gly Gln Tyr Lys Leu Gly Ser Lys
                100                 105                 110

Thr Gly Pro Gly Gln Lys Ala Ile Leu Phe Leu Pro Met Ser Ala Lys
            115                 120                 125

Ser

<210> SEQ ID NO 8
<211> LENGTH: 128
<212> TYPE: PRT
<213> ORGANISM: Artificial
<220> FEATURE:
<223> OTHER INFORMATION: Synthetic

<400> SEQUENCE: 8

Asp Pro Lys Arg Leu Tyr Cys Lys Asn Gly Gly Phe Phe Leu Arg Ile
 1                5                  10                  15

His Pro Asp Gly Arg Val Asp Gly Val Arg Glu Lys Ser Asp Pro His
                 20                  25                  30

Ile Lys Leu Gln Leu Gln Ala Glu Glu Arg Gly Val Val Ser Ile Lys
             35                  40                  45

Gly Val Cys Ala Asn Arg Tyr Leu Ala Met Lys Glu Asp Gly Arg Leu
 50                  55                  60

Leu Ala Ser Lys Cys Val Thr Asp Glu Cys Phe Phe Phe Glu Arg Leu
 65                  70                  75                  80
```

```
Glu Ser Asn Asn Tyr Asn Thr Tyr Arg Ser Arg Lys Tyr Thr Ser Trp
                85                  90                  95

Tyr Val Ala Leu Lys Arg Thr Gly Gln Tyr Lys Leu Gly Ser Lys Thr
            100                 105                 110

Gly Pro Gly Gln Lys Ala Ile Leu Phe Leu Pro Met Ser Ala Lys Ser
        115                 120                 125
```

<210> SEQ ID NO 9
<211> LENGTH: 127
<212> TYPE: PRT
<213> ORGANISM: Artificial
<220> FEATURE:
<223> OTHER INFORMATION: Synthetic

<400> SEQUENCE: 9

```
Pro Lys Arg Leu Tyr Cys Lys Asn Gly Gly Phe Phe Leu Arg Ile His
1               5                   10                  15

Pro Asp Gly Arg Val Asp Gly Val Arg Glu Lys Ser Asp Pro His Ile
            20                  25                  30

Lys Leu Gln Leu Gln Ala Glu Glu Arg Gly Val Val Ser Ile Lys Gly
        35                  40                  45

Val Cys Ala Asn Arg Tyr Leu Ala Met Lys Glu Asp Gly Arg Leu Leu
50                  55                  60

Ala Ser Lys Cys Val Thr Asp Glu Cys Phe Phe Phe Glu Arg Leu Glu
65                  70                  75                  80

Ser Asn Asn Tyr Asn Thr Tyr Arg Ser Arg Lys Tyr Thr Ser Trp Tyr
                85                  90                  95

Val Ala Leu Lys Arg Thr Gly Gln Tyr Lys Leu Gly Ser Lys Thr Gly
            100                 105                 110

Pro Gly Gln Lys Ala Ile Leu Phe Leu Pro Met Ser Ala Lys Ser
        115                 120                 125
```

<210> SEQ ID NO 10
<211> LENGTH: 126
<212> TYPE: PRT
<213> ORGANISM: Artificial
<220> FEATURE:
<223> OTHER INFORMATION: Synthetic

<400> SEQUENCE: 10

```
Lys Arg Leu Tyr Cys Lys Asn Gly Gly Phe Phe Leu Arg Ile His Pro
1               5                   10                  15

Asp Gly Arg Val Asp Gly Val Arg Glu Lys Ser Asp Pro His Ile Lys
            20                  25                  30

Leu Gln Leu Gln Ala Glu Glu Arg Gly Val Val Ser Ile Lys Gly Val
        35                  40                  45

Cys Ala Asn Arg Tyr Leu Ala Met Lys Glu Asp Gly Arg Leu Leu Ala
50                  55                  60

Ser Lys Cys Val Thr Asp Glu Cys Phe Phe Phe Glu Arg Leu Glu Ser
65                  70                  75                  80

Asn Asn Tyr Asn Thr Tyr Arg Ser Arg Lys Tyr Thr Ser Trp Tyr Val
                85                  90                  95

Ala Leu Lys Arg Thr Gly Gln Tyr Lys Leu Gly Ser Lys Thr Gly Pro
            100                 105                 110

Gly Gln Lys Ala Ile Leu Phe Leu Pro Met Ser Ala Lys Ser
        115                 120                 125
```

```
<210> SEQ ID NO 11
<211> LENGTH: 125
<212> TYPE: PRT
<213> ORGANISM: Artificial
<220> FEATURE:
<223> OTHER INFORMATION: Synthetic

<400> SEQUENCE: 11

Arg Leu Tyr Cys Lys Asn Gly Gly Phe Phe Leu Arg Ile His Pro Asp
1               5                   10                  15

Gly Arg Val Asp Gly Val Arg Glu Lys Ser Asp Pro His Ile Lys Leu
            20                  25                  30

Gln Leu Gln Ala Glu Glu Arg Gly Val Val Ser Ile Lys Gly Val Cys
        35                  40                  45

Ala Asn Arg Tyr Leu Ala Met Lys Glu Asp Gly Arg Leu Leu Ala Ser
    50                  55                  60

Lys Cys Val Thr Asp Glu Cys Phe Phe Phe Glu Arg Leu Glu Ser Asn
65                  70                  75                  80

Asn Tyr Asn Thr Tyr Arg Ser Arg Lys Tyr Thr Ser Trp Tyr Val Ala
                85                  90                  95

Leu Lys Arg Thr Gly Gln Tyr Lys Leu Gly Ser Lys Thr Gly Pro Gly
            100                 105                 110

Gln Lys Ala Ile Leu Phe Leu Pro Met Ser Ala Lys Ser
        115                 120                 125

<210> SEQ ID NO 12
<211> LENGTH: 124
<212> TYPE: PRT
<213> ORGANISM: Artificial
<220> FEATURE:
<223> OTHER INFORMATION: Synthetic

<400> SEQUENCE: 12

Leu Tyr Cys Lys Asn Gly Gly Phe Phe Leu Arg Ile His Pro Asp Gly
1               5                   10                  15

Arg Val Asp Gly Val Arg Glu Lys Ser Asp Pro His Ile Lys Leu Gln
            20                  25                  30

Leu Gln Ala Glu Glu Arg Gly Val Val Ser Ile Lys Gly Val Cys Ala
        35                  40                  45

Asn Arg Tyr Leu Ala Met Lys Glu Asp Gly Arg Leu Leu Ala Ser Lys
    50                  55                  60

Cys Val Thr Asp Glu Cys Phe Phe Phe Glu Arg Leu Glu Ser Asn Asn
65                  70                  75                  80

Tyr Asn Thr Tyr Arg Ser Arg Lys Tyr Thr Ser Trp Tyr Val Ala Leu
                85                  90                  95

Lys Arg Thr Gly Gln Tyr Lys Leu Gly Ser Lys Thr Gly Pro Gly Gln
            100                 105                 110

Lys Ala Ile Leu Phe Leu Pro Met Ser Ala Lys Ser
        115                 120

<210> SEQ ID NO 13
<211> LENGTH: 129
<212> TYPE: PRT
<213> ORGANISM: Artificial
<220> FEATURE:
<223> OTHER INFORMATION: Synthetic

<400> SEQUENCE: 13

Lys Asp Pro Lys Arg Leu Tyr Cys Lys Asn Gly Gly Phe Phe Leu Arg
1               5                   10                  15
```

Ile His Pro Asp Gly Arg Val Asp Gly Val Arg Glu Lys Ser Asp Pro
            20                  25                  30

His Ile Lys Leu Gln Leu Gln Ala Glu Glu Arg Gly Val Val Ser Ile
        35                  40                  45

Lys Gly Val Cys Ala Asn Arg Tyr Leu Ala Met Lys Glu Asp Gly Arg
    50                  55                  60

Leu Leu Ala Ser Lys Cys Val Thr Asp Glu Cys Phe Phe Phe Glu Arg
65                  70                  75                  80

Leu Glu Ser Asn Gly Tyr Asn Thr Tyr Arg Ser Arg Lys Tyr Thr Ser
                85                  90                  95

Trp Tyr Val Ala Leu Lys Arg Thr Gly Gln Tyr Lys Leu Gly Ser Lys
            100                 105                 110

Thr Gly Pro Gly Gln Lys Ala Ile Leu Phe Leu Pro Met Ser Ala Lys
        115                 120                 125

Ser

<210> SEQ ID NO 14
<211> LENGTH: 131
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X= any amino acid residue other than His (H)

<400> SEQUENCE: 14

Xaa Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
        130

<210> SEQ ID NO 15
<211> LENGTH: 131
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X= amino acid residue other than Phe (F)

<400> SEQUENCE: 15

```
His Xaa Lys Asp Pro Lys Arg Leu Tyr Cys Lys Asn Gly Gly Phe
1               5                   10                  15

Leu Arg Ile His Pro Asp Gly Arg Val Asp Gly Val Arg Glu Lys Ser
                20                  25                  30

Asp Pro His Ile Lys Leu Gln Leu Gln Ala Glu Glu Arg Gly Val Val
            35                  40                  45

Ser Ile Lys Gly Val Cys Ala Asn Arg Tyr Leu Ala Met Lys Glu Asp
        50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
                100                 105                 110

Ser Lys Thr Gly Pro Gly Gln Lys Ala Ile Leu Phe Leu Pro Met Ser
            115                 120                 125

Ala Lys Ser
    130

<210> SEQ ID NO 16
<211> LENGTH: 131
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X= amino acid residue other than His (H)
<220> FEATURE:
<221> NAME/KEY: MISC_FEATURE
<222> LOCATION: (2)..(2)
<223> OTHER INFORMATION: X= amino acid residue other than Phe (F)

<400> SEQUENCE: 16

Xaa Xaa Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
                20                  25                  30

Asp Pro His Ile Lys Leu Gln Leu Gln Ala Glu Glu Arg Gly Val Val
            35                  40                  45

Ser Ile Lys Gly Val Cys Ala Asn Arg Tyr Leu Ala Met Lys Glu Asp
        50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
                100                 105                 110

Ser Lys Thr Gly Pro Gly Gln Lys Ala Ile Leu Phe Leu Pro Met Ser
            115                 120                 125

Ala Lys Ser
    130

<210> SEQ ID NO 17
<211> LENGTH: 131
<212> TYPE: PRT
<213> ORGANISM: Artificial
<220> FEATURE:
<223> OTHER INFORMATION: Synthetic
```

```
<400> SEQUENCE: 17

Asp Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 18
<211> LENGTH: 131
<212> TYPE: PRT
<213> ORGANISM: Artificial
<220> FEATURE:
<223> OTHER INFORMATION: Synthetic

<400> SEQUENCE: 18

Gln Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 19
<211> LENGTH: 131
<212> TYPE: PRT
<213> ORGANISM: Artificial
<220> FEATURE:
<223> OTHER INFORMATION: Synthetic

<400> SEQUENCE: 19

Val Phe Lys Asp Pro Lys Arg Leu Tyr Cys Lys Asn Gly Gly Phe Phe
1               5                   10                  15
```

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 20
<211> LENGTH: 131
<212> TYPE: PRT
<213> ORGANISM: Artificial
<220> FEATURE:
<223> OTHER INFORMATION: Synthetic

<400> SEQUENCE: 20

Lys Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 21
<211> LENGTH: 131
<212> TYPE: PRT
<213> ORGANISM: Artificial
<220> FEATURE:
<223> OTHER INFORMATION: Synthetic

<400> SEQUENCE: 21

His Asp Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val

-continued

```
            35                  40                  45
Ser Ile Lys Gly Val Cys Ala Asn Arg Tyr Leu Ala Met Lys Glu Asp
         50                  55                  60
Gly Arg Leu Leu Ala Ser Lys Cys Val Thr Asp Glu Cys Phe Phe Phe
 65                  70                  75                  80
Glu Arg Leu Glu Ser Asn Asn Tyr Asn Thr Tyr Arg Ser Arg Lys Tyr
                 85                  90                  95
Thr Ser Trp Tyr Val Ala Leu Lys Arg Thr Gly Gln Tyr Lys Leu Gly
            100                 105                 110
Ser Lys Thr Gly Pro Gly Gln Lys Ala Ile Leu Phe Leu Pro Met Ser
        115                 120                 125
Ala Lys Ser
        130
```

<210> SEQ ID NO 22
<211> LENGTH: 131
<212> TYPE: PRT
<213> ORGANISM: Artificial
<220> FEATURE:
<223> OTHER INFORMATION: Synthetic

<400> SEQUENCE: 22

```
His Gln Lys Asp Pro Lys Arg Leu Tyr Cys Lys Asn Gly Gly Phe Phe
 1               5                  10                  15
Leu Arg Ile His Pro Asp Gly Arg Val Asp Gly Val Arg Glu Lys Ser
             20                  25                  30
Asp Pro His Ile Lys Leu Gln Leu Gln Ala Glu Glu Arg Gly Val Val
            35                  40                  45
Ser Ile Lys Gly Val Cys Ala Asn Arg Tyr Leu Ala Met Lys Glu Asp
         50                  55                  60
Gly Arg Leu Leu Ala Ser Lys Cys Val Thr Asp Glu Cys Phe Phe Phe
 65                  70                  75                  80
Glu Arg Leu Glu Ser Asn Asn Tyr Asn Thr Tyr Arg Ser Arg Lys Tyr
                 85                  90                  95
Thr Ser Trp Tyr Val Ala Leu Lys Arg Thr Gly Gln Tyr Lys Leu Gly
            100                 105                 110
Ser Lys Thr Gly Pro Gly Gln Lys Ala Ile Leu Phe Leu Pro Met Ser
        115                 120                 125
Ala Lys Ser
        130
```

<210> SEQ ID NO 23
<211> LENGTH: 131
<212> TYPE: PRT
<213> ORGANISM: Artificial
<220> FEATURE:
<223> OTHER INFORMATION: Synthetic

<400> SEQUENCE: 23

```
His Lys Lys Asp Pro Lys Arg Leu Tyr Cys Lys Asn Gly Gly Phe Phe
 1               5                  10                  15
Leu Arg Ile His Pro Asp Gly Arg Val Asp Gly Val Arg Glu Lys Ser
             20                  25                  30
Asp Pro His Ile Lys Leu Gln Leu Gln Ala Glu Glu Arg Gly Val Val
            35                  40                  45
Ser Ile Lys Gly Val Cys Ala Asn Arg Tyr Leu Ala Met Lys Glu Asp
         50                  55                  60
```

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 24
<211> LENGTH: 131
<212> TYPE: PRT
<213> ORGANISM: Artificial
<220> FEATURE:
<223> OTHER INFORMATION: Synthetic

<400> SEQUENCE: 24

His Tyr Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 25
<211> LENGTH: 131
<212> TYPE: PRT
<213> ORGANISM: Artificial
<220> FEATURE:
<223> OTHER INFORMATION: Synthetic

<400> SEQUENCE: 25

Asp Asp Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 26
<211> LENGTH: 131
<212> TYPE: PRT
<213> ORGANISM: Artificial
<220> FEATURE:
<223> OTHER INFORMATION: Synthetic

<400> SEQUENCE: 26

Asp Gln Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 27
<211> LENGTH: 131
<212> TYPE: PRT
<213> ORGANISM: Artificial
<220> FEATURE:
<223> OTHER INFORMATION: Synthetic

<400> SEQUENCE: 27

Asp Lys Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 28
<211> LENGTH: 131
<212> TYPE: PRT
<213> ORGANISM: Artificial
<220> FEATURE:
<223> OTHER INFORMATION: Synthetic

<400> SEQUENCE: 28

Gln Asp Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 29
<211> LENGTH: 131
<212> TYPE: PRT
<213> ORGANISM: Artificial
<220> FEATURE:
<223> OTHER INFORMATION: Synthetic

<400> SEQUENCE: 29

Gln Lys Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

```
<210> SEQ ID NO 30
<211> LENGTH: 131
<212> TYPE: PRT
<213> ORGANISM: Artificial
<220> FEATURE:
<223> OTHER INFORMATION: Synthetic

<400> SEQUENCE: 30

Val Asp Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 31
<211> LENGTH: 131
<212> TYPE: PRT
<213> ORGANISM: Artificial
<220> FEATURE:
<223> OTHER INFORMATION: Synthetic

<400> SEQUENCE: 31

Val Gln Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 32
<211> LENGTH: 131
<212> TYPE: PRT
<213> ORGANISM: Artificial
```

```
<220> FEATURE:
<223> OTHER INFORMATION: Synthetic

<400> SEQUENCE: 32

Val Lys Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 33
<211> LENGTH: 131
<212> TYPE: PRT
<213> ORGANISM: Artificial
<220> FEATURE:
<223> OTHER INFORMATION: Synthetic

<400> SEQUENCE: 33

Lys Gln Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Lys Arg Thr Gly Gln Tyr Lys Leu Gly
            100                 105                 110

Ser Lys Thr Gly Pro Gly Gln Lys Ala Ile Leu Phe Leu Pro Met Ser
        115                 120                 125

Ala Lys Ser
    130

<210> SEQ ID NO 34
<211> LENGTH: 399
<212> TYPE: DNA
<213> ORGANISM: Artificial
<220> FEATURE:
<223> OTHER INFORMATION: Synthetic

<400> SEQUENCE: 34
```

```
atgcacttca aggaccccaa gcggctgtac tgcaaaaacg ggggcttctt cctgcgcatc    60
caccccgacg gccgagttga cggggtccgg gagaagagcg accctcacat caagctacaa   120
cttcaagcag aagagagagg agttgtgtct atcaaggag tgtgtgctaa ccgttacctg   180
gctatgaagg aagatggaag attactggct tctaaatgtg ttacggatga gtgtttcttt   240
tttgaacgat tggaatctaa taactacaat acttaccggt caaggaaata caccagttgg   300
tatgtggcac tgaaacgaac tgggcagtat aaacttggat ccaaaacagg acctgggcag   360
aaagctatac ttttcttcc aatgtctgct aagagctga                           399

<210> SEQ ID NO 35
<211> LENGTH: 396
<212> TYPE: DNA
<213> ORGANISM: Artificial
<220> FEATURE:
<223> OTHER INFORMATION: Synthetic

<400> SEQUENCE: 35
atgttcaagg accccaagcg gctgtactgc aaaaacgggg cttcttcct gcgcatccac    60 cccgacggcc gagttgacgg ggtccgggag aagagcgacc ctcacatcaa gctacaactt   120
caagcagaag agaggagt tgtgtctatc aaggagtgt gtgctaaccg ttacctggct    180
atgaaggaag atggaagatt actggcttct aaatgtgtta cggatgagtg ttcttttt    240 gaacgattgg aatctaataa ctacaatact taccggtcaa ggaaatacac cagttggtat   300
gtggcactga acgaactgg gcagtataaa cttggatcca aaacaggacc tgggcagaaa   360
gctatacttt tcttccaat gtctgctaag agctga                             396

<210> SEQ ID NO 36
<211> LENGTH: 393
<212> TYPE: DNA
<213> ORGANISM: Artificial
<220> FEATURE:
<223> OTHER INFORMATION: Synthetic

<400> SEQUENCE: 36
atgaaggacc ccaagcggct gtactgcaaa aacggggct tcttcctgcg catccacccc    60
gacggccgag ttgacggggt ccgggagaag agcgaccctc acatcaagct acaacttcaa   120
gcagaagaga gaggagttgt gtctatcaaa ggagtgtgtg ctaaccgtta cctggctatg   180
aaggaagatg gaagattact ggcttctaaa tgtgttacgg atgagtgttt ctttttga    240 cgattggaat ctaataacta caatacttac cggtcaagga atacaccag ttggtatgtg   300 gcactgaaac gaactgggca gtataaactt ggatccaaaa caggacctgg gcagaaagct   360 atacttttc ttccaatgtc tgctaagagc tga                                393

<210> SEQ ID NO 37
<211> LENGTH: 390
<212> TYPE: DNA
<213> ORGANISM: Artificial
<220> FEATURE:
<223> OTHER INFORMATION: Synthetic

<400> SEQUENCE: 37
atggacccca gcggctgta ctgcaaaaac ggggcttct tcctgcgcat ccaccccgac     60
ggccgagttg acggggtccg ggagaagagc gaccctcaca tcaagctaca acttcaagca   120
gaagagagag agttgtgtc tatcaaagga gtgtgtgcta accgttacct ggctatgaag   180
gaagatggaa gattactggc ttctaaatgt gttacggatg agtgtttctt ttttgaacga   240
```

```
ttggaatcta ataactacaa tacttaccgg tcaaggaaat acaccagttg gtatgtggca      300
ctgaaacgaa ctgggcagta taaacttgga tccaaaacag gacctgggca gaaagctata      360
ctttttcttc caatgtctgc taagagctga                                      390
```

<210> SEQ ID NO 38
<211> LENGTH: 387
<212> TYPE: DNA
<213> ORGANISM: Artificial
<220> FEATURE:
<223> OTHER INFORMATION: Synthetic

<400> SEQUENCE: 38

```
atgcccaagc ggctgtactg caaaaacggg ggcttcttcc tgcgcatcca ccccgacggc       60
cgagttgacg gggtccggga gaagagcgac cctcacatca agctacaact tcaagcagaa      120
gagagaggag ttgtgtctat caaggagtgt gtgctaaccg ttacctggc tatgaaggaa       180 gatggaagat tactggcttc taaatgtgtt acggatgagt gtttcttttt tgaacgattg      240
gaatctaata actacaatac ttaccggtca aggaaataca ccagttggta tgtggcactg      300
aaacgaactg ggcagtataa acttggatcc aaaacaggac ctgggcagaa agctatactt     360
tttcttccaa tgtctgctaa gagctga                                         387
```

<210> SEQ ID NO 39
<211> LENGTH: 384
<212> TYPE: DNA
<213> ORGANISM: Artificial
<220> FEATURE:
<223> OTHER INFORMATION: Synthetic

<400> SEQUENCE: 39

```
atgaagcggc tgtactgcaa aaacgggggc ttcttcctgc gcatccaccc cgacggccga       60
gttgacgggg tccgggagaa gagcgaccct cacatcaagc tacaacttca agcagaagag     120
agaggagttg tgtctatcaa ggagtgtgt gctaaccgtt acctggctat gaaggaagat      180
ggaagattac tggcttctaa atgtgttacg gatgagtgtt ctttttttga acgattggaa     240
tctaataact acaatactta ccggtcaagg aaatacacca gttggtatgt ggcactgaaa     300
cgaactgggc agtataaact tggatccaaa acaggacctg gcagaaagc tatactttt      360 cttccaatgt ctgctaagag ctga                                            384
```

<210> SEQ ID NO 40
<211> LENGTH: 381
<212> TYPE: DNA
<213> ORGANISM: Artificial
<220> FEATURE:
<223> OTHER INFORMATION: Synthetic

<400> SEQUENCE: 40

```
atgcggctgt actgcaaaaa cgggggcttc ttcctgcgca tccaccccga cggccgagtt       60
gacggggtcc gggagaagag cgaccctcac atcaagctac aacttcaagc agaagagaga     120
ggagttgtgt ctatcaaagg agtgtgtgct aaccgttacc tggctatgaa ggaagatgga     180
agattactgg cttctaaatg tgttacggat gagtgtttct tttttgaacg attggaatct     240
aataactaca atacttaccg gtcaaggaaa tacaccagtt ggtatgtggc actgaaacga     300
actgggcagt ataaacttgg atccaaaaca ggacctgggc agaaagctat acttttcctt    360
ccaatgtctg ctaagagctg a                                               381
```

<210> SEQ ID NO 41
<211> LENGTH: 381
<212> TYPE: DNA
<213> ORGANISM: Artificial
<220> FEATURE:
<223> OTHER INFORMATION: Synthetic

<400> SEQUENCE: 41

```
atgcggctgt actgcaaaaa cgggggcttc ttcctgcgca tccacccga cggccgagtt      60
gacgggtcc gggagaagag cgaccctcac atcaagctac aacttcaagc agaagagaga     120
ggagttgtgt ctatcaaagg agtgtgtgct aaccgttacc tggctatgaa ggaagatgga     180
agattactgg cttctaaatg tgttacggat gagtgtttct tttttgaacg attggaatct     240
aataactaca atacttaccg gtcaaggaaa tacaccagtt ggtatgtggc actgaaacga     300
actgggcagt ataaacttgg atccaaaaca ggacctgggc agaaagctat acttttttctt   360
ccaatgtctg ctaagagctg a                                               381
```

<210> SEQ ID NO 42
<211> LENGTH: 393
<212> TYPE: DNA
<213> ORGANISM: Artificial
<220> FEATURE:
<223> OTHER INFORMATION: Synthetic

<400> SEQUENCE: 42

```
atgaaggacc ccaagcggct gtactgcaaa acgggggct tcttcctgcg catccacccc      60
gacggccgag ttgacggggt ccgggagaag agcgaccctc acatcaagct acaacttcaa    120
gcagaagaga gaggagttgt gtctatcaaa ggagtgtgtg ctaaccgtta cctggctatg    180
aaggaagatg gaagattact ggcttctaaa tgtgttacgg atgagtgttt ctttttttgaa   240
cgattggaat ctaaggccta caatacttac cggtcaagga aatacaccag ttggtatgtg    300
gcactgaaac gaactgggca gtataaactt ggatccaaaa caggacctgg gcagaaagct    360
atactttttc ttccaatgtc tgctaagagc tga                                 393
```

<210> SEQ ID NO 43
<211> LENGTH: 399
<212> TYPE: DNA
<213> ORGANISM: Artificial
<220> FEATURE:
<223> OTHER INFORMATION: Synthetic

<400> SEQUENCE: 43

```
atggatttca aggaccccaa gcggctgtac tgcaaaaacg ggggcttctt cctgcgcatc      60
caccccgacg gccgagttga cggggtccgg gagaagagcg accctcacat caagctacaa    120
cttcaagcag aagagagagg agttgtgtct atcaaaggag tgtgtgctaa ccgttacctg    180
gctatgaagg aagatggaag attactggct tctaaatgtg ttacggatga gtgtttcttt    240
tttgaacgat tggaatctaa taactacaat acttaccggt caaggaaata caccagttgg    300
tatgtggcac tgaaacgaac tgggcagtat aaacttggat ccaaaacagg acctgggcag    360
aaagctatac ttttttcttcc aatgtctgct aagagctga                           399
```

<210> SEQ ID NO 44
<211> LENGTH: 399
<212> TYPE: DNA
<213> ORGANISM: Artificial
<220> FEATURE:
<223> OTHER INFORMATION: Synthetic

<400> SEQUENCE: 44

```
atgcagttca aggaccccaa gcggctgtac tgcaaaaacg ggggcttctt cctgcgcatc    60
caccccgacg gccgagttga cggggtccgg gagaagagcg accctcacat caagctacaa   120
cttcaagcag aagagagagg agttgtgtct atcaaaggag tgtgtgctaa ccgttacctg   180
gctatgaagg aagatggaag attactggct tctaaatgtg ttacggatga gtgtttcttt   240
tttgaacgat tggaatctaa taactacaat acttaccggt caaggaaata caccagttgg   300
tatgtggcac tgaaacgaac tgggcagtat aaacttggat ccaaaacagg acctgggcag   360
aaagctatac tttttcttcc aatgtctgct aagagctga                          399
```

<210> SEQ ID NO 45
<211> LENGTH: 399
<212> TYPE: DNA
<213> ORGANISM: Artificial
<220> FEATURE:
<223> OTHER INFORMATION: Synthetic

<400> SEQUENCE: 45

```
atggtgttca aggaccccaa gcggctgtac tgcaaaaacg ggggcttctt cctgcgcatc    60
caccccgacg gccgagttga cggggtccgg gagaagagcg accctcacat caagctacaa   120
cttcaagcag aagagagagg agttgtgtct atcaaaggag tgtgtgctaa ccgttacctg   180
gctatgaagg aagatggaag attactggct tctaaatgtg ttacggatga gtgtttcttt   240
tttgaacgat tggaatctaa taactacaat acttaccggt caaggaaata caccagttgg   300
tatgtggcac tgaaacgaac tgggcagtat aaacttggat ccaaaacagg acctgggcag   360
aaagctatac tttttcttcc aatgtctgct aagagctga                          399
```

<210> SEQ ID NO 46
<211> LENGTH: 399
<212> TYPE: DNA
<213> ORGANISM: Artificial
<220> FEATURE:
<223> OTHER INFORMATION: Synthetic

<400> SEQUENCE: 46

```
atgaaattca aggaccccaa gcggctgtac tgcaaaaacg ggggcttctt cctgcgcatc    60
caccccgacg gccgagttga cggggtccgg gagaagagcg accctcacat caagctacaa   120
cttcaagcag aagagagagg agttgtgtct atcaaaggag tgtgtgctaa ccgttacctg   180
gctatgaagg aagatggaag attactggct tctaaatgtg ttacggatga gtgtttcttt   240
tttgaacgat tggaatctaa taactacaat acttaccggt caaggaaata caccagttgg   300
tatgtggcac tgaaacgaac tgggcagtat aaacttggat ccaaaacagg acctgggcag   360
aaagctatac tttttcttcc aatgtctgct aagagctga                          399
```

<210> SEQ ID NO 47
<211> LENGTH: 399
<212> TYPE: DNA
<213> ORGANISM: Artificial
<220> FEATURE:
<223> OTHER INFORMATION: Synthetic

<400> SEQUENCE: 47

```
atgcacgata aggaccccaa gcggctgtac tgcaaaaacg ggggcttctt cctgcgcatc    60
caccccgacg gccgagttga cggggtccgg gagaagagcg accctcacat caagctacaa   120
```

```
cttcaagcag aagagagagg agttgtgtct atcaaaggag tgtgtgctaa ccgttacctg      180
gctatgaagg aagatggaag attactggct tctaaatgtg ttacggatga gtgtttcttt      240
tttgaacgat tggaatctaa taactacaat acttaccggt caaggaaata caccagttgg      300
tatgtggcac tgaaacgaac tgggcagtat aaacttggat ccaaaacagg acctgggcag      360
aaagctatac ttttctttcc aatgtctgct aagagctga                             399

<210> SEQ ID NO 48
<211> LENGTH: 399
<212> TYPE: DNA
<213> ORGANISM: Artificial
<220> FEATURE:
<223> OTHER INFORMATION: Synthetic

<400> SEQUENCE: 48
atgcaccaga aggaccccaa gcggctgtac tgcaaaaacg ggggcttctt cctgcgcatc       60
caccccgacg gccgagttga cggggtccgg gagaagagcg accctcacat caagctacaa      120
cttcaagcag aagagagagg agttgtgtct atcaaaggag tgtgtgctaa ccgttacctg      180
gctatgaagg aagatggaag attactggct tctaaatgtg ttacggatga gtgtttcttt      240
tttgaacgat tggaatctaa taactacaat acttaccggt caaggaaata caccagttgg      300
tatgtggcac tgaaacgaac tgggcagtat aaacttggat ccaaaacagg acctgggcag      360
aaagctatac ttttctttcc aatgtctgct aagagctga                             399

<210> SEQ ID NO 49
<211> LENGTH: 399
<212> TYPE: DNA
<213> ORGANISM: Artificial
<220> FEATURE:
<223> OTHER INFORMATION: Synthetic

<400> SEQUENCE: 49
atgcacaaaa aggaccccaa gcggctgtac tgcaaaaacg ggggcttctt cctgcgcatc       60
caccccgacg gccgagttga cggggtccgg gagaagagcg accctcacat caagctacaa      120
cttcaagcag aagagagagg agttgtgtct atcaaaggag tgtgtgctaa ccgttacctg      180
gctatgaagg aagatggaag attactggct tctaaatgtg ttacggatga gtgtttcttt      240
tttgaacgat tggaatctaa taactacaat acttaccggt caaggaaata caccagttgg      300
tatgtggcac tgaaacgaac tgggcagtat aaacttggat ccaaaacagg acctgggcag      360
aaagctatac ttttctttcc aatgtctgct aagagctga                             399

<210> SEQ ID NO 50
<211> LENGTH: 399
<212> TYPE: DNA
<213> ORGANISM: Artificial
<220> FEATURE:
<223> OTHER INFORMATION: Synthetic

<400> SEQUENCE: 50
atgcactata aggaccccaa gcggctgtac tgcaaaaacg ggggcttctt cctgcgcatc       60
caccccgacg gccgagttga cggggtccgg gagaagagcg accctcacat caagctacaa      120
cttcaagcag aagagagagg agttgtgtct atcaaaggag tgtgtgctaa ccgttacctg      180
gctatgaagg aagatggaag attactggct tctaaatgtg ttacggatga gtgtttcttt      240
tttgaacgat tggaatctaa taactacaat acttaccggt caaggaaata caccagttgg      300
tatgtggcac tgaaacgaac tgggcagtat aaacttggat ccaaaacagg acctgggcag      360
```

```
aaagctatac tttttcttcc aatgtctgct aagagctga                        399
```

<210> SEQ ID NO 51
<211> LENGTH: 399
<212> TYPE: DNA
<213> ORGANISM: Artificial
<220> FEATURE:
<223> OTHER INFORMATION: Synthetic

<400> SEQUENCE: 51

```
atggatgata aggaccccaa gcggctgtac tgcaaaaacg ggggcttctt cctgcgcatc     60
caccccgacg gccgagttga cggggtccgg gagaagagcg accctcacat caagctacaa    120
cttcaagcag aagagagagg agttgtgtct atcaaaggag tgtgtgctaa ccgttacctg    180
gctatgaagg aagatggaag attactggct tctaaatgtg ttacggatga gtgtttcttt    240
tttgaacgat tggaatctaa taactacaat acttaccggt caaggaaata caccagttgg    300
tatgtggcac tgaaacgaac tgggcagtat aaacttggat ccaaaacagg acctgggcag    360
aaagctatac tttttcttcc aatgtctgct aagagctga                          399
```

<210> SEQ ID NO 52
<211> LENGTH: 399
<212> TYPE: DNA
<213> ORGANISM: Artificial
<220> FEATURE:
<223> OTHER INFORMATION: Synthetic

<400> SEQUENCE: 52

```
atggatcaga aggaccccaa gcggctgtac tgcaaaaacg ggggcttctt cctgcgcatc     60
caccccgacg gccgagttga cggggtccgg gagaagagcg accctcacat caagctacaa    120
cttcaagcag aagagagagg agttgtgtct atcaaaggag tgtgtgctaa ccgttacctg    180
gctatgaagg aagatggaag attactggct tctaaatgtg ttacggatga gtgtttcttt    240
tttgaacgat tggaatctaa taactacaat acttaccggt caaggaaata caccagttgg    300
tatgtggcac tgaaacgaac tgggcagtat aaacttggat ccaaaacagg acctgggcag    360
aaagctatac tttttcttcc aatgtctgct aagagctga                          399
```

<210> SEQ ID NO 53
<211> LENGTH: 399
<212> TYPE: DNA
<213> ORGANISM: Artificial
<220> FEATURE:
<223> OTHER INFORMATION: Synthetic

<400> SEQUENCE: 53

```
atggataaaa aggaccccaa gcggctgtac tgcaaaaacg ggggcttctt cctgcgcatc     60
caccccgacg gccgagttga cggggtccgg gagaagagcg accctcacat caagctacaa    120
cttcaagcag aagagagagg agttgtgtct atcaaaggag tgtgtgctaa ccgttacctg    180
gctatgaagg aagatggaag attactggct tctaaatgtg ttacggatga gtgtttcttt    240
tttgaacgat tggaatctaa taactacaat acttaccggt caaggaaata caccagttgg    300
tatgtggcac tgaaacgaac tgggcagtat aaacttggat ccaaaacagg acctgggcag    360
aaagctatac tttttcttcc aatgtctgct aagagctga                          399
```

<210> SEQ ID NO 54
<211> LENGTH: 399
<212> TYPE: DNA

<213> ORGANISM: Artificial
<220> FEATURE:
<223> OTHER INFORMATION: Synthetic

<400> SEQUENCE: 54

```
atgcaggata aggaccccaa gcggctgtac tgcaaaaacg ggggcttctt cctgcgcatc    60
caccccgacg gccgagttga cggggtccgg gagaagagcg accctcacat caagctacaa   120
cttcaagcag aagagagagg agttgtgtct atcaaaggag tgtgtgctaa ccgttacctg   180
gctatgaagg aagatggaag attactggct tctaaatgtg ttacggatga gtgtttcttt   240
tttgaacgat tggaatctaa taactacaat acttaccggt caaggaaata caccagttgg   300
tatgtggcac tgaaacgaac tggcagtat  aaacttggat ccaaaacagg acctgggcag   360
aaagctatac tttttcttcc aatgtctgct aagagctga                          399
```

<210> SEQ ID NO 55
<211> LENGTH: 399
<212> TYPE: DNA
<213> ORGANISM: Artificial
<220> FEATURE:
<223> OTHER INFORMATION: Synthetic

<400> SEQUENCE: 55

```
atgcagaaaa aggaccccaa gcggctgtac tgcaaaaacg ggggcttctt cctgcgcatc    60
caccccgacg gccgagttga cggggtccgg gagaagagcg accctcacat caagctacaa   120
cttcaagcag aagagagagg agttgtgtct atcaaaggag tgtgtgctaa ccgttacctg   180
gctatgaagg aagatggaag attactggct tctaaatgtg ttacggatga gtgtttcttt   240
tttgaacgat tggaatctaa taactacaat acttaccggt caaggaaata caccagttgg   300
tatgtggcac tgaaacgaac tggcagtat  aaacttggat ccaaaacagg acctgggcag   360
aaagctatac tttttcttcc aatgtctgct aagagctga                          399
```

<210> SEQ ID NO 56
<211> LENGTH: 399
<212> TYPE: DNA
<213> ORGANISM: Artificial
<220> FEATURE:
<223> OTHER INFORMATION: Synthetic

<400> SEQUENCE: 56

```
atggtggata aggaccccaa gcggctgtac tgcaaaaacg ggggcttctt cctgcgcatc    60
caccccgacg gccgagttga cggggtccgg gagaagagcg accctcacat caagctacaa   120
cttcaagcag aagagagagg agttgtgtct atcaaaggag tgtgtgctaa ccgttacctg   180
gctatgaagg aagatggaag attactggct tctaaatgtg ttacggatga gtgtttcttt   240
tttgaacgat tggaatctaa taactacaat acttaccggt caaggaaata caccagttgg   300
tatgtggcac tgaaacgaac tggcagtat  aaacttggat ccaaaacagg acctgggcag   360
aaagctatac tttttcttcc aatgtctgct aagagctga                          399
```

<210> SEQ ID NO 57
<211> LENGTH: 399
<212> TYPE: DNA
<213> ORGANISM: Artificial
<220> FEATURE:
<223> OTHER INFORMATION: Synthetic

<400> SEQUENCE: 57

```
atggtgcaga aggaccccaa gcggctgtac tgcaaaaacg ggggcttctt cctgcgcatc    60
```

```
caccccgacg gccgagttga cggggtccgg gagaagagcg accctcacat caagctacaa    120
cttcaagcag aagagagagg agttgtgtct atcaaaggat gtgtgctaac cgttacctg    180 gctatgaagg aagatggaag attactggct tctaaatgtg ttacggatga gtgtttcttt    240
tttgaacgat tggaatctaa taactacaat acttaccggt caaggaaata caccagttgg    300
tatgtggcac tgaaacgaac tgggcagtat aaacttggat ccaaaacagg acctgggcag    360
aaagctatac tttttcttcc aatgtctgct aagagctga                          399
```

<210> SEQ ID NO 58
<211> LENGTH: 399
<212> TYPE: DNA
<213> ORGANISM: Artificial
<220> FEATURE:
<223> OTHER INFORMATION: Synthetic

<400> SEQUENCE: 58

```
atggtgaaaa aggaccccaa gcggctgtac tgcaaaaacg ggggcttctt cctgcgcatc     60
caccccgacg gccgagttga cggggtccgg gagaagagcg accctcacat caagctacaa    120
cttcaagcag aagagagagg agttgtgtct atcaaaggat gtgtgctaac cgttacctg    180 gctatgaagg aagatggaag attactggct tctaaatgtg ttacggatga gtgtttcttt    240
tttgaacgat tggaatctaa taactacaat acttaccggt caaggaaata caccagttgg    300
tatgtggcac tgaaacgaac tgggcagtat aaacttggat ccaaaacagg acctgggcag    360
aaagctatac tttttcttcc aatgtctgct aagagctga                          399
```

<210> SEQ ID NO 59
<211> LENGTH: 399
<212> TYPE: DNA
<213> ORGANISM: Artificial
<220> FEATURE:
<223> OTHER INFORMATION: Synthetic

<400> SEQUENCE: 59

```
atgaaacaga aggaccccaa gcggctgtac tgcaaaaacg ggggcttctt cctgcgcatc     60
caccccgacg gccgagttga cggggtccgg gagaagagcg accctcacat caagctacaa    120
cttcaagcag aagagagagg agttgtgtct atcaaaggag tgtgtgctaa ccgttacctg    180
gctatgaagg aagatggaag attactggct tctaaatgtg ttacggatga gtgtttcttt    240
tttgaacgat tggaatctaa taactacaat acttaccggt caaggaaata caccagttgg    300
tatgtggcac tgaaacgaac tgggcagtat aaacttggat ccaaaacagg acctgggcag    360
aaagctatac tttttcttcc aatgtctgct aagagctga                          399
```

<210> SEQ ID NO 60
<211> LENGTH: 134
<212> TYPE: PRT
<213> ORGANISM: Artificial
<220> FEATURE:
<223> OTHER INFORMATION: Synthetic

<400> SEQUENCE: 60

Ala Gly Asp Tyr Leu Leu Gly Ile Lys Arg Leu Arg Arg Leu Tyr Cys
1               5                   10                  15

Asn Val Gly Ile Gly Phe His Leu Gln Ala Leu Pro Asp Gly Arg Ile
            20                  25                  30

Gly Gly Ala His Ala Asp Thr Arg Asp Ser Leu Leu Glu Leu Ser Pro
        35                  40                  45

Val Glu Arg Gly Val Val Ser Ile Phe Gly Val Ala Ser Arg Phe Phe
 50                  55                  60

Val Ala Met Ser Ser Lys Gly Lys Leu Tyr Gly Ser Pro Phe Phe Thr
 65                  70                  75                  80

Asp Glu Cys Thr Phe Lys Glu Ile Leu Leu Pro Asn Asn Tyr Asn Ala
                 85                  90                  95

Tyr Glu Ser Tyr Lys Tyr Pro Gly Met Phe Ile Ala Leu Ser Lys Asn
                100                 105                 110

Gly Lys Thr Lys Lys Gly Asn Arg Val Ser Pro Thr Met Lys Val Thr
            115                 120                 125

His Phe Leu Pro Arg Leu
    130

<210> SEQ ID NO 61
<211> LENGTH: 133
<212> TYPE: PRT
<213> ORGANISM: Artificial
<220> FEATURE:
<223> OTHER INFORMATION: Synthetic

<400> SEQUENCE: 61

Gly Asp Tyr Leu Leu Gly Ile Lys Arg Leu Arg Arg Leu Tyr Cys Asn
 1               5                  10                  15

Val Gly Ile Gly Phe His Leu Gln Ala Leu Pro Asp Gly Arg Ile Gly
                 20                  25                  30

Gly Ala His Ala Asp Thr Arg Asp Ser Leu Leu Glu Leu Ser Pro Val
             35                  40                  45

Glu Arg Gly Val Val Ser Ile Phe Gly Val Ala Ser Arg Phe Phe Val
 50                  55                  60

Ala Met Ser Ser Lys Gly Lys Leu Tyr Gly Ser Pro Phe Phe Thr Asp
 65                  70                  75                  80

Glu Cys Thr Phe Lys Glu Ile Leu Leu Pro Asn Asn Tyr Asn Ala Tyr
                 85                  90                  95

Glu Ser Tyr Lys Tyr Pro Gly Met Phe Ile Ala Leu Ser Lys Asn Gly
                100                 105                 110

Lys Thr Lys Lys Gly Asn Arg Val Ser Pro Thr Met Lys Val Thr His
            115                 120                 125

Phe Leu Pro Arg Leu
    130

<210> SEQ ID NO 62
<211> LENGTH: 132
<212> TYPE: PRT
<213> ORGANISM: Artificial
<220> FEATURE:
<223> OTHER INFORMATION: Synthetic

<400> SEQUENCE: 62

Asp Tyr Leu Leu Gly Ile Lys Arg Leu Arg Arg Leu Tyr Cys Asn Val
 1               5                  10                  15

Gly Ile Gly Phe His Leu Gln Ala Leu Pro Asp Gly Arg Ile Gly Gly
                 20                  25                  30

Ala His Ala Asp Thr Arg Asp Ser Leu Leu Glu Leu Ser Pro Val Glu
             35                  40                  45

Arg Gly Val Val Ser Ile Phe Gly Val Ala Ser Arg Phe Phe Val Ala
 50                  55                  60

Met Ser Ser Lys Gly Lys Leu Tyr Gly Ser Pro Phe Phe Thr Asp Glu

```
                65                  70                  75                  80
Cys Thr Phe Lys Glu Ile Leu Leu Pro Asn Asn Tyr Asn Ala Tyr Glu
                        85                  90                  95
Ser Tyr Lys Tyr Pro Gly Met Phe Ile Ala Leu Ser Lys Asn Gly Lys
                        100                 105                 110
Thr Lys Lys Gly Asn Arg Val Ser Pro Thr Met Lys Val Thr His Phe
                        115                 120                 125
Leu Pro Arg Leu
            130
```

<210> SEQ ID NO 63
<211> LENGTH: 131
<212> TYPE: PRT
<213> ORGANISM: Artificial
<220> FEATURE:
<223> OTHER INFORMATION: Synthetic

<400> SEQUENCE: 63

```
Tyr Leu Leu Gly Ile Lys Arg Leu Arg Arg Leu Tyr Cys Asn Val Gly
1               5                   10                  15
Ile Gly Phe His Leu Gln Ala Leu Pro Asp Gly Arg Ile Gly Gly Ala
                20                  25                  30
His Ala Asp Thr Arg Asp Ser Leu Leu Glu Leu Ser Pro Val Glu Arg
                35                  40                  45
Gly Val Val Ser Ile Phe Gly Val Ala Ser Arg Phe Phe Val Ala Met
            50                  55                  60
Ser Ser Lys Gly Lys Leu Tyr Gly Ser Pro Phe Phe Thr Asp Glu Cys
65              70                  75                  80
Thr Phe Lys Glu Ile Leu Leu Pro Asn Asn Tyr Asn Ala Tyr Glu Ser
                        85                  90                  95
Tyr Lys Tyr Pro Gly Met Phe Ile Ala Leu Ser Lys Asn Gly Lys Thr
                        100                 105                 110
Lys Lys Gly Asn Arg Val Ser Pro Thr Met Lys Val Thr His Phe Leu
                        115                 120                 125
Pro Arg Leu
        130
```

<210> SEQ ID NO 64
<211> LENGTH: 130
<212> TYPE: PRT
<213> ORGANISM: Artificial
<220> FEATURE:
<223> OTHER INFORMATION: Synthetic

<400> SEQUENCE: 64

```
Leu Leu Gly Ile Lys Arg Leu Arg Arg Leu Tyr Cys Asn Val Gly Ile
1               5                   10                  15
Gly Phe His Leu Gln Ala Leu Pro Asp Gly Arg Ile Gly Gly Ala His
                20                  25                  30
Ala Asp Thr Arg Asp Ser Leu Leu Glu Leu Ser Pro Val Glu Arg Gly
                35                  40                  45
Val Val Ser Ile Phe Gly Val Ala Ser Arg Phe Phe Val Ala Met Ser
            50                  55                  60
Ser Lys Gly Lys Leu Tyr Gly Ser Pro Phe Phe Thr Asp Glu Cys Thr
65              70                  75                  80
Phe Lys Glu Ile Leu Leu Pro Asn Asn Tyr Asn Ala Tyr Glu Ser Tyr
                        85                  90                  95
```

```
Lys Tyr Pro Gly Met Phe Ile Ala Leu Ser Lys Asn Gly Lys Thr Lys
            100                 105                 110

Lys Gly Asn Arg Val Ser Pro Thr Met Lys Val Thr His Phe Leu Pro
        115                 120                 125

Arg Leu
    130

<210> SEQ ID NO 65
<211> LENGTH: 129
<212> TYPE: PRT
<213> ORGANISM: Artificial
<220> FEATURE:
<223> OTHER INFORMATION: Synthetic

<400> SEQUENCE: 65

Leu Gly Ile Lys Arg Leu Arg Arg Leu Tyr Cys Asn Val Gly Ile Gly
1               5                   10                  15

Phe His Leu Gln Ala Leu Pro Asp Gly Arg Ile Gly Gly Ala His Ala
            20                  25                  30

Asp Thr Arg Asp Ser Leu Leu Glu Leu Ser Pro Val Glu Arg Gly Val
        35                  40                  45

Val Ser Ile Phe Gly Val Ala Ser Arg Phe Phe Val Ala Met Ser Ser
    50                  55                  60

Lys Gly Lys Leu Tyr Gly Ser Pro Phe Phe Thr Asp Glu Cys Thr Phe
65                  70                  75                  80

Lys Glu Ile Leu Leu Pro Asn Asn Tyr Asn Ala Tyr Glu Ser Tyr Lys
                85                  90                  95

Tyr Pro Gly Met Phe Ile Ala Leu Ser Lys Asn Gly Lys Thr Lys Lys
            100                 105                 110

Gly Asn Arg Val Ser Pro Thr Met Lys Val Thr His Phe Leu Pro Arg
        115                 120                 125

Leu

<210> SEQ ID NO 66
<211> LENGTH: 128
<212> TYPE: PRT
<213> ORGANISM: Artificial
<220> FEATURE:
<223> OTHER INFORMATION: Synthetic

<400> SEQUENCE: 66

Gly Ile Lys Arg Leu Arg Arg Leu Tyr Cys Asn Val Gly Ile Gly Phe
1               5                   10                  15

His Leu Gln Ala Leu Pro Asp Gly Arg Ile Gly Gly Ala His Ala Asp
            20                  25                  30

Thr Arg Asp Ser Leu Leu Glu Leu Ser Pro Val Glu Arg Gly Val Val
        35                  40                  45

Ser Ile Phe Gly Val Ala Ser Arg Phe Phe Val Ala Met Ser Ser Lys
    50                  55                  60

Gly Lys Leu Tyr Gly Ser Pro Phe Phe Thr Asp Glu Cys Thr Phe Lys
65                  70                  75                  80

Glu Ile Leu Leu Pro Asn Asn Tyr Asn Ala Tyr Glu Ser Tyr Lys Tyr
                85                  90                  95

Pro Gly Met Phe Ile Ala Leu Ser Lys Asn Gly Lys Thr Lys Lys Gly
            100                 105                 110

Asn Arg Val Ser Pro Thr Met Lys Val Thr His Phe Leu Pro Arg Leu
        115                 120                 125
```

<210> SEQ ID NO 67
<211> LENGTH: 127
<212> TYPE: PRT
<213> ORGANISM: Artificial
<220> FEATURE:
<223> OTHER INFORMATION: Synthetic

<400> SEQUENCE: 67

Ile Lys Arg Leu Arg Arg Leu Tyr Cys Asn Val Gly Ile Gly Phe His
1               5                   10                  15

Leu Gln Ala Leu Pro Asp Gly Arg Ile Gly Gly Ala His Ala Asp Thr
            20                  25                  30

Arg Asp Ser Leu Leu Glu Leu Ser Pro Val Glu Arg Gly Val Val Ser
        35                  40                  45

Ile Phe Gly Val Ala Ser Arg Phe Phe Val Ala Met Ser Ser Lys Gly
50                  55                  60

Lys Leu Tyr Gly Ser Pro Phe Phe Thr Asp Glu Cys Thr Phe Lys Glu
65                  70                  75                  80

Ile Leu Leu Pro Asn Asn Tyr Asn Ala Tyr Glu Ser Tyr Lys Tyr Pro
                85                  90                  95

Gly Met Phe Ile Ala Leu Ser Lys Asn Gly Lys Thr Lys Lys Gly Asn
            100                 105                 110

Arg Val Ser Pro Thr Met Lys Val Thr His Phe Leu Pro Arg Leu
        115                 120                 125

<210> SEQ ID NO 68
<211> LENGTH: 126
<212> TYPE: PRT
<213> ORGANISM: Artificial
<220> FEATURE:
<223> OTHER INFORMATION: Synthetic

<400> SEQUENCE: 68

Lys Arg Leu Arg Arg Leu Tyr Cys Asn Val Gly Ile Gly Phe His Leu
1               5                   10                  15

Gln Ala Leu Pro Asp Gly Arg Ile Gly Gly Ala His Ala Asp Thr Arg
            20                  25                  30

Asp Ser Leu Leu Glu Leu Ser Pro Val Glu Arg Gly Val Val Ser Ile
        35                  40                  45

Phe Gly Val Ala Ser Arg Phe Phe Val Ala Met Ser Ser Lys Gly Lys
50                  55                  60

Leu Tyr Gly Ser Pro Phe Phe Thr Asp Glu Cys Thr Phe Lys Glu Ile
65                  70                  75                  80

Leu Leu Pro Asn Asn Tyr Asn Ala Tyr Glu Ser Tyr Lys Tyr Pro Gly
                85                  90                  95

Met Phe Ile Ala Leu Ser Lys Asn Gly Lys Thr Lys Lys Gly Asn Arg
            100                 105                 110

Val Ser Pro Thr Met Lys Val Thr His Phe Leu Pro Arg Leu
        115                 120                 125

<210> SEQ ID NO 69
<211> LENGTH: 408
<212> TYPE: DNA
<213> ORGANISM: Artificial
<220> FEATURE:
<223> OTHER INFORMATION: Synthetic

<400> SEQUENCE: 69
atggccggcg actacctgct gggcatcaag cggctgcggc ggctctactg caacgtgggc    60

```
atcggcttcc acctccaggc gctccccgac ggccgcatcg gcggcgcgca cgcggacacc    120
cgcgacagcc tgctggagct ctcgcccgtg gagcggggcg tggtgagcat cttcggcgtg    180
gccagccggt tcttcgtggc catgagcagc aagggcaagc tctatggctc gcccttcttc    240
accgatgagt gcacgttcaa ggagattctc cttcccaaca actacaacgc ctacgagtcc    300
tacaagtacc ccggcatgtt catcgccctg agcaagaatg ggaagaccaa gaagggggaac   360 cgagtgtcgc ccaccatgaa ggtcacccac ttcctcccca ggctgtga                 408

<210> SEQ ID NO 70
<211> LENGTH: 405
<212> TYPE: DNA
<213> ORGANISM: Artificial
<220> FEATURE:
<223> OTHER INFORMATION: Synthetic

<400> SEQUENCE: 70
atgggcgact acctgctggg catcaagcgg ctgcggcggc tctactgcaa cgtgggcatc    60
ggcttccacc tccaggcgct ccccgacggc cgcatcggcg cgcgcacgc ggacacccgc    120 gacagcctgc tggagctctc gcccgtggag cggggcgtgg tgagcatctt cggcgtggcc    180
agccggttct tcgtggccat gagcagcaag ggcaagctct atggctcgcc cttcttcacc    240
gatgagtgca cgttcaagga gattctcctt cccaacaact acaacgccta cgagtcctac    300
aagtaccccg gcatgttcat cgccctgagc aagaatggga agaccaagaa ggggaaccga    360
gtgtcgccca ccatgaaggt cacccacttc ctccccaggc tgtga                   405

<210> SEQ ID NO 71
<211> LENGTH: 402
<212> TYPE: DNA
<213> ORGANISM: Artificial
<220> FEATURE:
<223> OTHER INFORMATION: Synthetic

<400> SEQUENCE: 71
atggactacc tgctgggcat caagcggctg cggcggctct actgcaacgt gggcatcggc    60
ttccacctcc aggcgctccc cgacggccgc atcggcggcg cgcacgcgga cacccgcgac    120
agcctgctgg agctctcgcc cgtggagcgg ggcgtggtga gcatcttcgg cgtggccagc    180
cggttcttcg tggccatgag cagcaagggc aagctctatg gctcgccctt cttcaccgat    240
gagtgcacgt tcaaggagat tctccttccc aacaactaca acgcctacga gtcctacaag    300
taccccggca tgttcatcgc cctgagcaag aatgggaaga ccaagaaggg gaaccgagtg    360
tcgcccacca tgaaggtcac ccacttcctc cccaggctgt ga                      402

<210> SEQ ID NO 72
<211> LENGTH: 399
<212> TYPE: DNA
<213> ORGANISM: Artificial
<220> FEATURE:
<223> OTHER INFORMATION: Synthetic

<400> SEQUENCE: 72
atgtacctgc tgggcatcaa gcggctgcgg cggctctact gcaacgtggg catcggcttc    60
cacctccagg cgctccccga cggccgcatc ggcggcgcgc acgcggacac ccgcgacagc    120
ctgctggagc tctcgcccgt ggagcggggc gtggtgagca tcttcggcgt ggccagccgg    180
ttcttcgtgg ccatgagcag caagggcaag ctctatggct cgcccttctt caccgatgag    240
```

```
tgcacgttca aggagattct ccttcccaac aactacaacg cctacgagtc ctacaagtac    300
cccggcatgt tcatcgccct gagcaagaat gggaagacca agaaggggaa ccgagtgtcg    360
cccaccatga aggtcaccca cttcctcccc aggctgtga                           399
```

<210> SEQ ID NO 73
<211> LENGTH: 396
<212> TYPE: DNA
<213> ORGANISM: Artificial
<220> FEATURE:
<223> OTHER INFORMATION: Synthetic

<400> SEQUENCE: 73

```
atgctgctgg gcatcaagcg gctgcggcgg ctctactgca acgtgggcat cggcttccac     60
ctccaggcgc tccccgacgg ccgcatcggc ggcgcgcacg cggacacccg cgacagcctg    120
ctggagctct cgcccgtgga gcggggcgtg gtgagcatct cggcgtggc cagccggttc     180 ttcgtggcca tgagcagcaa gggcaagctc tatggctcgc ccttcttcac cgatgagtgc    240
acgttcaagg agattctcct tcccaacaac tacaacgcct acgagtccta caagtacccc    300
ggcatgttca tcgccctgag caagaatggg aagaccaaga ggggaaccg agtgtcgccc     360 accatgaagg tcacccactt cctccccagg ctgtga                              396
```

<210> SEQ ID NO 74
<211> LENGTH: 393
<212> TYPE: DNA
<213> ORGANISM: Artificial
<220> FEATURE:
<223> OTHER INFORMATION: Synthetic

<400> SEQUENCE: 74

```
atgctgggca tcaagcggct gcggcggctc tactgcaacg tgggcatcgg cttccacctc     60
caggcgctcc ccgacggccg catcggcggc gcgcacgcgg acacccgcga cagcctgctg    120
gagctctcgc ccgtggagcg gggcgtggtg agcatcttcg gcgtggccag ccggttcttc    180
gtggccatga gcagcaaggg caagctctat ggctcgccct tcttcaccga tgagtgcacg    240
ttcaaggaga ttctccttcc caacaactac aacgcctacg agtcctacaa gtaccccggc    300
atgttcatcg ccctgagcaa gaatgggaag accaagaagg ggaaccgagt gtcgcccacc    360
atgaaggtca cccacttcct ccccaggctg tga                                 393
```

<210> SEQ ID NO 75
<211> LENGTH: 390
<212> TYPE: DNA
<213> ORGANISM: Artificial
<220> FEATURE:
<223> OTHER INFORMATION: Synthetic

<400> SEQUENCE: 75

```
atgggcatca gcggctgcg gcggctctac tgcaacgtgg gcatcggctt ccacctccag      60
gcgctccccg acggccgcat cggcggcgcg cacgcggaca cccgcgacag cctgctggag    120
ctctcgcccg tggagcgggg cgtggtgagc atcttcggcg tggccagccg gttcttcgtg    180
gccatgagca gcaagggcaa gctctatggc tcgcccttct tcaccgatga gtgcacgttc    240
aaggagattc ccttcccaa caactacaac gcctacgagt cctacaagta ccccggcatg    300
ttcatcgccc tgagcaagaa tgggaagacc aagaagggga accgagtgtc gccaccatg    360 aaggtcaccc acttcctccc caggctgtga                                     390
```

```
<210> SEQ ID NO 76
<211> LENGTH: 387
<212> TYPE: DNA
<213> ORGANISM: Artificial
<220> FEATURE:
<223> OTHER INFORMATION: Synthetic

<400> SEQUENCE: 76
atgatcaagc ggctgcggcg gctctactgc aacgtgggca tcggcttcca cctccaggcg      60
ctccccgacg gccgcatcgg cggcgcgcac gcggacaccc gcgacagcct gctggagctc     120
tcgcccgtgg agcggggcgt ggtgagcatc ttcggcgtgg ccagccggtt cttcgtggcc     180
atgagcagca gggcaagct ctatggctcg cccttcttca ccgatgagtg cacgttcaag      240
gagattctcc ttcccaacaa ctacaacgcc tacgagtcct acaagtaccc cggcatgttc     300
atcgccctga gcaagaatgg aagaccaag aaggggaacc gagtgtcgcc caccatgaag      360
gtcacccact cctccccag gctgtga                                          387

<210> SEQ ID NO 77
<211> LENGTH: 384
<212> TYPE: DNA
<213> ORGANISM: Artificial
<220> FEATURE:
<223> OTHER INFORMATION: Synthetic

<400> SEQUENCE: 77
atgaagcggc tgcggcggct ctactgcaac gtgggcatcg gcttccacct ccaggcgctc      60
cccgacggcc gcatcggcgg cgcgcacgcg gacacccgcg acagcctgct ggagctctcg     120
cccgtggagc ggggcgtggt gagcatcttc ggcgtggcca gccggttctt cgtggccatg     180
agcagcaagg gcaagctcta tggctcgccc ttcttcaccg atgagtgcac gttcaaggag     240
attctccttc caacaacta caacgcctac gagtcctaca agtaccccgg catgttcatc      300
gccctgagca gaatgggaa gaccaagaag gggaaccgag tgtcgcccac catgaaggtc      360
acccacttcc tccccaggct gtga                                            384

<210> SEQ ID NO 78
<211> LENGTH: 31
<212> TYPE: DNA
<213> ORGANISM: Artificial
<220> FEATURE:
<223> OTHER INFORMATION: Synthetic

<400> SEQUENCE: 78
ggaattccat atgcacttca aggaccccaa g                                     31

<210> SEQ ID NO 79
<211> LENGTH: 30
<212> TYPE: DNA
<213> ORGANISM: Artificial
<220> FEATURE:
<223> OTHER INFORMATION: Synthetic

<400> SEQUENCE: 79
ggaattccat atgttcaagg accccaagcg                                       30

<210> SEQ ID NO 80
<211> LENGTH: 31
<212> TYPE: DNA
<213> ORGANISM: Artificial
<220> FEATURE:
<223> OTHER INFORMATION: Synthetic
```

<400> SEQUENCE: 80
ggaattccat atgaaggacc ccaagcggct g                                    31

<210> SEQ ID NO 81
<211> LENGTH: 34
<212> TYPE: DNA
<213> ORGANISM: Artificial
<220> FEATURE:
<223> OTHER INFORMATION: Synthetic

<400> SEQUENCE: 81
ggaattccat atgctgtact gcaaaaacgg gggc                                 34

<210> SEQ ID NO 82
<211> LENGTH: 32
<212> TYPE: DNA
<213> ORGANISM: Artificial
<220> FEATURE:
<223> OTHER INFORMATION: Synthetic

<400> SEQUENCE: 82
ggaattccat atggccggcg actacctgct gg                                   32

<210> SEQ ID NO 83
<211> LENGTH: 34
<212> TYPE: DNA
<213> ORGANISM: Artificial
<220> FEATURE:
<223> OTHER INFORMATION: Synthetic

<400> SEQUENCE: 83
ggaattccat atgggcgact acctgctggg catc                                 34

<210> SEQ ID NO 84
<211> LENGTH: 34
<212> TYPE: DNA
<213> ORGANISM: Artificial
<220> FEATURE:
<223> OTHER INFORMATION: Synthetic

<400> SEQUENCE: 84
ggaattccat atggactacc tgctgggcat caag                                 34

<210> SEQ ID NO 85
<211> LENGTH: 33
<212> TYPE: DNA
<213> ORGANISM: Artificial
<220> FEATURE:
<223> OTHER INFORMATION: Synthetic

<400> SEQUENCE: 85
ggaattccat atgtacctgc tgggcatcaa gcg                                  33

<210> SEQ ID NO 86
<211> LENGTH: 32
<212> TYPE: DNA
<213> ORGANISM: Artificial
<220> FEATURE:
<223> OTHER INFORMATION: Synthetic

<400> SEQUENCE: 86
ggaattccat atgctgctgg gcatcaagcg gc                                   32

<210> SEQ ID NO 87
<211> LENGTH: 32

<210> SEQ ID NO 87
<211> LENGTH: 32 (implied)
<212> TYPE: DNA
<213> ORGANISM: Artificial
<220> FEATURE:
<223> OTHER INFORMATION: Synthetic

<400> SEQUENCE: 87
ggaattccat atgctgggca tcaagcggct gc                                  32

<210> SEQ ID NO 88
<211> LENGTH: 22
<212> TYPE: DNA
<213> ORGANISM: Artificial
<220> FEATURE:
<223> OTHER INFORMATION: Synthetic

<400> SEQUENCE: 88
cgggatcctc agctcttagc ag                                             22

<210> SEQ ID NO 89
<211> LENGTH: 29
<212> TYPE: DNA
<213> ORGANISM: Artificial
<220> FEATURE:
<223> OTHER INFORMATION: Synthetic

<400> SEQUENCE: 89
cgggatcctc acagcctggg gaggaagtg                                      29

<210> SEQ ID NO 90
<211> LENGTH: 155
<212> TYPE: PRT
<213> ORGANISM: Artificial
<220> FEATURE:
<223> OTHER INFORMATION: Synthetic

<400> SEQUENCE: 90

Met Ala Ala Gly Ser Ile Thr Thr Leu Pro Ala Leu Pro Glu Asp Gly
1               5                   10                  15

Gly Ser Gly Ala Phe Pro Pro Gly His Gln Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 91
<211> LENGTH: 468
<212> TYPE: DNA
<213> ORGANISM: Artificial

```
<220> FEATURE:
<223> OTHER INFORMATION: Synthetic

<400> SEQUENCE: 91
atggcagccg ggagcatcac cacgctgccc gccttgcccg aggatggcgg cagcggcgcc      60
ttcccgcccg gccaccagaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact tttttcttcca atgtctgcta agagctga                468

<210> SEQ ID NO 92
<211> LENGTH: 6
<212> TYPE: PRT
<213> ORGANISM: Artificial
<220> FEATURE:
<223> OTHER INFORMATION: Synthetic

<400> SEQUENCE: 92

Lys Arg Leu Tyr Cys Lys
1               5

<210> SEQ ID NO 93
<211> LENGTH: 6
<212> TYPE: PRT
<213> ORGANISM: Artificial
<220> FEATURE:
<223> OTHER INFORMATION: Synthetic

<400> SEQUENCE: 93

Arg Arg Leu Tyr Cys Asn
1               5

<210> SEQ ID NO 94
<211> LENGTH: 9
<212> TYPE: PRT
<213> ORGANISM: Artificial
<220> FEATURE:
<223> OTHER INFORMATION: Synthetic

<400> SEQUENCE: 94

Leu Glu Ser Asn Asn Tyr Asn Thr Tyr
1               5
```